United States Patent
Koike

(10) Patent No.: US 7,560,538 B2
(45) Date of Patent: Jul. 14, 2009

(54) PORCINE ISOGLOBOSIDE 3 SYNTHASE PROTEIN, CDNA, GENOMIC ORGANIZATION, AND REGULATORY REGION

(75) Inventor: Chihiro Koike, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 355 days.

(21) Appl. No.: 10/981,935

(22) Filed: Nov. 5, 2004

(65) Prior Publication Data

US 2005/0155095 A1 Jul. 14, 2005

Related U.S. Application Data

(60) Provisional application No. 60/517,524, filed on Nov. 5, 2003.

(51) Int. Cl.
C07H 21/04 (2006.01)
(52) U.S. Cl. ............... 536/23.1; 536/23.5; 435/320.1; 435/455
(58) Field of Classification Search .............. None
See application file for complete search history.

(56) References Cited

U.S. PATENT DOCUMENTS

| | | |
|---|---|---|
| 4,797,368 A | 1/1989 | Carter et al. |
| 5,175,383 A | 12/1992 | Leder et al. |
| 5,354,768 A | 10/1994 | Terada et al. |
| 5,474,935 A | 12/1995 | Chatterjee et al. |
| 5,523,226 A | 6/1996 | Wheeler |
| 5,681,731 A | 10/1997 | Lebkowski et al. |
| 5,714,353 A | 2/1998 | Pathak et al. |
| 5,821,117 A | 10/1998 | Sandrin et al. |
| 5,849,991 A | 12/1998 | d'Apice et al. |
| 5,850,004 A | 12/1998 | MacMicking et al. |
| 5,922,601 A | 7/1999 | Baetscher et al. |
| 5,942,435 A | 8/1999 | Wheeler |
| 6,153,428 A | 11/2000 | Gustafsson et al. |
| 6,235,969 B1 | 5/2001 | Stice et al. |
| 6,258,998 B1 | 7/2001 | Damiani et al. |
| 6,331,658 B1 | 12/2001 | Cooper et al. |
| 6,413,769 B1 | 7/2002 | Gustafsson et al. |
| 6,455,037 B1 | 9/2002 | Ioannou et al. |
| 6,849,448 B1 | 2/2005 | D'Apice et al. |
| 2001/0055584 A1 | 12/2001 | Mckenzie et al. |
| 2002/0031494 A1 | 3/2002 | Sandrin et al. |
| 2002/0152488 A1 | 10/2002 | Cooper et al. |
| 2003/0014770 A1 | 1/2003 | Gustafsson et al. |
| 2003/0203427 A1 | 10/2003 | Koike |
| 2005/0120400 A1 | 6/2005 | Day et al. |

FOREIGN PATENT DOCUMENTS

| | | |
|---|---|---|
| EP | 0669829 B1 | 8/2001 |
| WO | WO 94/02616 A1 | 2/1994 |
| WO | WO 94/09803 A1 | 5/1994 |
| WO | WO 94/21799 A1 | 9/1994 |
| WO | WO 94/24870 A1 | 11/1994 |
| WO | WO 95/20661 A1 | 8/1995 |
| WO | WO 95/28412 A1 | 10/1995 |
| WO | WO 95/34202 A1 | 12/1995 |
| WO | WO 96/06165 A1 | 2/1996 |
| WO | WO 96/28967 A1 | 9/1996 |
| WO | WO 96/37602 A1 | 11/1996 |
| WO | WO 96/40244 A1 | 12/1996 |
| WO | WO 97/16064 A1 | 5/1997 |
| WO | WO 97/16727 A1 | 5/1997 |
| WO | WO 98/05768 A1 | 2/1998 |
| WO | WO 98/07444 A1 | 2/1998 |
| WO | WO 98/07837 A1 | 2/1998 |
| WO | WO 98/33528 A2 | 8/1998 |
| WO | WO 99/09141 A1 | 2/1999 |
| WO | WO 99/09163 A1 | 2/1999 |
| WO | WO 99/19469 A1 | 4/1999 |
| WO | WO 99/21415 A1 | 5/1999 |
| WO | WO 99/49029 A1 | 9/1999 |
| WO | WO 00/06194 A2 | 2/2000 |
| WO | WO 00/11147 A1 | 3/2000 |
| WO | WO 00/51424 A2 | 9/2000 |
| WO | WO 00/51424 A3 | 9/2000 |
| WO | WO 01/23541 A2 | 4/2001 |
| WO | WO 01/30992 A2 | 5/2001 |

(Continued)

OTHER PUBLICATIONS

Ayares, D., et al., (PPL Therapeutics, Inc.), "Gene targeting in livestock," Transgenic Animal Research Conference (hosted by Univ. of Calif. at Davis biotechnology program, at the Granlibakken Conf. Ctr. in Tahoe City, CA, Jul. 1999), abstract at p. 20.

(Continued)

Primary Examiner—Q. Janice Li
(74) Attorney, Agent, or Firm—King & Spalding

(57) ABSTRACT

The present invention provides porcine isoglobosidE 3 (iGb3) synthase protein, cDNA, and genomic DNA regulatory sequence. The present also invention includes porcine animals, tissue and organs as well as cells and cell lines derived from such animals, tissue and organs, which lack expression of functional iGb3 synthase. Such animals, tissues, organs and cells can be used in research and in medical therapy, including xenotransplantation. In addition, methods are provided to prepare organs, tissues, and cells lacking the porcine $iGb_3$ synthase gene for use in xenotransplantation.

10 Claims, 4 Drawing Sheets

FOREIGN PATENT DOCUMENTS

| | | | |
|---|---|---|---|
| WO | WO 0171042 A2 * | 9/2001 | |
| WO | WO 02/10337 A2 | 2/2002 | |
| WO | WO 03/055302 A1 | 7/2003 | |
| WO | WO 2004/016742 A2 | 2/2004 | |

OTHER PUBLICATIONS

Ayares, D., et al., (PPL Therapeutics, Inc.), "Gene targeting in livestock for production of novel biopharmaceuticals," *ISB News Report* (published by Information Systems for Biotechnology), Nov. 1999:5-6.

Ayares, D., et al., "Cloning pigs deficient in α1.3 galactosyltransferase," *Graft*, 4(1):80-83 (2001).

Bach, F.H., et al., "Delayed xenograft rejection," *Immunol. Today*, 17(8):379-384 (Aug. 1996).

Betthauser, J., et al., "Production of cloned pigs from in vitro systems," *Nature Biotechnology*, 18(10):1055-1059 (Oct. 2000).

Birren, B., et al., "*Homo sapiens* chromosome 8, clone RP11-24709," Sequence AC 037453, Gene Bank (PRI Apr. 1, 2002; submitted Apr. 8, 2000).

Bondioli, K., et al., Cloned pigs generated from cultured skin fibroblasts derived from a H-transferase transgenic boar, *Molecular Reproduction and Development*, 60(2):189-195 (Oct. 2001).

Brandon, E.P., et al., "targeting the mouse genome: A compendium of knockouts (part I)," *Current Biology*, 5[6]:625-634 (1995).

Brandon, E.P., et al., "targeting the mouse genome: A compendium of knockouts (part II)," *Current Biology*, 5[7]:758-765 (1995).

Brandon, E.P., et al., "targeting the mouse genome: A compendium of knockouts (part III)," *Current Biology*, 5[8]:873-881 (1995).

Butler, D., "Xenotransplant experts express caution over knockout piglets," *Nature*, 415(6868):103-104 (Jan. 10, 2002).

Capecchi, M.R., et al., "Altering the genome by homologous recombination," *Science*, 244(4910):1288-1292 (Jun. 16, 1989).

Clark, A.J., et al., "Gene targeting in livestock: a preview," *Transgenic Res.*, 9(4-5):263-275 (2000).

Clark, G.F., et al., "Toxin A from Clostridium dificile binds to rabbit erythrocyte glycolipids with terminal Gal alpha 1-3Gal beta 1-4GlcNAc sequences," *Arch.Biochem.Biophys.*, 257(1):217-229, (Aug. 15, 1987).

Cooper, D.K., et al., "Oligosaccharides and discordant xenotransplantation," *Immunol. Rev.*, 141:31-58 (Oct. 1994).

Cooper, D.K.C., et al., "Genetically engineered pigs," *Lancet*, 342:682-683 (Sep. 11, 1993).

Costa, C., et al., "Expression of the human α1,2-fucosyltransferase in transgenic pigs modifies the cell surface carbohydrate phenotype and confers resistance to human serum-mediated cytolysis," *FASEB J.*, 13:1762-1773 (Oct. 1999).

Dabkowski, P.L., et al., "Characterisation of a cDNA clone encoding the pig alpha 1,3 galactosyltransferase: implications for xenotransplantation," *Transplant Proc.*, 25(5):2921 (Oct. 1993).

Dabkowski, P.L., et al., "Isolation of a cDNA clone encoding the pig alpha 1,3 galactosyltransferase," *Transplant Proc.*, 26(3):1335 (Jun. 1994).

Dai, Y., et al., "Targeted disruption of the α1,3-galactosyltransferase gene in cloned pigs," *Nature Biotechnology*, 20:251-255 (Mar. 2002).

Dalmasso, A.P., et al., "Inhibition of complement-mediated endothelial cell cytotoxicity by decay-accelerating factor: Potential for prevention of xenograft hyperacute rejection," *Transplantation*, 52(3):530-533 (Sep. 1991).

Dalmasso, A.P., et al., "Reaction of complement with endothelial cells in a model of xenotransplantation," *Clin. Exp. Immunol.*, 86:31-35 (1991).

D'Apice, A.J., et al., "Two genetic approaches to the galactose alpha 1,3 galactose xenoantigen," *Transplant Proc.*, 28(2):540 (Apr. 1996).

Denning, C., et al., "Gene targeting in primary fetal fibroblasts from sheep and pig," *Cloning Stem Cells*, 3(4):221-231 (2001).

Denning, C., et al., "Deletion of the α(1,3)galactosyl transferase (GGTA1) gene and the prion protein (*PrP*) gene in sheep," *Nature Biotechnology*, 19:559-562 (Jun. 2001).

Fabre, J.W., "Nudging xenotransplantation towards humans," *Nature Med.*, 1(5):403-404 (May 1995).

Galili, U., "The α-gal epitope (Galα-3Galβ-4GlcNAc-R) in xenotransplantation," *Biochimie*, 83:557-563 (2001).

Galili, U., et al., "Evolution and pathophysiology of the human natural anti-alpha-galactosyl IgG (anti-Gal) antibody," *Springer Semin. Immunopathol.*, 15(2-3):155-171 (1993).

Galili, U., et al., "Evolutionary relationship between the natural anti—Gal antibody and the Gal alpha 1—3Gal epitope in primates," *Proc. Natl. Acad. Sci., USA.*, 84(5):1369-1373 (Mar. 1987).

Galili, U., et al., "Human natural anti-alpha-galactosyl IgG. II. The specific recognition of alpha (1-3)-linked galactose residues," *J. Exp. Med.*, 162(2):573-582 (Aug. 1, 1985).

Galili, U., et al., "Man, apes, and old world monkeys differ from other mammals in the expression of α-galactosyl epitopes on nucleated cells," *J.Biol.Chem.*, 263(33):17755-17762 (Nov. 25, 1988).

Gassmann, M., et al., "Maintenance of an extrachromosomal plasmid vector in mouse embryonic stem cells," *Proc. Natl. Acad. Sci. USA*, 92(5):1292-1296 (Feb. 28, 1995).

Gastinel, L.N., et.al., "Bovine a1,3-galactosyltransferase catalytic domain structure and its relationship with ABO histo-blood group and glycosphingolipid glycosyltransferases," *EMBO Journal*, 20(4):638-649 (2001).

Hammer, R.E., et al., "Production of transgenic rabbits, sheep and pigs by microinjection," *Nature*, 315(6021):680-683 (Jun. 20-26, 1985).

Hancock, W., "Hyde Park Speakers Corner: Xeno-stagnation," *AST Newsletter*, 6(3):31-33 (Summer 1999) (American Society of Transplantation, Moorestown, NJ).

Harduin-Lepers, A., et al., "Characterization of two cis-regulatory regions in the murine beta 1,4-galactosyltransferase gene. Evidence for a negative regulatory element that controls initiation at the proximal site," *J. Biol. Chem.*, 268(19):14348-14359 (Jul. 5, 1993).

Harrison, S.J., et al., "Efficient generation of α(1,3) galactosyltransferase knockout porcine fetal fibroblasts for nuclear transfer," *Transgenics Research*, 11:143-150 (2002).

Hasty, P., et al., "The length of homology required for gene targeting in embryonic stem cells," *Mol. Cell Biol.*,11(11):5586-5591 (Nov. 1991).

Hayashi, S., et al., "Adenovirus-mediated gene transfer of antisense ribozyme for alpha (1,3)galactosyltransferase gene and alpha (1,2)fucosyltransferase gene in xenotransplantation," *Transplant Proc.*, 29(4):2213 (Jun. 1997).

Hennet, T., "The galatoxyltransferase family," *Cell. Mol. Life Sci.*, 59:1081-1095 (2002).

International Preliminary Examination Report, PCT/US04/37070 (Apr. 12, 2006).

International Search Report, PCT/US04/37070 (Oct. 11, 2005).

Joyner, A.L., "Production of a mutation in mouse En-2 gene by homologous recombination in embryonic stem cells," *Nature*, 338(6211)::153-156 (Mar. 9, 1989).

Joziasse, D.H., et al., "Bovine α1→3-galactosyltransferase: Isolation and characterization of a cDNA clone: Identification of homologous sequences in human genomic DNA,"*J. Biol. Chem.*,264(24):14290-14297 (Aug. 25, 1989).

Joziasse, D.H., et al., "Characterization of a α1→3-galactosyltransferase homologue on human chromosome 12 that is organized as a processed pseudogene," *The Journal of Biological Chemistry*, 266(11):6991-6998 (Apr. 15, 1991).

Joziasse, D.H., et al., "Murine α1→3-galactosyltransferase: A single gene locus specifies four isoforms of the enzyme by alternative splicing," *J. Biol. Chem.*, 267(8) 5534-5541 (Mar. 15, 1992).

Joziasse, D.H., et al., "Xenotransplantation: the importance of the Galalpha1,3Gal epitope in hyperacute vascular rejection," *Biochim. Biophys. Acta*, 1455(2-3):403-418 (Oct. 8, 1999).

Just, I., et al., "The low molecular mass GTP-binding protein rho is affected by toxin A from *Clostridium difficile*," *J. Clin. Invest.*, 95:1026-1031 (1995).

Katayama, A., et al., "Porcine α-1,3-galactosyltransferase: full length cDNA cloning, genomic organization, and analysis of splicing variants," *Glyconjugate Journal*, 15:583-589 (1998).

Kelly, R.J., et al., "Sequence and expression of a candidate for the human Secretor blood group alpha (1,2)fucosyltransferase gene (FUT2). Homozygosity for an enzyme-inactivating nonsense mutation commonly correlates with the non-secretor phenotype," *J. Biol. Chem.*, 270(9):4640-4649 (Mar. 3, 1995).

Keusch, J.J., et al., "Cloning of Gb3 synthase, the key enzyme in globo-series glycosphingolipid synthesis, predicts a family of alpha 1, 4-glycosyltransferases conserved in plants, insects, and mammals," *J. Biol. Chem.*, 275(33):25315-25321 (Aug. 18, 2000).

Kilby, N.J., et al., "Site-specific recombinases: tools for genome engineering," *Trends in Genetics*, 9(12):413-421 (Dec. 1993).

Koike, C., et al., "Comparison of the regulatory regions of the of α1,3galactosyltransferase gene between murine and porcine species," *Transplantation Proceedings*, 33:710-711 (2001).

Koike, C., et al., "Direct gene replacement of the mouse α(1,3)-galactosyltransferase gene with human α(1,2)-fucosyltransferase gene: Converting α-galactosyl epitopes into H antigens," *Xenotransplantation*, 4:147-153 (1997).

Koike, C., et al., "Introduction of α(1,2)-fucosyltransferase and its effect of α-Gal epitopes in transgenic pig," *Xenotransplantation*, 3:81-86 (1996).

Koike, C., et al., "Isolation of the regulatory regions and genomic organization of the porcine α1,3-galactosyltransferase gene," *Transplantation*, 70(9):1275-1283 (Nov. 15, 2000).

Koike, C., et al., "Molecular basis of evolutionary loss of the α1,3-galactosyltransferase gene in higher primates," *J. Biol. Chem.*, 277(12):10114-101120 (Mar. 22, 2002).

Lai, L., et al., "Production of α-1,3-galactosyltransferase knockout pigs by nuclear transfer cloning," *Science* 295:1089-1092 (Feb. 8, 2002) and supplementary data, *Science Express*, Jan. 3, 2002.

Larsen, R.D., et al., "Frameshift and nonsense mutations in a human genomic sequence homologous to a murine UDP-Gal:beta-D-Gal(1,4)-D-GlcNAc alpha(1,3)-galactosyltransferase cDNA," *J. Biol. Chem.*,265(12):7055-7061 (Apr. 25, 1990).

Larsen, R.D., et al., "Isolation of a cDNA encoding a murine UDPgalactose:beta-D-galactosyl- 1,4-N-acetyl-D-glucosaminide alpha-1,3-galactosyltransferase: expression cloning by gene transfer," *Proc. Natl. Acad. Sci., U S A.*, 86(21):8227-8231 (Nov. 1989).

Larsen, R.D., et al., "Molecular cloning, sequence, and expression of a human GDP-L-fucose:beta-D-galactoside 2-alpha-L-fucosyltransferase cDNA that can form the H blood group antigen," *Proc. Natl. Acad. Sci., U S A.*, 87(17):6674-6678 (Sep. 1990).

Lo, N.W., et al., "Transcription of the beta-galactoside alpha 2,6-sialyltransferase gene in B lymphocytes is directed by a separate and distinct promoter," *Glycobiology*, 6(3):271-279 (Apr. 1996).

Luckow, V.A., et al., "Trends in the development of baculovirus expression vector," *Bio/Technology*, 6:47-55 (Jan. 1988).

Mansour, S.L., et al., "Disruption of the proto-oncogene int-2 in mouse embryo-derived stem cells: a general strategy for targeting mutations to non-selectable genes," *Nature*, 336(6197):348-352 (Nov. 24, 1988).

Masaya, C., and Ryuichi, O. (Amano Pharmaceutical Co. Ltd.), "Mutarotase gene," *Pat. Abstr. Japan*, pub. No. 06-253856 (A1) (Sep. 13, 1994), provided with Seq. ID No. 1 DNA comparison.

McCarrick, J.W. 3rd, et al., "Positive-negative selection gene targeting with the diphtheria toxin A-chain gene in mouse embryonic stem cells," *Transgenic Res.*, 2(4):183-190 (Jul. 2, 1993).

McCreath, K.J., et al., "Production of gene-targeted sheep by nuclear transfer from somatic cells," *Nature*, 405:1066-1069 (Jul. 29, 2000).

McCurry, K.R., et al., "Human complement regulatory proteins protect swine-to-primate cardiac xenografts from humoral injury," *Nature Med.* 1(5):423-427 (May 1995).

McKenzie, I.F., et al., "Strategies to overcome the anti-Gal alpha (1-3)Gal reaction in xenotransplantation," *Transplant Proc.*, 28(2):537 (Apr. 1996).

Miyagawa, S., et al., "Remodeling of the major pig xenoantigen by N-acetylglucosaminyltransferase III in transgenic pig," *J. Biol. Chem.*, 276(42):39310-39319 (Oct. 19, 2001).

Moreadith, R.W., et al., "Gene targeting in embryonic stem cells: the new physiology and metabolism," *J. Mol. Med.*, 75(3):208-216 (Mar. 1997).

Mueller, S., et al., "Chimeric pigs following blastocyst injection of transgenic porcine primordial germ cells," *Mol. Reprod. Dev.*, 54(3):244-254 (Nov. 1999).

Mullins, L.J., et al., "Transgenesis in the rat and larger mammals," *J. Clin. Invest.*, 97(7):1557-1560 (Apr. 1, 1996).

Nagasaka, T., et al., "Inhibitory effect of α(1,2) fucosyltransferase recombinant adenoviral vector on αGal expression," *Transplantation Proceedings*, 30:3837-3838 (1998).

Onishi, A., et al., "Pig cloning by microinjection of fetal fibroblast nuclei," *Science*, 289:1188-1190 (Aug. 18, 2000).

Osman, N., et al., "Combined transgenic expression of alpha-galactosidase and alpha 1,2-fucosyltransferase leads to optimal reduction in the major xenoepitope Galalpha(1,3)Gal," *Proc. Natl. Acad. Sci. U S A.*, 94(26):14677-14682 (Dec. 23, 1997).

Pera, M.F., et al., "Human embryonic stem cells," *J. Cell. Sci.*, 113 (Pt 1):5-10 (Jan. 2000).

Phelps, C.J., et al., "Production of α1,3-galactosyltransferase-deficient pigs," *Science*, 299:411-414 (Jan. 17, 2003).

Polejaeva, I.A., "Cloning pigs: advances and applications," *Reprod.*, 58 (Suppl.):293-300 (2001).

Polejaeva, I.A., et al., "Cloned pigs produced by nuclear transfer from adult somatic cells," *Nature*, 407:86-90 (Sep. 7, 2000).

Porter, A.C.G., et al., "Gene Targeting: Techniques and applications to transplantation," *Transplantation*, 64:1227-1235 (Nov. 15, 1997).

Pray, L., "Refining transgenic mice," *The Scientist* 16(13):34 (Jun. 24, 2002).

Pursel V.G., et al., "Progress on gene transfer in farm animals," *Vet. Immunol. Immunopathol.*, 17(1-4):303-312 (Dec. 1987).

Ramsoondar, J.J., et al., "Production of α1,3-galactosyltransferase-knockout cloned pigs expressing human α1,2-fucosyltransferase," *Biol. of Reproduction*, 69:437-445 (online before print Apr. 2, 2003).

Rexroad, C.E. Jr., et al., "Production of transgenic sheep with growth-regulating genes," *Mol. Reprod. Dev.*, 1(3):164-169 (1989).

Rexroad, C.E. Jr., et al., "Insertion, expression and physiology of growth-regulating genes in ruminants," *J. Reprod. Fertil. Supp.*, 41:119-124 (1990).

Rubnitz, J., et al., "The minimum amount of homology required for homologous recombination in mammalian cells," *Mol. Cell. Biol.*, 4(11):2253-2258 (Nov. 1984).

Sandrin, M.S., et al., Identification of Gal(α1,3)Gal as the major epitope for pig-to-human vascularized xenografts, *Transplant Rev.*, 8(3):134-139 (Jul. 1994).

Sandrin, M.S., et al., "Characterization of cDNA clones for porcine α(1,3)galactosyl transferase: The enzyme generating the Galα(1,3)Gal epitope," *Xenotransplantation*, 1:81-88 (1994).

Sao, H., et al., "A new marrow T cell depletion method using anti-CD6 mnoclonal antibody-conjugated magnetic beads and its clinical application for prevention of acute graft-vs.-host disease in allogenic bone marrow transplantation: Rrsults of a phase I-II trial," *Intl. J. Hematol.*, 69(1):27-35 (Jan. 1999).

Sasaki, K., et al., "Expression cloning of a novel Gal β(1-3/1-4) GlcNAc α2,3-sialyltransferase using lectin resistance selection," *J. Biol. Chem.*, 268(30):22782-22787 (Oct. 25, 1993).

Shaper, N.L., et al., "Characterization of the full length cDNA for murine beta-1,4-galactosyltransferase. Novel features at the 5'-end predict two translation start sites at two in-frame AUGs," *J. Biol. Chem.*, 263(21):10420-10428 (Jul. 25, 1988).

Sharma, A., et al., "Pig cells that lack the gene for α1,3-galactosyltransferase express low levels of the gal antigen," *Transplantation*, 75(4):430-436 (Feb. 7, 2003).

Simons, J.P., et al., "Gene transfer into sheep," *Bio/Technology*, 6(1):179-183 (Jan. 1988).

Smith, C.M., "Technical knockout: Gene-targeting strategies provide an avenue for studying gene function," *The Scientist*,14(15):32 (Jul. 24, 2000).

Starzl, T.E., et al., "Antigen localization and migration in immunity and tolerance," *N. Engl. J. Med.*, 339(26):1905-1913 (Dec. 24, 1998).

Starzl, T.E., et al., "The biological basis of and strategies for clinical xenotransplantation," *Immunol. Rev.*, 141:213-244 (Oct. 1994).

Starzl, T.E., et al., "Will xenotransplantation ever be feasible?" *J. Am. Coll. Surg.*, 186(4):383-387 (Apr. 1998).

Stolberg, S.G., "Could this pig save your life?" *N. Y. Times Magazine.*, Oct. 3, 1999, pp. 46-51.

Stone, K.R., et al., "Porcine and bovine cartilage transplants in cynomolgus monkey," *Transplantation*, 63(5):640-645 (Mar. 15, 1997).

Strahan, K., et al., "Pig alpha1,3galactosyltransferase: A major target for genetic manipulation in xenotransplantation," *Frontiers in Bioscience*, 1:e34-41 (Jul. 1, 1996).

Strahan, K.M., et al., "cDNA sequence and chromosome localization of pig alpha 1,3 galactosyltransferase," *Immunogenetics*, 41(2-3):101-105 (1995).

Strahan, K.M., et al., "Pig alpha 1, 3galactosyltransferase: sequence of a full-length cDNA clone, chromosomal localisation of the corresponding gene, and inhibition of expression in cultured pig endothelial cells," *Transplant Proc.*, 27(1):245-246 (Feb. 1995).

Svensson, E.C., et al., "Organization of the β-galactoside α2,6-sialyltransferase gene. Evidence for the transcriptional regulation of terminal glycosylation," *J. Biol. Chem..* 265(34):20863-20868 (Dec. 5, 1990).

Svensson, E.C., et al., "Regulated expression of alpha 2,6-sialyltransferase by the liver-enriched transcription factors HNF-1, DBP, and LAP," *J. Biol. Chem.*.267(5):3466-3472 (Feb. 15, 1992).

Tanemura, M., et al., "Differential expression of the α-gal epitopes (Galα1-3Galβ1-4GlcNAc-R) on pig and mouse organs," *Transplantation*, 69(1):187-190 (Jan. 15, 2000).

Tanemura, M., et al., "Reduction of the major swine xenoantigen, the α-galactosyl epitope by transfection of the α2,3-sialyltransferase gene," *J..Biol.Chem.*, 273(26):16421-16425 (Jun. 26, 1998).

Tanemura, M., et al., "Elimination of anti-gal B cells by α-gal ricin," *Transplantation*, 73(12):1859-1868 (Jun. 27, 2002).

Tearle, R.G., et al., "The α-1,3-galactosyltransferase knockout mouse," *Transplantation*, 61(1):13-19 (Jan. 15, 1996).

Thall, A.D., et al., "Oocyte galα1,3gal epitopes implicated in sperm adhesion to the zona pellucida glycoprotein ZP3 are not required for fertilization in the mouse," *J. Biol. Chem.*, 270 (27):21437-21440 (Sep. 15, 1995).

Thall, A.D., "Generation of a1,3galactosyltransferase deficient mice," Chapter 11 of *Subcellular Chemistry*, vol. 32: *a-Gal and Anti-Gal*, Galili and Avila, eds., (Kluwer Academic / Plenum Publishers, New York, 1999), pp. 259-279.

Thomas, K.R., et al., "Site-directed mutagenesis by gene targeting in mouse embryo-derived stem cells," *Cell*, 51(3):503-512 (Nov. 6, 1987).

Vanhove, B., et al., "Porcine α1,3-galactosyltransferase: Tissue-specific and regulated expression of splicing isoforms," *Biochim. Biophys. Acta*, 1356(1):1-11 (Mar. 27, 1997).

Vanhove, B., et al., "Transcriptional and posttranscriptional regulation of α1,3-galactosyltransfer-ase in activated endothelial cells results in decreased expression of Galα1,3Gal," *Glycobiology*, 8(5):481-487 (May 1998).

Vanhove, B., et al., "Variability of alpha 1,3-galactosyltransferase splicing isoforms in pig tissues," *Transplant Proc.* 28(2):622-623 (Apr. 1996).

Vaughan, H.A., et al., "Gal α(1,3)Gal is the major xenoepitope expressed on pig endothelial cells recognized by naturally occurring cytotoxic human antibodies," *Transplantation*, 58(8):879-882 (Oct. 27, 1994).

Vize P.D., et al., "Introduction of porcine growth hormone fusion gene into transgenic pigs promotes growth," *J. Cell Sci.*,;90 ( Pt 2):295-300 (Jun. 1988).

Wagner, "Development of transgenic pigs," *J. Cellular Biochem.*, 13B (Suppl.):164 (1989) (Abstract).

Weinstein, J., et al., "Primary structure of beta-galactoside alpha 2,6-sialyltransferase. Conversion of membrane-bound enzyme to soluble forms by cleavage of the NH2-terminal signal anchor," .*J. Biol. Chem.*, 262(36):17735-17743 (Dec. 25, 1987).

White, D.J.G., et al., "Expression of human decay accelerating factor or membrane cofactor protein genes on mouse cells inhibits lysis by human complement," *Transplantation Proceedings*, 24(2):474-476 (Apr. 1992).

Yamamoto, F.-I., et al., "Genomic organization of human histo-blood group ABO genes," *Glycobiology*, 5(1):51-58 (1995).

Ye, Y., et al., "Evidence that intravenously administered a-galactosyl carbohydrates reduce baboon serum cytotoxicity to pig kidney cells (PK15) and transplanted pig hearts," *Transplantation*, 58(3):330-337 (Aug. 15, 1994).

* cited by examiner

```
GGCCTGGAAGAGAATCCTCTGGTTGATCCTACTTGCACTTGACCCTCTTAGGGCTGCTCCTGT
TTGGCCTCCCTGCTGTCAGGCATCTGGAAGTCCTTGTCCCGTGGTGTCTGCCTTTGACCAGA
ACACCCTGCTGGAGACAACTCCACGGGTCCCTGCATCCTTGGCCCGGCCTGAAGTCCTGA
CCTGCACCTCCTGGGGCCCCATTATATGGGACGGCACCTTCGACCCAGATGTGGCCAGCA
AGAGGCTACCCAGCAGAACCTCACCATTGGCCCTGACGGTCTTTGCTGTGCAGGTACCTGGAG
AAGTACCTGGCACACTTCCTGGAGACAGCAGCCACTTCATGGTGGGCCAGTGCGTCGCGT
ACTACGTGTTCACCGAGCGCCCTGCAGCGCCCTGCTGCTGGCCCCGACCGTGGGCT
ACGGATGAGCACTTGGCGCTGAGCGGCGCTGCAGGACGTGCCATGCGCGC
GCTGCACCCGGCTCGGGGCGCCTCGGGCCCGCCTGGGCGTGCTTCGTGTTCTGCATGGACGTG
GATCAGCACTTCAGTGGCCACTCTACTACCATGCGGGGTGACACGCGGTGCAGTGCACG
CCTGGCACTACCGCTGGGGCGAGGGCGACTCTACTACCATGCGGGGTGACACGCGGTGCCACG
CTGCCGGGCGTCTGACGCGCACAAGAGCCACCTCAATAAGTTCTTCTGCTGCACCAAGCTGC
GCCGCGGGCGTCTGACGCGCACAAGAGCCACCTCAATAAGTTCTTCTGCTGCACCAAGCTGC
TGTCGCCTGAGTTTTGCTGGAGCCCGATCTTGGCGTGGCTGAGATCCACTGCCCGCCTG
CTCTGGGCGCCCAAGGAGTATGCCCTGCTGCAAAGTGCTGTGAAACGCGGTGAGGGCCTTCTGGA
AGCAGCGGGCACTGGCCTTTGGGACGTGTGGGGGACGTGGGGGACCATCCTTCCATGGCTG
CAGGAAGCTGCAGCTCCAGTGCCTGGAGACTGCTCGGGACCATTCACCTCTGAGTTCAGGGAGGCCCT
CCGGGCACCCTCCAGTGCCCCGAGGACCCAGAGGATCTATGAGTCAGGTCAGCTGGA
CTGAAGAGAGATGTTTAGCCCCTTCCCCATATCCCTACGCTTATATGGTACTGAGGCGCCAAAA
GGGAACATGGCCCGAGGACCCAGAGGATCTATGAGTCAGCCTGTGAGGTCAGCTGGA
GAGCAAGACTGACCCTCAGGCAGCCAAATACATCTGCTTCTAGGCACAAGCCCCAGATGAAGAAACT
CAGTGGCATCCGGGTTCCCTGACTTTGCTGGTT

SEQ ID NO: 1
```

Figure 2

AWKRILWWLILLALDLLGLLLFGLPAVRHLEVLVPVGVCPLTRTPLLGDN
STGPLHPWARPEVLTCTSWGGPIIWDGTFDPDVAQQEATQQNLTIGLTVF
AVGRYLEKYLAHFLETAEQHFMVGQCVAYYVFTERPAAMPRLLLGPDR
GLRMEHLARERRWQDVSMARMRALHPALGGRLGHGACFVFCMDVDQH
FSGAFGPEALAESVAQLHAWHYRWPRWLLPFERDTRSAAVLGPGEGDL
YYHAAVFGGSVAALRRLTAHCARGLRRDRSRGLEARWHDKSHLNKFFW
LHKPTKLLSPEFCWSPDLGRWAEIHCPRLLWAPKEYALLQS

SEQ ID NO: 2

PORCINE ISOGLOBOSIDE 3 SYNTHASE PROTEIN, CDNA, GENOMIC ORGANIZATION, AND REGULATORY REGION

CROSS REFERENCE TO RELATED APPLICATIONS

This application claims priority to U.S. provisional patent application Ser. No. 60/517,524, filed Nov. 5, 2003.

This was produced in part using funds from the Federal government under Grant Nos. DK064207 and DK388899. Accordingly, the Federal government has certain rights in this invention.

FIELD OF THE INVENTION

The present invention provides porcine isoglobside 3 (iGb3) synthase protein, cDNA, and genomic DNA regulatory sequences. Further, the present invention includes porcine animals, tissue and organs as well as cells and cell lines derived from such animals, tissue and organs, which lack expression of functional iGb3 synthase. Such animals, tissues, organs and cells can be used in research and in medical therapy, including xenotransplantation. In addition, methods are provided to prepare organs, tissues, and cells lacking the porcine iGb3 synthase gene for use in xenotransplantation.

BACKGROUND OF THE INVENTION

The unavailability of acceptable human donor organs, the low rate of long term success due to host versus graft rejection, and the serious risks of infection and cancer are the main challenges now facing the field of tissue and organ transplantation. Because the demand for acceptable organs exceeds the supply, many people die each year while waiting for organs to become available. To help meet this demand, research has been focused on developing alternatives to allogenic transplantation. For example, dialysis has been available to patients suffering from kidney failure, artificial heart models have been tested, and other mechanical systems have been developed to assist or replace failing organs. Such approaches, however, are quite expensive, and the need for frequent and periodic access to machines greatly limits the freedom and quality of life of patients undergoing this type of therapy.

Xenograft transplantation represents a potentially attractive alternative to artificial organs for human transplantation. The potential pool of nonhuman organs is virtually limitless, and successful xenograft transplantation would not render the patient virtually tethered to machines as is the case with artificial organ technology. Host rejection of such cross-species tissue, however, remains a major hurdle in this area, and the success of organ transplants depends on avoiding rejection of the transplant.

The forms of transplant rejection are clinically classified by their time frames and histologies. Hyperacute rejection (HAR), for example, occurs within minutes to hours following transplant. Hyperacute rejection is characterized by rapid thrombotic occlusion of the graft vasculature that begins within minutes to hours after host blood vessels are anastomosed to graft vessels. Hyperacute rejection is mediated by antibodies that pre-exist in naive hosts, the so-called 'natural antibodies,' which bind to endothelium and activate complement. Antibody and complement induce a number of changes in the graft endothelium that promote intravascular thrombosis. On the other hand, acute rejection typically occurs within 1-30 days, and chronic rejection occurs thereafter, sometimes taking several months to years. Some noted xenotransplants of organs from apes or old-world monkeys (e.g., baboons) into humans have been tolerated for months without rejection. However, such attempts have ultimately failed due to a number of immunological factors. Even with heavy immunosuppressive drugs used to suppress HAR, a low-grade innate immune response ultimately leads to destruction of the transplanted organs. This low grade innate immune response is attributable, in part, to failure of complement regulatory proteins (CRPs) within the graft tissue to control activation of heterologous complement on graft endothelium (see e.g., Starzl et al., Immunol. Rev., 141, 213-44 (1994)). In addition to HAR, DXR, also known as acute vascular rejection, and T-cell mediated responses also play a major role in host graft rejection. It is likely that a multifaceted strategy will need to be employed to overcome the barriers to successfully transplant non-human organs into human recipients.

Complicating the efficacy of xenotransplants further is the fact that drugs used to control innate immune responses to the xenograft can cause a non-specific depression of the immune system. Patients on such immune suppressive agents are more susceptible to the development of life-threatening infections and neoplasia.

In an effort to develop a pool of immuno-acceptable organs for xenotransplantation into humans, researchers have engineered animals producing human CRPs, an approach which has been demonstrated to delay, but not eliminate, xenograft destruction in primates (McCurry et al., Nat. Med., 1, 423-27 (1995); Bach et al., Immunol. Today, 17, 379-84 (1996)). However, organs surviving HAR may still be subjected to delayed xenograft rejection (DXR). This is characterized by the infiltration of recipient inflammatory cells and thrombosis of graft vessels, leading to ischaemia of the organ.

Whereas HAR is associated with rapid, protein-synthesis-independent, type I endothelial cell activation that results in graft rejection within minutes or hours, DXR, also known as acute vascular rejection, relates primarily to type II endothelial cell activation (see Bach F. H. et al., Immunology Today 17(8):379-384 (1996)). This response involves transcriptional induction of genes and subsequent protein synthesis resulting in the expression of adhesion molecules, cytokines, procoagulant molecules and others (Prober J. S. et al., Transplantation 50: 537-544 (1990); Prober J. S. et al., Physiol. Rev. 70: 427451 (1990); Cotran R. S. et al., Kidney Ins. 35: 969-975 (1989)). DXR is characterized by the infiltration into the graft of host monocytes and natural killer cells (NK), which promote intragraft inflammation and thrombosis (Bach F. H. et al., Immunology Today 17(8):379-384 (1996)).

Inhibition of complement by soluble complement receptor type I (sCR1) combined with immunosuppression has been reported to delay the occurrence of DXR/AVR of porcine hearts transplanted into cynomoigus monkeys (Davis, EA et al., Transplantation 62:1018-23 (1996)). Transplantation of pig kidneys expressing human decay accelerating factor to cynomoigus monkeys also had some protective effect against DXR/AVR (Zaid A. et al., Transplantation 65:1584-90 (1998); Loss M et al., Xenotransplantation 7. 186.9 (2000)).

PCT Publication WO 02/30985A2 to Tanox Inc., teaches a method to suppress E-selectin in order to reduce DXR responses. E-selectin (also known as ELAM-1, CD62, and CD62E) is a cytokine inducible cell surface glycoprotein cell adhesion molecule that is found exclusively on endothelial cells. E-selectin mediates the adhesion of various leukocytes, including neutrophils, monocytes, eosinophils, natural killer (NK) cells, and a subset of T cells, to activated endothelium (Bevilacqua, et al., Science 243: 1160 (1989); Shimuzu, et al., Nature 349:799 (1991); Graber, et al., J. Immunol. 145: 819 (1990); Carlos, et al., Blood 77: 2266 (1991); Hakkert, et al., Blood 78:2721 (1991); and Picker, et al., Nature 349:796 (1991)). The expression of E-selectin is induced on human endothelium in response to the cytokines IL-1 and TNF, as well as bacterial lipopolysaccharide (LPS), through transcriptional up-regulation (Montgomery, et al., Proc Natl Acad Sci 88:6523 (1991)). The human leukocyte receptor for human E-selectin has been identified (Berg, et al., J. Biol. Chem. 23: 14869 (1991) and Tyrrell, et al., Proc Natl Acad Sci 88:10372 (1991)). Structurally, E-selectin belongs to a family of adhesion molecules termed "selectins" that also includes P-selectin and L-selectin (see reviews in Lasky, Science 258: 964 (1992) and Bevilacqua and Nelson, J. Clin. Invest. 91:379 (1993)). These molecules are characterized by common structural features such as an amino-terminal lectin-like domain, an epidermal growth factor (EGF) domain, and a discrete number of complement repeat modules (approximately 60 amino acids each) similar to those found in certain complement binding proteins. Clinically, increased E-selectin expression on endothelium is associated with a variety of acute and chronic leukocyte-mediated inflammatory reactions including allograft rejection (Allen, et al., Circulation 88: 243 (1993); Brockmeyer, et al., Transplantation 55:610 (1993); Ferran, et al Transplantation 55:605 (1993); and Taylor, et al., Transplantation 54: 451 (1992)). Studies in which the expression of human E-selectin in cardiac and renal allografts undergoing acute cellular rejection was investigated have demonstrated that E-selectin expression is selectively up-regulated in vascular endothelium of renal and cardiac tissue during acute rejection (Taylor, et al., Transplantation 54: 451 (1992)). Additionally, increased E-selectin expression correlates with the early course of cellular rejection and corresponds to the migration of inflammatory cells into the graft tissue (Taylor, et al., Transplantation 54: 451 (1992)). Taken together, these studies provide evidence that cytokine-induced expression of E-selectin by donor organ endothelium contributes to the binding and subsequent transmigration of inflammatory cells into the graft tissue and thereby plays an important role in acute cellular allograft rejection.

In addition to complement-mediated attack, human rejection of discordant xenografts appears to be mediated by a common antigen: the galactose-$\alpha$(1,3)-galactose (gal-$\alpha$-gal) terminal residue of many glycoproteins and glycolipids (Galili et al., Proc. Nat. Acad. Sci., (USA), 84, 1369-73 (1987); Cooper, et al., Immunol. Rev., 141, 31-58 (1994); Galili, et al., Springer Sem. Immunopathol, 15, 155-171 (1993); Sandrin, et al., Transplant Rev., 8, 134 (1994)). This antigen is chemically related to the human A, B, and O blood antigens, and it is present on many parasites and infectious agents, such as bacteria and viruses. Most mammalian tissue also contains this antigen, with the notable exception of old world monkeys, apes and humans. (Joziasse, et al., J. Biol. Chem., 264, 14290-97 (1989)). Individuals without such carbohydrate epitopes produce abundant naturally occurring antibodies (IgM as well as IgG) specific to the epitopes. Many humans show significant levels of circulating IgG with specificity for gal-$\alpha$-gal carbohydrate determinants (Galili, et al., J. Exp. Med, 162, 573-82 (1985); Galili, et al., Proc. Nat. Acad Sci. (USA), 84, 1369-73 (1987)). The $\alpha$-galactosyltransferase ($\alpha$-GT) enzyme catalyzes the formation of gal-$\alpha$-gal moieties. Research has focused on the modulation or elimination of this enzyme to reduce or eliminate the expression of gal-$\alpha$-gal moieties on the cell surface of xenotissue.

The elimination of the $\alpha$-galactosyltransferase gene from porcine has long been considered one of the most significant hurdles to accomplishing xenotransplantation from pigs to humans. Two alleles in the pig genome encode the $\alpha$-GT gene. Single allelic knockouts of the $\alpha$-GT gene in pigs were reported in 2002 (Dai, et al. Nature Biotechnol., 20:251 (2002); Lai, et al., Science, 295:1089 (2002)).

Recently, double allelic knockouts of the $\alpha$-GT gene have been accomplished (Phelps, et al., Science, 299: pp. 411-414 (2003)). WO 2004/028243 to Revivicor Inc. describes porcine animal, tissue, organ, cells and cell lines, which lack all expression of functional $\alpha$1,3 galactosyltransferase ($\alpha$1,3-GT). Accordingly, the animals, tissues, organs and cells lacking functional expression of $\alpha$1,3-GT can be used in xenotransplantation and for other medical purposes.

PCT patent application WO 2004/016742 to Immerge Biotherapeutics, Inc. describes $\alpha$(1,3)-galactosyltransferase null cells, methods of selecting GGTA-1 null cells, $\alpha$(1,3)-galactosyltransferase null swine produced therefrom (referred to as a viable GGTA-1 null swine), methods for making such swine, and methods of using cells, tissues and organs of such a null swine for xenotransplantation.

$\alpha$(1,3)-Galactosyltransferase, however, is not the only enzyme that synthesizes the Gal$\alpha$(1,3)Gal motif. Originally, Gal$\alpha$(1,3)Gal was thought to be exclusively synthesized by $\alpha$(1,3)GT. More recent studies show that isogloboside 3 (iGb3) synthase is also capable of synthesizing Gal$\alpha$(1,3)Gal motifs (Taylor SG, et al Glycobiology 13(5): 327-337 (2003)). In contrast to $\alpha$(1,3)GT, iGb3 synthase preferentially modifies glycolipids over glycoprotein substrates (Keusch et al. (2000) J.Bio.Chem. 275:25308-25314). iGb3 synthase acts on lactosylceramide (LacCer (Gal$\beta$1,4Glc$\beta$1Cer)) to form the glycolipid isogloboid structure iGb3 (Gal$\alpha$1, 3Gal$\beta$1,4Glc$\beta$1Cer), initiating the synthesis of the isoglobo-series of glycoshingolipids.

Studies performed on rats confirm that two independent genes encoding distinct glycosyltransferases, $\alpha$(1,3)GT and iGb3 synthase, are capable of synthesizing the Gal$\alpha$(1,3)Gal motif (Taylor et al. (2003) Glycobiology 13(5):327-337). These separate and distinct glycosyltransferases act through two different glycosylation pathways. Transfection studies have shown that $\alpha$(1,3)GT synthesizes Gal$\alpha$(1,3)Gal on glycoproteins, whereas the synthesis of the Gal$\alpha$(1,3)Gal motif on the glycolipid is facilitated by iGB3 synthase. In addition, it has been shown that $\alpha$(1,3)GT is incapable of synthesizing the Gal$\alpha$(1,3)Gal on glycolipids (Taylor et al. (2003) Glycobiology 13(5):327-337). These findings have refuted the previously held belief that $\alpha$(1,3)GT was the sole Gal$\alpha$(1,3)Gal motif synthesizing enzyme.

The presence of the iGb3 synthase gene, and its contribution to the biosynthesis of the highly immunogenic Gal$\alpha$(1,3)Gal epitope, presents an additional hurdle to overcome in the quest for the production of immuno-tolerable xenotransplants.

Keusch J J et al have previously reported the cloning of the rat iGb3 synthase gene (J.Biol. Chem 2000). The gene is reported as GenBank sequence NM 138524.

PCT publication No. WO 02/081688 to The Austin Research Institute discloses a partial cDNA sequence encoding a portion of exon 5 (480 base pairs) of the porcine iGb3 synthase gene. This application also purports to cover the use of this DNA sequence to disrupt this gene in cells, tissues and organs for xenotransplantation.

It is an object of the present invention to provide genomic and regulatory sequences of the porcine iGb3 synthase gene.

It is an additional object of the present invention to provide cDNA sequences, as well as novel variants, of the porcine iGb3 synthase gene.

It is another object of this invention to provide novel nucleic acid and amino acid sequences that encode the porcine iGb3 synthase protein.

It is yet a further object of the present invention to provide cells, tissues and/or organs deficient in the porcine iGb3 synthase gene.

It is another object of the present invention to generate animals, particularly pigs, lacking a functional porcine iGb3 synthase gene.

It is yet a further object of the present invention to provide cells, tissues and/or organs deficient in functional porcine iGb3 synthase gene for use in xeontransplantation of non-human organs to human recipients in need thereof.

SUMMARY OF THE INVENTION cDNA, peptide sequences, and genomic organization of the porcine isogloboside 3 synthase gene have been determined. The present invention provides porcine isogloboside 3 (iGb3) synthase protein, cDNA, and genomic DNA regulatory sequences. Further, the present invention provides porcine animals, tissue and organs as well as cells and cell lines derived from such animals, tissue and organs, which lack expression of functional porcine iGb3 synthase. Such animals, tissues, organs and cells can be used in research and in medical therapy, including in xenotransplantation. In addition, methods are provided to prepare organs, tissues, and cells lacking the porcine iGb$_3$ synthase gene for use in xenotransplantation.

One embodiment of the present invention provides novel nucleic acid cDNA sequences of the porcine iGb3 synthase gene (Table 1, Seq. ID No. 1). Another embodiment of the present invention provides predicted peptide sequences of the porcine iGb3 synthase gene (Table 2, Seq. ID No. 2). Nucleotide and amino acid sequences at least 80, 85, 90, 95, 98 or 99% homologous to SEQ ID Nos. 1 or 2 are provided. In addition, nucleotide and peptide sequences that contain at least 500 contiguous nucleotides or 165 amino acids of SEQ ID Nos. I or 2 are also provided. Nucleotide and amino acid sequences containing at least SEQ ID Nos. 1 or 2 are also provided. Further provided is any nucleotide sequence that hybridizes, optionally under stringent conditions, to SEQ ID No 1, as well as, nucleotides homologous thereto.

Another embodiment of the present invention provides nucleic acid sequences representing genomic DNA of the porcine iGb3 synthase gene (Table 3, Seq. ID Nos. 3-10). Seq. ID Nos. 3-6 represent exons 2-5, respectively. Seq. ID No. 7 represent a partial sequence of intron 1, and Seq. ID Nos. 8-10 represent complete sequences of introns 2-4, respectively. Nucleotide sequences at least 80, 85, 90, 95, 98 or 99% homologous to SEQ ID Nos 3-10 are provided. In addition, nucleotide and peptide sequences that contain at least 10, 15, 17, 20, 25 or 30 contiguous nucleotides of SEQ ID Nos. 3-10 are also provided. Further provided is any nucleotide sequence that hybridizes, optionally under stringent conditions, to SEQ ID No 3-10, as well as, nucleotides homologous thereto. Nucleic acid sequences containing at least SEQ ID Nos. 3-10 are also provided.

In another embodiment, the present invention provides nucleic acid sequences of the genomic DNA sequence of the porcine iGb3 synthase gene, represented by SEQ ID No. 11. SEQ ID No. 11 represents a contiguous genomic DNA sequence containing a portion of Intron 1, and the complete sequence of Exon 2, Intron 2, Exon 3, Intron 3, Exon 4, Intron 4, and Exon 5 (Table 4). In addition, nucleotide sequences that contain at least 10, 15, 17, 20, 25, 30, 50, 100, 500, 650, 750, 1000, or 5000 contiguous nucleotides of SEQ ID NO. 11 are provided, as well as nucleotide sequences at least 80, 85, 90, 95, 98, or 99% homologous to SEQ ID NO. 11.

In still another embodiment, the invention provides genomic DNA sequence of the porcine iGb3 synthase gene as represented by SEQ ID. No. 12 (Table 5). SEQ ID No, 12 represents a contiguous genomic DNA sequence containing a portion of Intron 1, and the complete sequence of Exon 2, Intron 2, Exon 3, Intron 3, Exon 4, Intron 4, and a partial sequence of Exon 5. In addition, nucleotide sequences that contain at least 10, 15, 17, 20, 25, 30, 50, 100, 500, 650, 750, 1000, or 5000 contiguous nucleotides of SEQ ID NO. 12 are provided, as well as nucleotide sequences at least 80, 85, 90, 95, 98, or 99% homologous to SEQ ID NO. 12.

In still another embodiment, the invention provides a partial genomic DNA sequence of the porcine iGb3 synthase gene as represented by SEQ ID. No. 13 (Table 6). SEQ ID No, 13 represents a contiguous genomic sequence containing sequence of Exon 5. In addition, nucleotide sequences that contain at least 10, 15, 17, 20, 25, 30, 50, 100, or 300 contiguous nucleotides of SEQ ID NO. 13 are provided, as well as nucleotide sequences at least 80, 85, 90, 95, 98, or 99% homologous to SEQ ID NO. 13.

In further embodiments, nucleotide and amino acid sequences at least 80, 85, 90, 95, 98 or 99% homologous to SEQ ID Nos 1, 2, 3-10, 11, 12, and 13 are provided. In addition, nucleotide and peptide sequences that contain at least 10, 15, 17, 20, 25, 30, 50, 100, 150, 200, 300, 400, 500, 650, 750, 800, or 1000 contiguous nucleotide or amino acid sequences of SEQ ID Nos 1, 2, 3-10, 11, 12, and 13 are also provided. Further provided is any nucleotide sequence that hybridizes, optionally under stringent conditions, to SEQ ID Nos 1, 2, 3-10, 11, 12, and 13, as well as nucleotides homologous thereto.

Another aspect of the present invention provides nucleic acid constructs that contain cDNA or variants thereof encoding porcine iGb3 synthase. These cDNA sequences can be derived from Seq ID Nos. 1, 2, 3-10, 11, 12, and 13 or any fragment thereof. Constructs can contain one, or more than one, internal ribosome entry site (IRES). The construct can also contain a promoter operably linked to the nucleic acid sequence encoding porcineiGb3 synthase, or, alternatively, the construct can be promoterless.

In another embodiment, nucleic acid constructs are provided that contain nucleic acid sequences that permit random or targeted insertion into a host genome. The nucleic acid sequences can be derived from Seq ID Nos. 1, 2, 3-10, 11, 12, and 13, or any fragment thereof. In addition to the nucleic acid sequences the expression vector can contain selectable marker sequences, such as, for example, enhanced Green Fluorescent Protein (eGFP) gene sequences, initiation and/or enhancer sequences, poly A-tail sequences, and/or nucleic acid sequences that provide for the expression of the construct in prokaryotic and/or eukaryotic host cells.

In another embodiment, nucleic acid targeting vectors constructs are also provided wherein homologous recombination in somatic cells can be achieved. These targeting vectors can be transformed into mammalian cells to target the porcine iGb3 synthase gene via homologous recombination. In one embodiment, the targeting vectors can contain a 3' recombination arm and a 5' recombination arm that is homologous to the genomic sequence of the porcine iGb3 synthase gene. The homologous DNA sequence can include at least 15 base pair (bp), 20 bp, 25 bp, 50 bp, 100 bp, 500 bp, 1 kbp (kilobase pair), 2 kbp, 4 kbp, 5 kbp, 10 kbp, 15 kbp, 20 kbp, or 50 kbp of sequence homologous to the porcine iGb3 synthase gene sequence. In another embodiment, the homologous DNA sequence can include one or more intron and/or exon sequences.

Another embodiment of the present invention provides oligonucleotide primers capable of hybridizing to porcine iGb3 synthase cDNA or genomic sequence, such as Seq ID Nos. 1, 3-10, 11, 12, or 13. In a preferred embodiment, the primers hybridize under stringent conditions to SEQ ID Nos. 1, 3-10, 11, 12 or 13. Another embodiment provides oligonucleotide probes capable of hybridizing to porcine iGb3 synthase nucleic acid sequences, such as SEQ ID Nos. 1, 3-10, 11, 12, or 13. The polynucleotide primers or probes can have at least 14 bases, 20 bases, preferably 30 bases, or 50 bases which hybridize to a polynucleotide of the present invention. The probe or primer can be at least 14 nucleotides in length, and in a preferred embodiment, are at least 15, 20, 25, 28, or 30 nucleotides in length.

In another aspect of the present invention, mammalian cells lacking at least one allele of the porcine iGb3 synthase gene produced according to the process, sequences and/or constructs described herein are provided. These cells can be obtained as a result of homologous recombination. Particularly, by inactivating at least one allele of the porcine iGb3 synthase gene, cells can be produced which have reduced capability for expression of functional porcine iGb3 synthase protein.

In embodiments of the present invention, alleles of the porcine iGb3 synthase gene are rendered inactive according to the process, sequences and/or constructs described herein, such that the resultant porcine iGb3 synthase is no longer generated, this reducing the ability to produce the Galα(1,3)Gal epitope. In one embodiment, the porcine iGb3 synthase gene can be transcribed into RNA, but not translated into protein. In another embodiment, the porcine iGb3 synthase gene can be transcribed in an inactive truncated form. Such a truncated RNA may either not be translated or can be translated into a nonfunctional protein. In an alternative embodiment, the porcine iGb3 synthase gene can be inactivated in such a way that no transcription of the gene occurs. In a further embodiment, the porcine iGb3 synthase gene can be transcribed and then translated into a nonfunctional protein.

In a further aspect of the present invention, porcine animals are provided in which at least one allele of the porcine iGb3 synthase gene is inactivated via a genetic targeting event produced according to the process, sequences and/or constructs described herein. In another aspect of the present invention, porcine animals are provided in which both alleles of the porcine iGb3 synthase gene are inactivated via a genetic targeting event. The gene can be targeted via homologous recombination. In other embodiments, the gene can be disrupted, i.e. a portion of the genetic code can be altered, thereby affecting transcription and/or translation of that segment of the gene. For example, disruption of a gene can occur through substitution, deletion ("knock-out") or insertion ("knock-in") techniques. Additional genes for a desired protein or regulatory sequence that modulate transcription of an existing sequence can be inserted.

In another aspect of the present invention, porcine cells lacking one allele, optionally both alleles of the porcine iGb3 synthase gene can be used as donor cells for nuclear transfer into enucleated oocytes to produce cloned, transgenic animals. Alternatively, porcine iGb3 synthase knockouts can be created in embryonic stem cells, which are then used to produce offspring. Offspring lacking a single allele of the functional iGb3 synthase gene produced according to the process, sequences and/or constructs described herein can be breed to further produce offspring lacking functionality in both alleles through mendelian type inheritance. Cells, tissues and/or organs can be harvested from these animals for use in xenotransplantation strategies. The elimination of a functional iGb3 synthase protein may reduce the immune rejection of the transplanted cell, tissue or organ due to the reduced amount of immunogenic Galα(1,3)Gal epitope present in the cell In one aspect of the present invention, a pig can be prepared by a method in accordance with any aspect of the present invention. Genetically modified pigs can be used as a source of tissue and/or organs for transplantation therapy. A pig embryo prepared in this manner or a cell line developed therefrom can also be used in cell-transplantation therapy. Accordingly, there is provided in a further aspect of the invention a method of therapy comprising the administration of genetically modified cells lacking porcine iGb3 synthase to a patient, wherein the cells have been prepared from an embryo or animal lacking the porcine iGb3 synthase gene. This aspect of the invention extends to the use of such cells in medicine, e.g. cell-transplantation therapy, and also to the use of cells derived from such embryos in the preparation of a cell or tissue graft for transplantation. The cells can be organized into tissues or organs, for example, heart, lung, liver, kidney, pancreas, corneas, nervous (e.g. brain, central nervous system, spinal cord), skin, or the cells can be islet cells, blood cells (e.g. haemocytes, i.e. red blood cells, leucocytes) or haematopoietic stem cells or other stem cells (e.g. bone marrow).

In another aspect of the present invention, porcine iGb3 synthase-deficient pigs also lack genes encoding other xenoantigens. In one embodiment, porcine cells are provided that lack the α1,3 galactosyltransferase gene, such as described in Phelps, et al., Science, 299: pp. 411-414 (2003) or WO 2004/028243, and the porcine iGb3 synthase gene produced according to the process, sequences and/or constructs described herein. In another embodiment, porcine α1,3 galactosyltransferase gene knockout cells are further modified to knockout the porcine iGb3 synthase gene produced according to the process, sequences and/or constructs described herein. In another embodiment, porcine cells are provided that lack the CMP-Neu5Ac hydroxylase gene (see, for example, U.S. Ser. No. 10/863,116), and/or the Forssman synthase gene (see, for example, U.S. patent application Ser. No. 60/568,922), and/or the porcine invariant chain (see, for example, U.S. Ser. No. 10/947,920), and the iGb3 synthase gene. In addition, porcine iGb3 synthase-deficient pigs produced according to the process, sequences and/or constructs described herein, optionally lacking one or more additional genes associated with an adverse immune response, can be modified to express complement inhibiting proteins, such as, for example, CD59, DAF, and/or MCP can be further modified to eliminate the expression of al least one allele of the porcine iGb3 synthase gene. These animals can be used as a source of tissue and/or organs for transplantation therapy. A pig embryo prepared in this manner or a cell line developed therefrom can also be used in cell-transplantation therapy.

DETAILED DESCRIPTION OF THE INVENTION

Elimination of the iGb3 synthase gene can reduce a pig organ's immunogenicity by reducing the expression of the highly immunogenic Galα(1,3)Gal epitope and thus removing an immunological barrier to xenotransplantation. The present invention is directed to novel nucleic acid sequences encoding cDNA and peptides of the porcine iGb3 synthase. Information about the genomic organization, and intronic sequences of the gene are also provided. In one aspect, the invention provides isolated and substantially purified cDNA molecules having Seq. ID No. 1, or a fragment thereof. In another aspect of the invention, predicted amino acid sequences having Seq. ID No. 2, or a fragment thereof, are provided. In another aspect of the invention, DNA sequences comprising genomic DNA of the iGb3 synthase gene are provided in Seq. ID Nos. 3-10, 11, 12, and 13, or a fragment thereof. In another aspect, primers for amplifying porcine iGb3 synthase cDNA or genomic sequence derived from Seq. ID Nos. 1, 3-10, 11, 12, or 13 are provided. Additionally, probes for identifying iGb3 synthase nucleic acid sequence derived from Seq. ID Nos. 1, 3-10, 11, 12, or 13 are provided. DNA represented by Seq. ID No. 3-10, 11, 12, or 13 can be used to construct pigs lacking functional iGb3 synthase genes. Thus, the invention also provides a porcine chromosome lacking a functional iGb3 synthase gene and a transgenic pig lacking a functional iGb3 synthase protein. Such pigs can be used as tissue sources for xenotransplantation into humans. In an alternate embodiment, iGb3 synthase-deficient pigs also lack genes encoding other genes associated with adverse immune responses in xenotransplantation, such as, for example, the α1,3galactosyltransferase gene, the CMP-NeuAc hydroxylase gene, the Forssman synthase gene, or the porcine invariant chain gene. In another embodiment, pigs lacking iGb3 synthase and other genes associated with adverse immune responses in xenotransplantation express complement inhibiting factors such as, for example, CD59, DAF, and/or MCP.

BRIEF DESCRIPTION OF THE FIGURES

FIG. 2 depicts a cDNA sequence of the porcine iGb3 synthase gene (SEQ ID No: 1)

FIG. 3 depicts an amino acid sequence of the porcine iGb3 synthase protein(SEQ ID No: 2).

DETAILED DESCRIPTION

Figure 1:
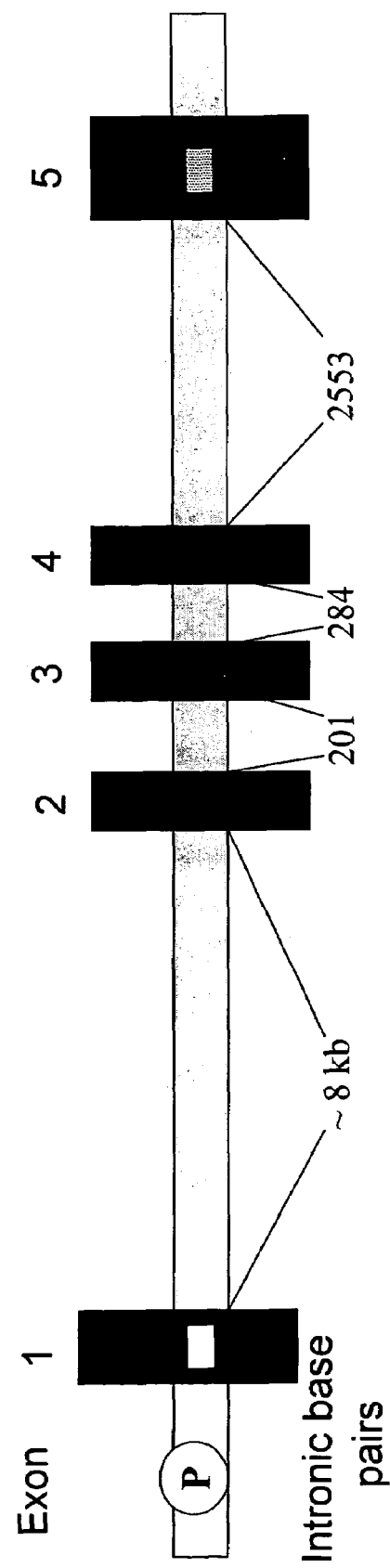
FIG. 1 provides the predicted deciphered genomic organization of the porcine iGb3 synthase gene and DNA sequencing. Shaded bars depict each numbered exon. The length of the introns between the exons is indicated across the bottom axis labeled base pairs. The predicted promoter region of the gene is depicted by an encircled letter P. The predicted location of the start codon is illustrated by a non shaded box contained within exon 1. The stop codon TAG is depicted by a patterned box within exon 5.

Definitions.

In order to more clearly and concisely describe and disclose the subject matter of the claimed invention, the following definitions are provided for specific terms used in the specification.

A "target DNA sequence" is a DNA sequence to be modified by homologous recombination. The target DNA can be in any organelle of the animal cell including the nucleus and mitochondria and can be an intact gene, an exon or intron, a regulatory sequence or any region between genes.

A "targeting DNA sequence" is a DNA sequence containing the desired sequence modifications and which is, except for the sequence modifications, substantially isogenic with the target DNA.

A "homologous DNA sequence or homologous DNA" is a DNA sequence that is at least about 85%, 90%, 95%, 98% or 99% identical with a reference DNA sequence. A homologous sequence hybridizes under stringent conditions to the target sequence, stringent hybridization conditions include those that will allow hybridization occur if there is at least 85% and preferably at least 95% or 98% identity between the sequences.

The term "contiguous" is used herein in its standard meaning, i.e., substantially without interruption, or uninterrupted.

An "isogenic or substantially isogenic DNA sequence" is a DNA sequence that is identical to or nearly identical to a reference DNA sequence. The term "substantially isogenic" refers to DNA that is at least about 97-99% identical with the reference DNA sequence, and preferably at least about 99.5-99.9% identical with the reference DNA sequence, and in certain uses 100% identical with the reference DNA sequence.

"Homologous recombination" refers to the process of DNA recombination based on sequence homology.

"Gene targeting" refers to homologous recombination between two DNA sequences, one of which is located on a chromosome and the other of which is not.

"Non-homologous or random integration" refers to any process by which DNA is integrated into the genome that does not involve homologous recombination.

A "selectable marker gene" is a gene, the expression of which allows cells containing the gene to be identified. A selectable marker can be one that allows a cell to proliferate on a medium that prevents or slows the growth of cells without the gene. Examples include antibiotic resistance genes and genes which allow an organism to grow on a selected metabolite. Alternatively, the gene can facilitate visual screening of transformants by conferring on cells a phenotype that is easily identified. Such an identifiable phenotype can be, for example, the production of luminescence or the production of a colored compound, or the production of a detectable change in the medium surrounding the cell.

The term "porcine" refers to any pig species, including pig species such as Large White, Landrace, Meishan, Minipig.

The term "oocyte" describes the mature animal ovum which is the final product of oogenesis and also the precursor forms being the oogonium, the primary oocyte and the secondary oocyte respectively.

The term "fragment" means a portion or partial sequence of a nucleotide or peptide sequence.

DNA (deoxyribonucleic acid) sequences provided herein are represented by the bases adenine (A), thymine (T), cytosine (C), and guanine(G).

Amino acid sequences provided herein are represented by the following abbreviations:

| | |
|---|---|
| A | alanine |
| P | proline |
| B | aspartate or asparagine |
| Q | glutamine |
| C | cysteine |
| R | arginine |
| D | aspartate |
| S | serine |
| E | glutamate |
| T | threonine |

-continued

| | |
|---|---|
| F | phenylalanine |
| G | glycine |
| V | valine |
| H | histidine |
| W | tryptophan |
| I | isoleucine |
| Y | tyrosine |
| Z | glutamate or glutamine |
| K | lysine |
| L | leucine |
| M | methionine |
| N | asparagine |

"Transfection" refers to the introduction of DNA into a host cell. Most cells do not naturally take up DNA. Numerous methods of transfection are known to the ordinarily skilled artisan, for example, CaPO$_4$ and electroporation. (J. Sambrook, E. Fritsch, T. Maniatis, Molecular Cloning: A Laboratory Manual, Cold Spring Laboratory Press, 1989). Transformation of the host cell is the indicia of successful transfection.

"Stringent conditions" refer to conditions that (1) employ low ionic strength and high temperature for washing, for example, 0.015 M NaCl/0.0015 M sodium citrate/0.1% SDS at 50° C., or (2) employ during hybridization a denaturing agent such as, for example, formamide. One skilled in the art can determine and vary the stringency conditions appropriately to obtain a clear and detectable hybridization signal. For example, stringency can generally be reduced by increasing the salt content present during hybridization and washing, reducing the temperature, or a combination thereof. See, for example, Sambrook et al., Molecular Cloning: A Laboratory Manual, Cold Spring Harbour Laboratory Press, Cold Spring Harbour, N.Y., (1989).

I. cDNA Sequence of the Porcine iGB3 Synthase Gene

One aspect of the present invention provides novel nucleic acid partial cDNA sequences of the porcine iGb3 synthase gene (Table 1, Seq. ID No. 1). Another aspect of the present invention provides predicted partial peptide sequences of the porcine iGb3 synthase gene (Table 2, Seq. ID No. 2). The ATG start codon for the cDNA is predicted to be located within exon 1 of the genomic DNA sequence. This is based on NCBI Blast homology analysis with other species' genomic DNA sequences, such as mouse (Genbank accession number AL611983), rat (Genbank accession number AC094786), and human (Genbank accession number AL513327), and the results described herein which failed to identify a start codon in exon 2. The TAG stop codon is located 685 base pairs from the beginning of exon 5. Nucleic and amino acid sequences containing at least 90, 95, 98 or 99% homologous to Seq. ID Nos. 1 or 2 are provided. In addition, nucleotide and peptide sequences that contain at least 10, 15, 17, 20 or 25, 30, 40, 50, 75, 100, 150, 250, 350, 500, or 1000 contiguous nucleic or amino acids of Seq ID Nos 1 or 2 are also provided. Further provided are fragments, derivatives and analogs of Seq. ID Nos. 1 or 2. Fragments of Seq. ID Nos. 1 or 2 can include any contiguous nucleic acid or peptide sequence that includes at least about 10 bp, 15 bp, 17 bp, 20 bp, 50 bp, 100 bp, 500 bp, 1 kbp, 5 kbp or 10 kpb.

TABLE 1

PARTIAL cDNA SEQUENCE OF PORCINE IGB3 SYNTHASE

Seq. ID No. 1
Exons 2-5

GGCCTGGAAGAGAATCCTCTGGTGGTTGATCCTACTT

GCACTTGACCTCTTAGGGCTGCTCCTGTTTGGCCTCC

CTGCTGTCAGGCATCTGGAAGTCCTTGTCCCCGTGGG

TGTCTGCCCTTTGACCAGAACACCCCTGCTGGGAGAC

AACTCCACGGGTCCCCTGCATCCTTGGGCCCGGCCTG

AAGTCCTGACCTGCACCTCCTGGGGGGGCCCCATTAT

ATGGGACGGCACCTTCGACCCAGATGTGGCCCAGCAA

GAGGCTACCCAGCAGAACCTCACCATTGGCCTGACGG

TCTTTGCTGTGGGCAGGTACCTGGAGAAGTACCTGGC

ACACTTCCTGGAGACAGCAGAGCAGCACTTCATGGTG

GGCCAGTGCGTCGCGTACTACGTGTTCACCGAGCGCC

CTGCAGCCATGCCCGCCTGCTGCTGGGCCCCGACCG

TGGGCTACGGATGGAGCACTTGGCGCGTGAGCGGCGC

TGGCAGGACGTGTCCATGGCGCGCATGCGCGCGCTGC

ACCCGGCGCTCGGGGGCGCCTGGGCCACGGGCGTG

CTTCGTGTTCTGCATGGACGTGGATCAGCACTTCAGT

GGCGCCTTCGGGCCCGGAGGCGCTGGCCGAGTCGGTG

GCGCAGCTGCACGCCTGGCACTACCGCTGGCCGCGGT

GGCTGCTGCCCTTTGAGCGTGACACGCGCTCGGCCGC

CGTGCTGGGCCCGGGCGAGGGCGACCTCTACTACCAT

GCGGCCGTGTTCGGGGGCAGCGTGGCCGCGCTGCGGC

GTCTGACGGCGCACTGCGCCCGGGGCCTGCGGCGGGA

CCGCTCGCGCGGCCTAGAGGCGCGCTGGCACGACAAG

AGCCACCTCAATAAGTTCTTCTGGCTGCACAAGCCCA

CCAAGCTGCTGTCGCCTGAGTTTTGCTGGAGCCCCGA

TCTTGGCCGCTGGGCTGAGATCCACTGCCCGCGCCTG

CTCTGGGCGCCCAAGGAGTATGCCCTGCTGCAAAGCT

AGCAATGCCGGTGAGGGCCCTTCTGGAAGCAGCGGGG

CACTGGGGGTGGGGGAGACTGCGTGAACGCCTCCCC

CGCTGCGGCATGGCTGCAGGAAGCTGGGCCTTTGGGA

CGTGGCTCCCGGAGGAGGATGAGCCATCCCTTTCCAT

CGAGACCCGGGCACCTCCAGCTGCCTGGAGACCATTC

ACCTCTGACCTTACTGAGTTCAGCGGAGGCCCTCTGA

AGAGATGTTTTAGCCCCTTCCCCATATCCCCTACGCT

TTATATGGTACTGAGGCGCCAAAAGGGAACATGATGG

CCCGAGGACCCAGAGGATCTATGAGTCAGCCTGTGAG

GTCAGCAGCTGGAGAGCAAGACTGACCCTCAGGCCAA

TABLE 1-continued

PARTIAL cDNA SEQUENCE OF PORCINE IGB3 SYNTHASE

ATACATCTGCTTCTAGGCACAAGCCCCAGATGAAGAA

ACTCAGTGGCATCCGGTTCCCTGACTTTGCTGGTT

TABLE 2

PREDICTED PARTIAL AMINO ACID SEQUENCE FOR PORCINE IGB3 SYHTASE

AWKRILWWLILLALDLLGLLLFGLPAVRHLEVLVPVG  Seq. ID No. 2

VCPLTRTPLLGDNSTGPLHPWARPEVLTCTSWGGPII

WDGTFDPDVAQQEATQQNLTIGLTVFAVGRYLEKYLA

HFLETAEQHFMVGQCVAYYVFTERPAAMPRLLLGPDR

GLRMEHLARERRWQDVSMARMRALHPALGGRLGHGAC

FVFCMDVDQHFSGAFGPEALAESVAQLHAWHYRWPRW

LLPFERDTRSAAVLGPGEGDLYYHAAVFGGSVAALRR

LTAHCARGLRRDRSRGLEARWHDKSHLNKFFWLHKPT

KLLSPEFCWSPDLGRWAEIHCPRLLWAPKEYALLQS

In other aspects of the present invention, nucleic acid constructs are provided that contain cDNA or variants thereof encoding porcine iGb3 synthase. These cDNA sequences can be SEQ ID NO 1, or derived from SEQ ID No. 2, or any fragment thereof. Constructs can contain one, or more than one, internal ribosome entry site (IRES). The construct can also contain a promoter operably linked to the nucleic acid sequence encoding porcine iGb3 synthase, or, alternatively, the construct can be promoterless. In another embodiment, nucleic acid constructs are provided that contain nucleic acid sequences that permit random or targeted insertion into a host genome. In addition to the nucleic acid sequences the expression vector can contain selectable marker sequences, such as, for example, enhanced Green Fluorescent Protein (eGFP) gene sequences, initiation and/or enhancer sequences, poly A-tail sequences, and/or nucleic acid sequences that provide for the expression of the construct in prokaryotic and/or eukaryotic host cells. Suitable vectors and selectable markers are described below. The expression constructs can further contain sites for transcription initiation, termination, and/or ribosome binding sites. The constructs can be expressed in any prokaryotic or eukaryotic cell, including, but not limited to yeast cells, bacterial cells, such as *E. coli,* mammalian cells, such as CHO cells, and/or plant cells.

Promoters for use in such constructs, include, but are not limited to, the phage lambda PL promoter, *E. coli* lac, *E. coli* trp, *E. coli* phoA, *E. coli* tac promoters, SV40 early, SV40 late, retroviral LTRs, PGKI, GALI, GALIO genes, CYCI, PHO5, TRPI, ADHI, ADH2, forglymaldehyde phosphate dehydrogenase, hexokinase, pyruvate decarboxylase, phosphofructokinase, triose phosphate isomerase, phosphoglucose isomerase, glucokinase alpha-mating factor pheromone, PRBI, GUT2, GPDI promoter, metallothionein promoter, and/or mammalian viral promoters, such as those derived from adenovirus and vaccinia virus. Other promoters will be known to one skilled in the art.

II. Genomic Sequences of the Porcine iGB3 Synthase Gene

Nucleic acid sequences representing genomic DNA of the porcine iGb3 synthase gene (FIG. 1, Table 3, Table 4, Table 5, and Table 6) are also provided. Seq. ID Nos. 3-6 represent exons 2-5, respectively. Seq. ID No. 7 represents a partial sequence of intron 1. Seq. ID Nos. 8-10 represent the complete sequences of introns 2-4, respectively. Seq. ID No. 11 (Table 4) represents the contiguous region of a part of Intron 1, and the complete sequence of Exon 2, Intron 2, Exon 3, Intron 3, Exon 4, Intron 4, and Exon 5. Seq. ID No. 12 (Table 5) represents the contiguous region of a part of Intron 1, and the complete sequence of Exon 2, Intron 2, Exon 3, Intron 3, Exon 4, Intron 4, and the 5' portion of Exon 5. Seq. ID No. 13 (Table 6) represents the contiguous region of a portion of Exon 5. Nucleic and amino acid sequences at least 90, 95, 98 or 99% homologous to Seq. ID Nos. 3-10, 11, 12 and 13 are provided. Nucleic and amino acid sequences that contain at least Seq. ID Nos. 11 or 12 are also provided. In addition, nucleotide and peptide sequences that contain at least 10, 15, 17, 20, 25, 50, 100, 150, 200, 250, 300, 350, 400, 450, 500, 550, 600, 650, 750, 850, 1000, 2000, 2500, 3000, 3500, 4000, 4500, 5,000, or 5300 contiguous nucleic acids of Seq. ID Nos. 3-10, 11, 12, or 13 are also provided. Further provided are fragments, derivatives and analogs of Seq. ID Nos. 3-10, 11, 12, or 13. Fragments of Seq. ID Nos. 3-10, 11, 12, or 13 can include any contiguous nucleic acid or peptide sequence that includes at least about 10 bp, 15 bp, 17 bp, 20 bp, 50 bp, 100 bp, 500 bp, 1 kbp, 5 kbp or 10 kpb.

TABLE 3

GENOMIC SEQUENCE OF PORCINE IGB3 SYNTHASE GENE ccttgttctaaccctttagcagggattaactcaacatccaggacagccctccaaagtagg  Intron 1 Seq. ID No. 7 tgttcttaggacccacctttctagatgaggaaactcaggtgcggaggtccagaaccttgc ctgaggtcagacagctaagaagtggtggcctgggattcgaacccaggggtcttgctcca gcagtcttgcttctcaccctaggggtccagtctgtctagaaacaccagcacccagcaggg gtgaggagagatggaagagatcccccagaggagcttattcaaattcttcattttgggc ccttctggaaaacagccaaccacgctccaatcctaaagtactcctcctctgagccagcaa agggctggtacctctgctggaggtacctggcttggggactaagagccaccatagacaca gagtccctgagcacaggtggccctccgtgcagcccagcaatgcatctctaagccccagag TABLE 3-continued

GENOMIC SEQUENCE OF PORCINE IGB3 SYNTHASE GENE agctctcaactcctagcttccaagccacaaacttccctgcatccctctcagactctcccc tgcccaaggtcagtcctacacactgcctggacgaagcgcccacccctaatggttactg tcacttgagtgtgcctactgggaaaagcaaagaattaaacatctaaatgctcatcaaaag ggacctgggtgaggtaaagtgatgcccctcccgtcaatggcatgttaggcagctggaaa aaggggtgaggaagcgcttcaaaaataggaagttccccattgtggctcaggggggaaacaa accccgccttgtacccccatgaggatacgggttcgatccccggcctcgctcagtgggttaa ggatccggtgtcgctgtgagctgcagtgtcagttgcaggcatggctcgagtcctgcgttg ccgtggctggggcataggccagcagctgcagctctgatttagcccctagcctgggaacct ccacatgccataggtgcggccctaaaaagcaaaaaaaaaaaaaaaaaaaagagagagag agagagagatggaataaactcaaagacataatggtcagtggaaaatacaaggcaagga agagcatatcagcaggctaccgtgtgtgggaggaaaagcacaggaagagaaggagagagc gcatttgctaccgtatttacatttgcctgcatatacacgactgtccccatgcagaggaac aggaaagactgcactgtctatactctctaggaccttttgaatgtctgccatgtgcacagag taatatattcatagtcaaagcaaataaaatgaaacattaaattatatactttcccatata tatgtatatgtggaaattacacacacacacatatattttgtgttgctaatgtccct ccctactccccgcccacccag

| | | |
|---|---|---|
| GGCCTGGAAGAGAATCCTCTGGTGGTTGATCCTACTTGCACTTGACCTCTTAGGGCTGCT CCTGTTTGGCCTCCCTGCTGTCAG | Exon 2 | Seq. ID No. 3 |
| gtacaaccccccttcccctagtgctcaagatgggaccagcaggggagggttaaagtggctc tttcccagtgcctccttaagggatagagagtgctggctctctcctgcacaagtgtccttg cgggctctccccccttgtaaggagcaaagccacagggctcctgagcaggctgacacccctc actgctgcccccatcccccag | Intron 2 | Seq. ID No. 8 |
| GCATCTGGAAGTCCTTGTCCCCGTGGGTGTCTGCCCTTTGACCAGAACACCCCTGCTGGG AGACAACTCCACGGGTCCCCTGCATCCTTG | Exon 3 | Seq. ID No. 4 |
| gtaaggagctgccatctccaggatctctgggcctccagcaccccaccccccaagtccctgc cctcctcgcatcccccaccctggcagggctaggcgctccaccccagggcccccagcaggtt acacatctcgaaatacccctgctggatctggggtagagagttctagggcagggcctgggtg tgacccacttgcaagtccctggggcccaggcctggggaggtgacagtgaccacgcacgaa gcaggtggataatggacgaatccctccatccctgccctggctag | Intron 3 | Seq. ID No. 9 |
| GGCCCGGCCTGAAGTCCTGACCTGCACCTCCTGGGGGGGCCCCATTATATGGGACGGCAC CTTCGACCCAGATGTGGCCCAGCAAGAGGCTACCCAGCAGAACCTCACCATTGGCCTGAC GGTCTTTGCTGTGGGCAG | Exon 4 | Seq. ID No. 5 |
| gtaaggcctgggaggcgagcagtgctgtccaagcgaagggttgggaggggcgtgcatgtg aagcagggcgtggggtgccccattctccggggccacagcatcccaagcggaagcagaagg caaagacagcacctcctgggcaagactccaagggtgaggcaggaccgaccccctccttccc ttcctccctggacaccagcaccatggagcccagccagcgcaggcagccgggggctcagga ccatgtcctggaaggaacctggctagtggtgagaaaacaatggagttttttcaggcgaaag tgagaagaggtgagaactgggtaagtagaggggatgacccagctgcagtgagcgccccgc ccccatggaggtcagtggctcaggcgcaggttagggagggaggaagattcaccaagcaag | Intron 4 | Seq. ID No. 10 |

TABLE 3-continued

GENOMIC SEQUENCE OF PORCINE IGB3 SYNTHASE GENE

```
tctgatggtgggactggggccgggggacggagggctcttgcaagggagtggatctgggct
gagtaaagagaaacgtgaagaaatggggatgcaacagtaacgaacctgactaggacccat
gaggacccgggttcaatccctggcctcgctcagtgggttaaggatccagcgttgccgtga
ctgtggagtagtcgcagacatggttcggatcccgagttgctgtggctgtggcgtaggtgg
gcagttgcagctccagcctgaccoctagactgggaacttccatatgccgggggtgcgccc
ccccaaaaaagaaaggggagtgttgagagtggcagggtcagcaggccagagggctcagt
gagggaggactatggggggtggtatcaggaagcgggctggaaggacggggctgctgaggg
ggacgagtgaggccgcagtttgggagggaaggcagactgatgatgagcaagctgagggag
aggtcatggggcaggtggctcaggagagggaaggacagactctctccaggagaggaggc
caatcgaggaagtgagaggcccccaggtatggaggaggaacctggaatggtaggtggaga
actcacaagggtgctggtctccccatctcccgattagggatggcgggggggtccaagctgg
gtactcactttccagtagtgatgcaaatgggactcctggctgagagtggcacttagatcc
tatagtcctaaggctcagagaggtagagttcaggacaatttaagggagcgtttaataatg
gaagaagctgctttcgggaggcagtaaaaagctttgcatcccggaaaagatatccaaaag
tatctgatgaattcagctcctccaaatgactcctctctgtccctcacaccctagacggga
gaaagccaggaggaccoctgggaggccagggtgcaaagaggaccaaggtggacggaactg
ctggcctctccagggccttgatgtccccacttccgttctggatgctgagtagggtgttcc
cataccagccctctgggtccagaaattccagagtcttgagatccaaattccaaggttcta
tgagtccaacactctgggatgctgaggcttccaaggtctctcattccagttttcacagtt
ccaccaggaatagaacaagtgcaggtaaagctatgggctccactgccaagcagggttcaa
atcctggcttcatacctaccagctgtgtgcgagggtgcatgagttcctaaagctcttgga
gactgtttcctcaccaggaaacggaactaataatggtgaggattaaatgagataatacac
attactttgaacactctcacatgataaatgttcaaaaagatcaggcattattattattat
tttagaaccttaggatcccaaagtctgttcatacagtttccagtattctggatgtctcga
ttatctgtgtaaggaatcactacaaacgcagtagctgaaggcagttcactattatcatag
ctcatgactttgtggctcaagaattccgactgctcagcagcaaaggttcatcacttctct
caaacagctgggtctcctgtgagacagccgcctgaggaagactggcagggtgcctctcca
tggctagcttgggttctctcactctgtggcagtatcggagttccaggacttcttatgcga
agggtcagagctctaaagggacagaggctaacgcgcgggtcttcccaaggcccagcatgg
catcccttccttgtgcctctattgatcaaaggggtccgggagagccgagttcaagggaag
ggacacaggggctctaggggcagggctggcaaacaatggacaattgttatgattattatt
taccacaccttccgcatgaggaagttcttgggccaggattccaacccaggccagggatca
aacccgtgacccaagccacagtagtaacaacgccagatccttaacttgctgagccaccaa
ggaactccaattggcaattaatttaatttgcctccaacggggactgcccttccggagt
tcctgggcctggggtcgcagggtcaccagaacggacatgggggcggctgggaagggcgca
gtgaccagctgactcggacggcccgctccgcag
GTACCTGGAGAAGTACCTGGCACACTTCCTGGAGACAGCAGAGCAGCACTTCATGGTGGG    Exon 5   Seq. ID No. 6
CCAGTGCGTCGCGTACTACGTGTTCACCGAGCGCCCTGCAGCCATGCCCCGCCTGCTGCT
```

TABLE 3-continued

GENOMIC SEQUENCE OF PORCINE IGB3 SYNTHASE GENE

GGGCCCCGACCGTGGGCTACGGATGGAGCACTTGGCGCGTGAGCGGCGCTGGCAGGACGT

GTCCATGGCGCGCATGCGCGCGCTGCACCCGGCGCTCGGGGGGCGCCTGGGCCACGGGGC

GTGCTTCGTGTTCTGCATGGACGTGGATCAGCACTTCAGTGGCGCCTTCGGGCCCGAGGC

GCTGGCCGAGTCGGTGGCGCAGCTGCACGCCTGGCACTACCGCTGGCCGCGGTGGCTGCT

GCCCTTTGAGCGTGACACGCGCTCGGCCGCCGTGCTGGGCCCGGGCGAGGGCGACCTCTA

CTACCATGCGGCCGTGTTCGGGGGCAGCGTGGCCGCGCTGCGGCGTCTGACGGCGCACTG

CGCCCGGGGCCTGCGGCGGGACCGCTCGCGCGGCCTAGAGGGCGCGCTGGCACGACAAGAG

CCACCTCAATAAGTTCTTCTGGCTGCACAAGCCCACCAAGCTGCTGTCGCCTGAGTTTTG

CTGGAGCCCGATCTTGGCCGCTGGGCTGAGATCCACTGCCCGCGCCTGCTCTGGGCGCC

CAAGGAGTATGCCCTGCTGCAAAGCTAGCAATGCCGGTGAGGGCCCTTCTGGAAGCAGCG

GGGCACTGGGGTGGGGGGAGACTGCGTGAACGCCTCCCCCGCTGCGGCATGGCTGCAGG

AAGCTGGGCCTTTGGGACGTGGCTCCCGGAGGAGGATGAGCCATCCCTTTCCATCGAGAC

CCGGGCACCTCCAGCTGCCTGGAGACCATTCACCTCTGACCTTACTGAGTTCAGCGGAGG

CCCTCTGAAGAGATGTTTTAGCCCCTTCCCCATATCCCCTACGCTTTATATGGTACTGAG

GCGCCAAAAGGGAACATGATGGCCCGAGGACCCAGAGGATCTATGAGTCAGCCTGTGAGG

TCAGCAGCTGGAGAGCAAGACTGACCCTCAGGCCAAATACATCTGCTTCTAGGCACAAGC

CCCAGATGAAGAAACTCAGTGGCATCCGGTTCCCTGACTTTGCTGGTT

TABLE 4

GENOMIC SEQUENCE OF PORCINE IGB3 SYNTHASE GENE

| | |
|---|---|
| ccttgttctaacccttttagcagggattaactcaacatccaggacagccctccaaagtagg | Partial Seq. ID. No. 11 |
| tgttcttaggacccacctttctagatgaggaaactcaggtgcggaggtccagaaccttgc | Intron 1, |
| ctgaggtcagacagctaagaagtggtggcctgggattcgaacccaggggtcttgctcca | Exon 2, |
| gcagtcttgcttctcaccctaggggtccagtctgtctagaaacaccagcacccagcaggg | Intron 2, |
| gtgaggagagatggaagagatcccccagaggagcttattcaaattcttcattttttgggc | Exon 3, |
| ccttctggaaaacagccaaccacgctccaatcctaaagtactcctcctctgagccagcaa | Intron 3, |
| aggggctggtacctctgctggaggtacctggcttggggactaagagccaccatagacaca | Exon 4, |
| gagtccctgagcacaggtggccctccgtgcagcccagcaatgcatctctaagccccagag | Intron 4, |
| agctctcaactcctagcttccaagccacaaacttccctgcatccctctcagactctcccc | and |
| tgcccaaggtcagtcctacacactgcctggacgaagcgccccaccccctaatggttactg | Exon 5 |
| tcacttgagtgtgcctactgggaaaagcaaagaattaaacatctaaatgctcatcaaaag | |
| ggacctgggtgaggtaaagtgatgccccctcccgtcaatggcatgttaggcagctggaaa | |
| aaggggtgaggaagcgcttcaaaaataggaagttccccattgtggctcagggggaaacaa | |
| accccgccttgtacccatgaggatacgggttcgatccccggcctcgctcagtgggttaa | |
| ggatccggtgtcgctgtgagctgcagtgtcagttgcaggcatggctcgagtcctgcgttg | |
| ccgtggctggggcataggccagcagctgcagctctgatttagcccctagcctgggaacct | |
| ccacatgccataggtgcggccctaaaaagcaaaaaaaaaaaaaaaaaaagagagagag | |
| agagagagagatggaataaactcaaagacataatggtcagtggaaaatacaaggcaagga | |

TABLE 4-continued

GENOMIC SEQUENCE OF PORCINE IGB3 SYNTHASE GENE agagcatatcagcaggctaccgtgtgtgggaggaaaagcacaggaagagaaggagagagc gcatttgctaccgtatttacatttgcctgcatatacacgactgtccccatgcagaggaac aggaaagactgcactgtctatactctctaggacctttgaatgtctgccatgtgcacagag taatatattcatagtcaaagcaaataaaatgaaacattaaattatatactttcccatata tatgtatatgtggaaattacacacacacatatatattttgtgttgctaatgtccct ccctactccccgcccacccagGGCCTGGAAGAGAATCCTCTGGTGGTTGATCCTACTTGC ACTTGACCTCTTAGGGCTGCTCCTGTTTGGCCTCCCTGCTGTCAGgtacaaccccttcc cctagtgctcaagatgggaccagcaggggagggttaaagtggctctttcccagtgcctcc ttaagggatagagagtgctggctctctcctgcacaagtgtccttgcgggctctccccctt gtaaggagcaaagccacagggctcctgagcaggctgacacccctcactgctgcccccatc ccccagGCATCTGGAAGTCCTTGTCCCCGTGGGTGTCTGCCCTTTGACCAGAACACCCCT GCTGGGAGACAACTCCACGGGTCCCCTGCATCCTTGgtaaggagctgccatctccaggat ctctgggcctccagcacccccaccccccaagtccctgccctcctcgcatccccaccctggc agggctaggcgctccaccccagggccccagcaggttacacatctcgaaataccctgctgg atctggggtagagagttctagggcagggcctgggtgtgacccacttgcaagtccctgggg cccaggcctggggaggtgacagtgaccacgcacgaagcaggtggataatggacgaatccc tccatccctgccctggctagGGCCCGGCCTGAAGTCCTGACCTGCACCTCCTGGGGGGGC

CCCATTATATGGGACGGCACCTTCGACCCAGATGTGGCCCAGCAAGAGGCTACCCAGCAG

AACCTCACCATTGGCCTGACGGTCTTTGCTGTGGGGAGgtaaggcctgggaggcgagcag tgctgtccaagcgaagggttgggaggggcgtgcatgtgaagcagggcgtgggtgccca ttctccggggccacagcatcccaagcggaagcagaaggcaaagacagcacctcctgggca agactccaagggtgaggcaggaccgacccctccttcccttcctccctggacaccagcacc atggagcccagccagcgcaggcagccgggggctcaggaccatgtcctggaaggaacctgg ctagtggtgagaaaacaatggagtttttcaggcgaaagtgagaagaggtgagaactgggt aagtagaggggatgacccagctgcagtgagcgccccgccccatggaggtcagtggctca ggcgcaggttagggagggaggaagattcaccaagcaagtctgatggtgggactggggccg ggggacggagggctcttgcaagggagtggatctgggctgagtaaagagaaacgtgaagaa atggggatgcaacagtaacgaacctgactaggacccatgaggacccgggttcaatccctg gcctcgctcagtgggttaaggatccagcgttgccgtgactgtggagtagtcgcagacatg gttcggatcccgagttgctgtggctgtggcgtaggtgggcagttgcagctccagcctgac ccctagactggaacttccatatgccgggggtgcgccccccaaaaaaagaaaggggat gttgagagtggcagggtcagcaggccagagggctcagtgagggaggactatggggggtgg tatcaggaagcgggctggaaggacggggctgctgaggggacgagtgaggccgcagtttg ggagggaaggcagactgatgatgagcaagctgagggagaggtcatgggggcaggtggctc aggagagggaaggacagactctctccaggagaggaggccaatcgaggaagtgagaggccc ccaggtatggaggaggaacctggaatggtaggtggagaactcacaagggtgctggtctcc ccatctcccgattagggatggcgggggtccaagctgggtactcactttccagtagtgat gcaaatgggactcctggctgagagtggcacttagatcctatagtcctaaggctcagagag gtagagttcaggacaatttaagggagcgtttaataatggaagaagctgctttcgggaggc TABLE 4-continued

GENOMIC SEQUENCE OF PORCINE IGB3 SYNTHASE GENE agtaaaaagctttgcatcccggaaaagatatccaaaagtatctgatgaattcagctcctc caaatgactcctctctgtccctcacaccctagacgggagaaagccaggaggaccc ctggg aggccagggtgcaaagaggaccaaggtggacggaactgctggcctctccagggccttgat gtccccacttccgttctggatgctgagtagggtgttcccataccagccctctgggtccag aaattccagagtcttgagatccaaattccaaggttctatgagtccaacactctgggatgc tgaggcttccaaggtctctcattccagttttcacagttccaccaggaatagaacaagtgc aggtaaagctatgggctccactgccaagcagggttcaaatcctggcttcatacctaccag ctgtgtgcgagggtgcatgagttcctaaagctcttggagactgtttcctcaccaggaaac ggaactaataatggtgaggattaaatgagataatacacattactttgaacactctcacat gataaatgttcaaaaagatcaggcattattattattttta gaaccttaggatcccaaa gtctgttcatacagtttccagtattctggatgtctcgattatctgtgtaaggaatcacta caaacgcagtagctgaaggcagttcactattatcatagctcatgactttgtggctcaaga attccgactgctcagcagcaaaggttcatcacttctctcaaacagctgggtctcctgtga gacagccgcctgaggaagactggcagggtgcctctccatggctagcttgggttctctcac tctgtggcagtatcggagttccaggacttcttatgcgaagggtcagagctctaaagggac agaggctaacgcgcgggtcttcccaaggcccagcatggcatcccttccttgtgcctctat tgatcaaaggggtccgggagagccgagttcaagggaagggacacaggggctctaggggca gggctggcaaacaatggacaattgttatgattattatttaccacaccttccgcatgagga agttcttgggccaggattccaacccaggccagggatcaaacccgtgacccaagccacagt agtaacaacgccagatccttaacttgctgagccaccaaggaactccaattggcaattaat tttaatttgcctccaacggggactgcccttt ccggagttcctgggcctggggtcgcaggg tcaccagaacggacatgggggcggctgggaagggcgcagtgaccagctgactcggacggc ccgctccgcagGTACCTGGAGAAGTACCTGGCACACTTCCTGGAGACAGCAGAGCAGCAC

TTCATGGTGGGCCAGTGCGTCGCGTACTACGTGTTCACCGAGCGCCCTGCAGCCATGCCC

CGCCTGCTGCTGGGCCCCGACCGTGGGCTACGGATGGAGCACTTGGCGCGTGAGCGGCGC

TGGCAGGACGTGTCCATGGCGCGCATGCGCGCGCTGCACCCGGCGCTCGGGGGGCGCCTG

GGCCACGGGGCGTGCTTCGTGTTCTGCATGGACGTGGATCAGCACTTCAGTGGCGCCTTC

GGGCCCGAGGCGCTGGCCGAGTCGGTGGCGCAGCTGCACGCCTGGCACTACCGCTGGCCG

CGGTGGCTGCTGCCCTTTGAGCGTGACACGCGCTCGGCCGCCGTGCTGGGCCCGGGCGAG

GGCGACCTCTACTACCATGCGGCCGTGTTCGGGGGCAGCGTGGCCGCGCTGCGGCGTCTG

ACGGCGCACTGCGCCCGGGGCCTGCGGCGGGACCGCTCGCGCGGCCTAGAGGCGCGCTGG

CACGACAAGAGCCACCTCAATAAGTTCTTCTGGCTGCACAAGCCCACCAAGCTGCTGTCG

CCTGAGTTTTGCTGGAGCCCCGATCTTGGCCGCTGGGCTGAGATCCACTGCCCGCGCCTG

CTCTGGGCGCCCAAGGAGTATGCCCTGCTGCAAAGCTAGCAATGCCGGTGAGGGCCCTTC

TGGAAGCAGCGGGGCACTGGGGGTGGGGGGAGACTGCGTGAACGCCTCCCCCGCTGCGGC

ATGGCTGCAGGAAGCTGGGCCTTTGGGACGTGGCTCCCGGAGGAGGATGAGCCATCCCTT

TCCATCGAGACCCGGGCACCTCCAGCTGCCTGGAGACCATTGACGTCTGACCTTACTGAG

TTCAGCGGAGGCCCTCTGAAGAGATGTTTTAGCCCCTTCCCCATATCCCCTACGCTTTAT

TABLE 4-continued

GENOMIC SEQUENCE OF PORCINE IGB3 SYNTHASE GENE

ATGGTACTGAGGCGCCAAAAGGGAACATGATGGCCCGAGGACCCAGAGGATCTATGAGTC

AGCCTGTGAGGTCAGCAGCTGGAGAGCAAGACTGACCCTCAGGCCAAATACATCTGCTTC

TAGGCACAAGCCCCAGATGAAGAAACTCAGTGGCATCCGGTTCCCTGACTTTGCTGGTT

TABLE 5

GENOMIC SEQUENCE OF PORCINE IGB3 SYNTHASE GENE

| | |
|---|---|
| ccttgttctaaccctttagcagggattaactcaacatccaggacagccctccaaagtagg | Partial Seq. ID. No. 12 |
| tgttcttaggacccacctttctagatgaggaaactcaggtgcggaggtccagaaccttgc | Intron 1, |
| ctgaggtcagacagctaagaagtggtggcctgggattcgaacccagggggtcttgctcca | Exon 2, |
| gcagtcttgcttctcaccctaggggtccagtctgtctagaaacaccagcacccagcaggg | Intron 2, |
| gtgaggagagatggaagagatcccccagaggagcttattcaaattcttcattttttgggc | Exon 3, |
| ccttctggaaaacagccaaccacgctccaatcctaaagtactcctcctctgagccagcaa | Intron 3, |
| aggggctggtacctctgctggaggtacctggcttggggactaagagccaccatagacaca | Exon 4, |
| gagtccctgagcacaggtggccctccgtgcagcccagcaatgcatctctaagcccccagag | Intron 4, |
| agctctcaactcctagcttccaagccacaaacttccctgcatccctctcagactctcccc | and partial |
| tgcccaaggtcagtcctacacactgcctggacgaagcgcccaccccctaatggttactg | Exon 5 |
| tcacttgagtgtgcctactgggaaaagcaaagaattaaacatctaaatgctcatcaaaag | |
| ggacctgggtgaggtaaagtgatgcccctcccgtcaatggcatgttaggcagctggaaa | |
| aaggggtgaggaagcgcttcaaaaataggaagttccccattgtggctcaggggaaacaa | |
| accccgccttgtaccccatgaggatacgggttcgatccccggcctcgctcagtgggttaa | |
| ggatccggtgtcgctgtgagctgcagtgtcagttgcaggcatggctcgagtcctgcgttg | |
| ccgtggctggggcataggccagcagctgcagctctgatttagcccctagcctgggaacct | |
| ccacatgccataggtgcggccctaaaaagcaaaaaaaaaaaaaaaaaaaagagagagag | |
| agagagagatggaataaactcaaagacataatggtcagtggaaaatacaaggcaagga | |
| agagcatatcagcaggctaccgtgtgtgggaggaaaagcacaggaagagaaggagagagc | |
| gcatttgctaccgtatttacatttgcctgcatatacacgactgtccccatgcagaggaac | |
| aggaaagactgcactgtctatactctctaggaccttttgaatgtctgccatgtgcacagag | |
| taatatattcatagtcaaagcaaataaaatgaaacattaaattatatactttcccatata | |
| tatgtatatatgtggaaattacacacacacacatatatattttgtgttgctaatgtccct | |
| ccctactccccgcccacccagGGCCTGGAAGAGAATCCTCTGGTGGTTGATCCTACTTGC | |
| ACTTGACCTCTTAGGGCTGCTCCTGTTTGGCCTCCCTGCTGTCAGgtacaaccccttcc | |
| cctagtgctcaagatgggaccagcagggagggttaaagtggctctttcccagtgcctcc | |
| ttaagggatagagagtgctggctctctcctgcacaagtgtccttgcgggctctccccctt | |
| gtaaggagcaaagccacagggctcctgagcaggctgacacccctcactgctgccccatc | |
| ccccagGCATCTGGAAGTCCTTGTCCCCGTGGGTGTCTGCCCTTTGACCAGAACACCCCT | |
| GCTGGGAGACAACTCCACGGGTCCCCTGCATCCTTGgtaaggagctgccatctccaggat | |
| ctctgggcctccagcacccaccccccaagtccctgccctcctcgcatcccccaccctggc | |
| agggctaggcgctccaccccagggcccagcaggttacacatctcgaaatacccctgctgg | |

TABLE 5-continued

GENOMIC SEQUENCE OF PORCINE IGB3 SYNTHASE GENE

```
atctggggtagagagttctagggcagggcctgggtgtgacccacttgcaagtccctgggg
cccaggcctggggaggtgacagtgaccacgcacgaagcaggtggataatggacgaatccc
tccatccctgccctggctagGGCCCGGCCTGAAGTCCTGACCTGCACCTCCTGGGGGGGC
CCCATTATATGGGACGGCACCTTCGACCCAGATGTGGCCCAGCAAGAGGCTACCCAGCAG
AACCTCACCATTGGCCTGACGGTCTTTGCTGTGGGCAGgtaaggcctgggaggcgagcag
tgctgtccaagcgaagggttgggaggggcgtgcatgtgaagcagggcgtggggtgcccca
ttctccggggccacagcatcccaagcggaagcagaaggcaaagacagcacctcctgggca
agactccaagggtgaggcaggaccgacccctccttcccttcctccctggacaccagcacc
atggagcccagccagcgcaggcagccgggggctcaggaccatgtcctggaaggaacctgg
ctagtggtgagaaacaatggagttttttcaggcgaaagtgagaagaggtgagaactgggt
aagtagagggatgacccagctgcagtgagcgccccgcccccatggaggtcagtggctca
ggcgcaggttagggagggaggaagattcaccaagcaagtctgatggtgggactggggccg
ggggacggagggctcttgcaagggagtggatctgggctgagtaaagagaaacgtgaagaa
atggggatgcaacagtaacgaacctgactaggacccatgaggacccgggttcaatccctg
gcctcgctcagtgggttaaggatccagcgttgccgtgactgtggagtagtcgcagacatg
gttcggatcccgagttgctgtggctgtggcgtaggtgggcagttgcagctccagcctgac
ccctagactgggaacttccatatgccgggggtgcgccccccaaaaaaagaaaggggat
gttgagagtggcagggtcagcaggccagagggctcagtgagggaggactatgggggtgg
tatcaggaagcgggctggaaggacggggctgctgaggggacgagtgaggccgcagtttg
ggagggaaggcagactgatgatgagcaagctgagggagaggtcatgggggcaggtggctc
aggagagggaaggacagactctctccaggagaggaggccaatcgaggaagtgagaggccc
ccaggtatggaggaggaacctggaatggtaggtggagaactcacaagggtgctggtctcc
ccatctcccgattagggatggcggggggtccaagctgggtactcactttccagtagtgat
gcaaatgggactcctggctgagagtggcacttagatcctatagtcctaaggctcagagag
gtagagttcaggacaatttaagggagcgtttaataatggaagaagctgctttcgggaggc
agtaaaaagctttgcatcccggaaaagatatccaaaagtatctgatgaattcagctcctc
caaatgactcctctctgtccctcacaccctagacgggagaaagccaggaggaccccctggg
aggccagggtgcaaagaggaccaaggtggacggaactgctggcctctccagggccttgat
gtccccacttccgttctggatgctgagtagggtgttcccataccagccctctgggtccag
aaattccagagtcttgagatccaaattccaaggttctatgagtccaacactctgggatgc
tgaggcttccaaggtctctcattccagttttcacagttccaccaggaatagaacaagtgc
aggtaaagctatgggctccactgccaagcagggttcaaatcctggcttcatacctaccag
ctgtgtgcgagggtgcatgagttcctaaagctcttggagactgtttcctcaccaggaaac
ggaactaataatggtgaggattaaatgagataatacacattactttgaacactctcacat
gataaatgttcaaaagatcaggcattattattattattttagaaccttaggatcccaaa
gtctgttcatacagtttccagtattctggatgtctcgattatctgtgtaaggaatcacta
caaacgcagtagctgaaggcagttcactattatcatagctcatgactttgtggctcaaga
attccgactgctcagcagcaaaggttcatcacttctctcaaacagctgggtctcctgtga
gacagccgcctgaggaagactggcagggtgcctctccatggctagcttgggttctctcac
```

TABLE 5-continued

GENOMIC SEQUENCE OF PORCINE IGB3 SYNTHASE GENE tctgtggcagtatcggagttccaggacttcttatgcgaagggtcagagctctaaagggac agaggctaacgcgcgggtcttcccaaggcccagcatggcatcccttccttgtgcctctat tgatcaaaggggtccgggagagccgagttcaagggaagggacacaggggctctaggggca gggctggcaaacaatggacaattgttatgattattatttaccacaccttccgcatgagga agttcttgggccaggattccaacccaggccagggatcaaacccgtgacccaagccacagt agtaacaacgccagatccttaacttgctgagccaccaaggaactccaattggcaattaat tttaatttgcctccaacggggactgcccttttccggagttcctgggcctggggtcgcaggg tcaccagaacggacatgggggcggctgggaagggcgcagtgaccagctgactcggacggc ccgctccgcagGTACCTGGAGAAGTACCTGGCACACTTCCTGGAGACAGCAGAGCAGCAC

TTCATGGTGGGCCAGTGCGTCGCGTACTACGTGTTCACCGAGCGCCCTGCAGCCATGCCC

CGCCTGCTGCTGGGCCCCGACCGTGGGCTACGGATGGAGCACTTGGCGCGTGAGCGGCGC

TGGCAGGACGTGTCCATGGCGCGCATGCGCGCGCTGCACCCGGCGCTCGGGGGGCGCCTG

GGCCACGGGGCGTGCTTCGTGTTCTGCATGGACGTGGATCAGCACTTCAGTGGCGCCTTC

GGGCCCGAGGCGCTGGCCGAGTCGGTGGCGCAGCTGCACGCCTGGCACTACCGCTGGCCG

CGGTGGCTGCTGCCCTTTGAGCGTGACACGCGCTCGGCCGCCGTGCTGGGCCCGGGCGAG

GGCGACCTCTACTACCATGCGGCCGTGTTCGGGGGCAGCGTGGCCGCGCTGCGGCGTCTG

ACGGCGCACTGCGCCCGGGGCCTGCGGCGGGACCGCTCGCGCGGCCTAGAGGCGCGCTGG

CACGACAAGAGCCACCTCAATAAGTTCTTCTGGCTGCACAAGCCCACCAAGCTGCTGTCG

CCTGAGTTTTGCTGGAGCCCCGATCTTGGCCGCTGGGCTGAGATCCACTGCCCGCGCCTG

CTCTGGGCGCCCAAGGAGTATGCCCTGCTGCAAAGCTAGCAATGCCGGTGAGGGCCCTTC

TGGAAGCAGCGGGGCACTGGGGGTGGGGGGAGACTGCGTGAACGCCTCCCCCGCTGCGGC

ATGGCTGCAGGAAGCTGGGCCTTTGGGACGTGGCTCCCGGAGGAGGATGAGCCATCCCTT

TCCATCGAGACCCGGGCACCTCCAGCTGCCTGGAGACCATTCACCTCTGACCTTACTGAG

TTCAGCGGAGGCCCTCTGAAGAGATGTTTTAGCCCCTTCCCCATATCCCCTACGCTTTAT

ATGGTACTGAGGCGCCAAAAGGGAACATGATGGCCCGAGGACCCAGAGGATCTATGAGTC

AGCCTGTGAGGTCAGCAGCTGGAGAGCAAGACTGACCCTCAGGCCAAATACATCTGCTTC

TAGGCACAAGCCCCAGATGAAGAAACTCAGTGGCATCCGGTTCCCTGACTTTGCTGGTT

TABLE 6

GENOMIC SEQUENCE OF PORCINE IGB3 SYNTHASE GENE

Seq. ID No. 13 Partial

GACAAGAGCCACCTCAATAAGTTCTTCTGGCTGCACA

AGCCCACCAAGCTGCTGTCGCCTGAGTTTTGCTGGAG Exon 5

CCCCGATCTTGGCCGCTGGGCTGAGATCCACTGCCCG

CGCCTGCTCTGGGCGCCCAAGGAGTATGCCCTGCTGC

AAAGCTAGCAATGCCGGTGAGGGCCCTTCTGGAAGCA

GCGGGGCACTGGGGGTGGGGGGAGACTGCGTGAACGC

CTCCCCCGCTGCGGCATGGCTGCAGGAAGCTGGGCCT

TABLE 6-continued

GENOMIC SEQUENCE OF PORCINE IGB3 SYNTHASE GENE

TTGGGACGTGGCTCCCGGAGGAGGATGAGCCATCCCT

TTCCATCGAGACCCGGGCACCTCCAGCTGCCTGGAGA

CCATTCACCTCTGACCTTACTGAGTTCAGCGGAGGCC

CTCTGAAGAGATGTTTTAGCCCCTTCCCCATATCCCC

TACGCTTTATATGGTACTGAGGCGCCAAAAGGGAACA

TGATGGCCCGAGGACCCAGAGGATCTATGAGTCAGCC

TGTGAGGTCAGCAGCTGGAGAGCAAGACTGACCCTCA

TABLE 6-continued

GENOMIC SEQUENCE OF PORCINE IGB3 SYNTHASE GENE

GGCCAAATACATCTGCTTCTAGGCACAAGCCCCAGAT

GAAGAAACTCAGTGGCATCCGGTTCCCTGACTTTGCT

GGTT

III. Oligonucleotide Probes and Primers

The present invention further provides oligonucleotide probes and primers which hybridize to the hereinabove-described sequences (SEQ ID Nos. 1, 3-10, 11, 12, and 13). Oligonucleotides are provided that can be homologous to SEQ ID Nos. 1, 3-10, 11, 12, and 13, and fragments thereof. Oligonucleotides that hybridize under stringent conditions to SEQ ID Nos. 1, 3-10, 11, 12, and 13, and fragments thereof, are also provided. Stringent conditions can describe conditions under which hybridization will occur only if there is at least about 85%, about 90%, about 95%, or at least about 98% homology between the sequences. Alternatively, the oligonucleotide can have at least 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 75 or 100 bases which hybridize to SEQ ID Nos. 1, 3-10, 11, 12, and 13, and fragments thereof. Such oligonucleotides can be used as primers and probes to detect the sequences provided herein. The probe or primer can be at least 14 nucleotides in length, and in a preferred embodiment, are at least 15, 20, 25, 28, 30, or 35 nucleotides in length.

Given the above sequences, one of ordinary skill in the art using standard algorithms can construct oligonucleotide probes and primes that are complementary to sequences contained in Seq ID Nos. 1, 3-10, 11, 12, and 13, and fragments thereof. The rules for complementary pairing are well known: cytosine ("C") always pairs with guanine ("G") and thymine ("T") or uracil ("U") always pairs with adenine ("A"). It is recognized that it is not necessary for the primer or probe to be 100% complementary to the target nucleic acid sequence, as long as the primer or probe sufficiently hybridizes and can recognize the corresponding complementary sequence. A certain degree of pair mismatch can generally be tolerated.

Oligonucleotide sequences used as the hybridizing region of a primer can also be used as the hybridizing region of a probe. Suitability of a primer sequence for use as a probe depends on the hybridization characteristics of the primer. Similarly, an oligonucleotide used as a probe can be used as a primer.

It will be apparent to those skilled in the art that, provided with these specific embodiments, specific primers and probes can be prepared by, for example, the addition of nucleotides to either the 5' or 3' ends, which nucleotides are complementary to the target sequence or are not complimentary to the target sequence. So long as primer compositions serve as a point of initiation for extension on the target sequences, and so long as the primers and probes comprise at least 14 consecutive nucleotides contained within the above mentioned SEQ ID Nos. such compositions are within the scope of the invention.

The probes and primers herein can be selected by the following criteria, which are factors to be considered, but are not exclusive or determinative. The probes and primers are selected from the region of the porcine iGb3 synthase nucleic acid sequence identified in SEQ ID Nos. 1, 3-10, 11, 12, and 13, and fragments thereof. The probes and primers lack homology with sequences of other genes that would be expected to compromise the test. The probes or primers lack secondary structure formation in the amplified nucleic acid which can interfere with extension by the amplification enzyme such as $E.\ coli$ DNA polymerase, preferably that portion of the DNA polymerase referred to as the Klenow fragment. This can be accomplished by employing up to about 15% by weight, preferably 5-10% by weight, dimethyl sulfoxide (DMSO) in the amplification medium and/or increasing the amplification temperatures to 30°-40° C.

Preferably, the probes or primers should contain approximately 50% guanine and cytosine nucleotides, as measured by the formula adenine (A)+thymine (T)+cytosine (C)+guanine (G)/cytosine (C)+guanine (G). Preferably, the probe or primer does not contain multiple consecutive adenine and thymine residues at the 3' end of the primer which can result in less stable hybrids.

The probes and primers of the invention can be about 10 to 30 nucleotides long, preferably at least 10, 11, 12, 13, 14, 15, 20, 25, or 28 nucleotides in length, including specifically 14, 15, 16, 17, 18, 19, 20, 21, 22, 23, 24, 25, 26, 27, 28, 29 or 30 nucleotides. The nucleotides as used in the present invention can be ribonucleotides, deoxyribonucleotides and modified nucleotides such as inosine or nucleotides containing modified groups which do not essentially alter their hybridization characteristics. Probe and primer sequences are represented throughout the specification as single stranded DNA oligonucleotides from the 5' to the 3' end. Any of the probes can be used as such, or in their complementary form, or in their RNA form (wherein T is replaced by U).

The probes and primers according to the invention can be prepared by cloning of recombinant plasmids containing inserts including the corresponding nucleotide sequences, optionally by cleaving the latter out from the cloned plasmids upon using the adequate nucleases and recovering them, e.g. by fractionation according to molecular weight. The probes and primers according to the present invention can also be synthesized chemically, for instance by the conventional phosphotriester or phosphodiester methods or automated embodiments thereof. In one such automated embodiment diethylphosphoramidites are used as starting materials and can be synthesized as described by Beaucage, et al., *Tetrahedron Letters* 22:1859-1862 (1981). One method of synthesizing oligonucleotides on a modified solid support is described in U.S. Pat. No. 4,458,066. It is also possible to use a probe or primer which has been isolated from a biological source (such as a restriction endonuclease digest).

The oligonucleotides used as primers or probes can also comprise nucleotide analogues such as phosphorothiates (Matsukura S., *Naibunpi Gakkai Zasshi.* 43(6):527-32 (1967)), alkylphosphorothiates (Miller P., et al., *Biochemistry* 18(23):5134-43 (1979), peptide nucleic acids (Nielsen P., et al., *Science* 254(5037):1497-500 (1991); Nielsen P., et al., *Nucleic-Acids-Res.* 21(2):197-200 (1993)), morpholino nucleic acids, locked nucleic acids, pseudocyclic oligonucleobases, 2'-O,4'-C-ethylene bridged nucleic acids or can contain intercalating agents (Asseline J., et al., *Proc. Natl. Acad. Sci. USA* 81(11):3297-301 (1984)).

For designing probes and primers with desired characteristics, the following useful guidelines known to the person skilled in the art can be applied. Because the extent and specificity of hybridization reactions are affected by a number of factors, manipulation of one or more of those factors will determine the exact sensitivity and specificity of a particular probe, whether perfectly complementary to its target or not. The importance and effect of various assay conditions, explained further herein, are known to those skilled in the art.

The stability of the probe and primer to target nucleic acid hybrid should be chosen to be compatible with the assay conditions. This can be accomplished by avoiding long AT-rich sequences, by terminating the hybrids with GC base pairs, and/or by designing the probe with an appropriate Tm. The beginning and end points of the probe should be chosen so that the length and % GC result in a Tm about 2-10° C. higher than the temperature at which the final assay will be performed. The base composition of the probe is significant because G-C base pairs exhibit greater thermal stability compared to A-T base pairs due to additional hydrogen bonding. Thus, hybridization involving complementary nucleic acids of higher G-C content will be stable at higher temperatures. Conditions such as ionic strength and incubation temperature under which probe will be used should also be taken into account when designing a probe. It is known that hybridization will increase as the ionic strength of the reaction mixture increases, and that the thermal stability of the hybrids will increase with increasing ionic strength. Chemical reagents, such as formamide, urea, DIVISO and alcohols, which disrupt hydrogen bonds, will increase the stringency of hybridization. Destabilization of the hydrogen bonds by such reagents can greatly reduce the Tm. In general, optimal hybridization for synthetic oligonucleotide probes of about 10-50 bases in length occurs approximately 5° C. below the melting temperature for a given duplex. Incubation at temperatures below the optimum can allow mismatched base sequences to hybridize and can therefore result in reduced specificity. It is desirable to have probes which hybridize only under conditions of high stringency. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. The degree of stringency is chosen such as to maximize the difference in stability between the hybrid formed with the target and the non-target nucleic acid. In the present case, single base pair changes need to be detected, which requires conditions of very high stringency.

The length of the target nucleic acid sequence and, accordingly, the length of the probe sequence can also be important. In some cases, there can be several sequences from a particular region, varying in location and length, which will yield probes and primers with the desired hybridization characteristics. In other cases, one sequence can be significantly better than another which differs merely by a single base.

While it is possible for nucleic acids that are not perfectly complementary to hybridize, the longest stretch of perfectly complementary base sequence will normally primarily determine hybrid stability. While oligonucleotide probes and primers of different lengths and base composition can be used, preferred oligonucleotide probes and primers of this invention are between about 14 and 30 bases in length and have a sufficient stretch in the sequence which is perfectly complementary to the target nucleic acid sequence.

Regions in the target DNA or RNA which are known to form strong internal structures inhibitory to hybridization are less preferred. Likewise, probes with extensive self-complementarity should be avoided. As explained above, hybridization is the association of two single strands of complementary nucleic acids to form a hydrogen bonded double strand. It is implicit that if one of the two strands is wholly or partially involved in a hybrid, it will be less able to participate in formation of a new hybrid. There can be intramolecular and intermolecular hybrids formed within the molecules of one type of probe if there is sufficient self complementarity. Such structures can be avoided through careful probe design. By designing a probe so that a substantial portion of the sequence of interest is single stranded, the rate and extent of hybridization can be greatly increased. Computer programs are available to search for this type of interaction. However, in certain instances, it may not be possible to avoid this type of interaction.

Specific primers and sequence specific oligonucleotide probes can be used in a polymerase chain reaction that enables amplification and detection of porcine iGb3 synthase nucleic acid sequences.

IV. Genetic Targeting of the Porcine iGB3 Synthase Gene

Gene targeting allows for the selective manipulation of animal cell genomes. Using this technique, a particular DNA sequence can be targeted and modified in a site-specific and precise manner. Different types of DNA sequences can be targeted for modification, including regulatory regions, coding regions and regions of DNA between genes. Examples of regulatory regions include: promoter regions, enhancer regions, terminator regions and introns. By modifying these regulatory regions, the timing and level of expression of a gene can be altered. Coding regions can be modified to alter, enhance or eliminate the protein within a cell. Introns and exons, as well as inter-genic regions, are suitable targets for modification.

Modifications of DNA sequences can be of several types, including insertions, deletions, substitutions, or any combination thereof. A specific example of a modification is the inactivation of a gene by site-specific integration of a nucleotide sequence that disrupts expression of the gene product, i.e. a "knock out". For example, one approach to disrupting the porcine iGb3 synthase gene is to insert a selectable marker into the targeting DNA such that homologous recombination between the targeting DNA and the target DNA can result in insertion of the selectable marker into the coding region of the target gene. In this way, for example, the porcine iGb3 synthase gene sequence is disrupted, rendering the encoded enzyme nonfunctional.

a. Homologous Recombination.

Homologous recombination permits site-specific modifications in endogenous genes and thus novel alterations can be engineered into the genome. A primary step in homologous recombination is DNA strand exchange, which involves a pairing of a DNA duplex with at least one DNA strand containing a complementary sequence to form an intermediate recombination structure containing heteroduplex DNA (see, Radding, C. M. (1982) *Ann. Rev. Genet.* 16: 405; U.S. Pat. No. 4,888,274). The heteroduplex DNA can take several forms, including a three DNA strand containing triplex form wherein a single complementary strand invades the DNA duplex (Hsieh et al. (1990) *Genes and Development* 4: 1951; Rao et al., (1991) PNAS 88:2984)) and, when two complementary DNA strands pair with a DNA duplex, a classical Holliday recombination joint or chi structure (Holliday, R. (1964) *Genet. Res.* 5: 282) can form, or a double-D loop ("Diagnostic Applications of Double-D Loop Formation" U.S. Ser. No. 07/755,462, filed Sep. 4, 1991, which is incorporated herein by reference). Once formed, a heteroduplex structure can be resolved by strand breakage and exchange, so that all or a portion of an invading DNA strand is spliced into a recipient DNA duplex, adding or replacing a segment of the recipient DNA duplex. Alternatively, a heteroduplex structure can result in gene conversion, wherein a sequence of an invading strand is transferred to a recipient DNA duplex by repair of mismatched bases using the invading strand as a template (*Genes*, 3rd Ed. (1987) Lewin, B., John Wiley, New York, N.Y.; Lopez et al. (1987) *Nucleic Acids Res.* 15: 5643). Whether by the mechanism of breakage and rejoining or by the mechanism(s) of gene conversion, formation of heteroduplex DNA at homologously paired joints can serve to transfer genetic sequence information from one DNA molecule to another.

The ability of homologous recombination (gene conversion and classical strand breakage/rejoining) to transfer genetic sequence information between DNA molecules makes targeted homologous recombination a powerful method in genetic engineering and gene manipulation.

In homologous recombination, the incoming DNA interacts with and integrates into a site in the genome that contains a substantially homologous DNA sequence. In non-homologous ("random" or "illicit") integration, the incoming DNA is not found at a homologous sequence in the genome but integrates elsewhere, at one of a large number of potential locations. In general, studies with higher eukaryotic cells have revealed that the frequency of homologous recombination is far less than the frequency of random integration. The ratio of these frequencies has direct implications for "gene targeting" which depends on integration via homologous recombination (i.e. recombination between the exogenous "targeting DNA" and the corresponding "target DNA" in the genome).

A number of papers describe the use of homologous recombination in mammalian cells. Illustrative of these papers are Kucherlapati et al., Proc. Natl. Acad. Sci. USA 81:3153-3157, 1984; Kucherlapati et al., Mol. Cell. Bio. 5:714-720, 1985; Smithies et al, Nature 317:230-234, 1985; Wake et al., Mol. Cell. Bio. 8:2080-2089, 1985; Ayares et al., Genetics 111:375-388, 1985; Ayares et al., Mol. Cell. Bio. 7:1656-1662, 1986; Song et al., Proc. Natl. Acad. Sci. USA 84:6820-6824, 1987; Thomas et al. Cell 44:419-428, 1986; Thomas and Capecchi, Cell 51: 503-512, 1987; Nandi et al., Proc. Natl. Acad. Sci. USA 85:3845-3849, 1988; and Mansour et al., Nature 336:348-352, 1988. Evans and Kaufman, Nature 294:146-154, 1981; Doetschman et al., Nature 330: 576-578, 1987; Thomas and Capecchi, Cell 51:503-512, 4987; Thompson et al., Cell 56:316-321, 1989.

The present invention uses homologous recombination to inactivate the porcine iGb3 synthase gene in cells, such as fibroblasts. The DNA can comprise at least a portion of the gene at the particular locus with introduction of an alteration into at least one, optionally both copies, of the native gene, so as to prevent expression of a functional iGb3 synthase protein. The alteration can be an insertion, deletion, replacement or combination thereof. When the alteration is introduce into only one copy of the gene being inactivated, the cells having a single unmutated copy of the target gene are amplified and can be subjected to a second targeting step, where the alteration can be the same or different from the first alteration, usually different, and where a deletion, or replacement is involved, can be overlapping at least a portion of the alteration originally introduced. In this second targeting step, a targeting vector with the same arms of homology, but containing a different mammalian selectable marker can be used. The resulting transformants are screened for the absence of a functional target antigen and the DNA of the cell can be further screened to ensure the absence of a wild-type target gene. Alternatively, homozygosity as to a phenotype can be achieved by breeding hosts heterozygous for the mutation.

Porcine cells that can be genetically modified can be obtained from a variety of different organs and tissues such as, but not limited to, brain, heart, lungs, glands, brain, eye, stomach, spleen, pancreas, kidneys, liver, intestines, uterus, bladder, skin, hair, nails, ears, nose, mouth, lips, gums, teeth, tongue, salivary glands, tonsils, pharynx, esophagus, large intestine, small intestine, rectum, anus, pylorus, thyroid gland, thymus gland, suprarenal capsule, bones, cartilage, tendons, ligaments, skeletal muscles, smooth muscles, blood vessels, blood, spinal cord, trachea, ureters, urethra, hypothalamus, pituitary, adrenal glands, ovaries, oviducts, uterus, vagina, mammary glands, testes, seminal vesicles, penis, lymph, lymph nodes and lymph vessels. In one embodiment of the invention, porcine cells can be selected from the group consisting of, but not limited to, epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, phosphate cells, cumulus cells, epidermal cells, endothelial cells, Islets of Langerhans cells, blood cells, blood precursor cells, bone cells, bone precursor cells, neuronal stem cells, primordial stem cells, hepatocytes, keratinocytes, umbilical vein endothelial cells, aortic endothelial cells, microvascular endothelial cells, fibroblasts, liver stellate cells, aortic smooth muscle cells, cardiac myocytes, neurons, Kupffer cells, smooth muscle cells, Schwann cells, and epithelial cells, erythrocytes, platelets, neutrophils, lymphocytes, monocytes, eosinophils, basophils, adipocytes, chondrocytes, pancreatic islet cells, thyroid cells, parathyroid cells, parotid cells, tumor cells, glial cells, astrocytes, red blood cells, white blood cells, macrophages, epithelial cells, somatic cells, pituitary cells, adrenal cells, hair cells, bladder cells, kidney cells, retinal cells, rod cells, cone cells, heart cells, pacemaker cells, spleen cells, antigen presenting cells, memory cells, T cells, B cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, squamous epithelial cells, osteocytes, osteoblasts, and osteoclasts.

In one alternative embodiment, embryonic stem cells can be used. An embryonic stem cell line can be employed or embryonic stem cells can be obtained freshly from a host, such as a porcine animal. The cells can be grown on an appropriate fibroblast-feeder layer or grown in the presence of leukemia inhibiting factor (LIF). In a preferred embodiment, the porcine cells can be fibroblasts; in one specific embodiment, the porcine cells can be fetal fibroblasts. Fibroblast cells are a preferred somatic cell type because they can be obtained from developing fetuses and adult animals in large quantities.

These cells can be easily propagated in vitro with a rapid doubling time and can be clonally propagated for use in gene targeting procedures.

b. Targeting Vectors

Cells homozygous at a targeted locus can be produced by introducing DNA into the cells, where the DNA has homology to the target locus and includes a marker gene, allowing for selection of cells comprising the integrated construct. The homologous DNA in the target vector will recombine with the chromosomal DNA at the target locus. The marker gene can be flanked on both sides by homologous DNA sequences, a 3'recombination arm and a 5' recombination arm. Methods for the construction of targeting vectors have been described in the art, see, for example, Dai et al., Nature Biotechnology 20: 251-255, 2002; WO 00/51424.

Various constructs can be prepared for homologous recombination at a target locus. Usually, the construct can include at least 50 bp, 100 bp, 500 bp, 1 kbp, 2 kbp, 4 kbp, 5 kbp, 10 kbp, 15 kbp, 20 kbp, or 50 kbp of sequence homologous with the target locus. The sequence can include any contiguous sequence of the porcine iGb3 synthase gene, including at least 5, 10, 15, 17, 20, 25, 26, 27, 28, 29, 30, 35, 40, 45, 50, 55, 60, 65, 70, 75, 80, 85, 90 95, 100, 110, 120, 130, 140, 150, 160, 170, 180, 190, 200, 225, 250, 275, 300, 325, 350, 375, 400, 425, 450, 475, 500, 550, 600, 700, 650, 750, 800, 850, 900, 1000 contiguous nucleotides of Seq ID Nos 3-10, 11, 12, or 13, or any combination or fragment thereof. Fragments of Seq ID Nos. 3-10, 11, 12, or 13 can include any contiguous nucleic acid or peptide sequence that includes at least about 10 bp, 15 bp, 17 bp, 20 bp, 50 bp, 100 bp, 500 bp, 1 kbp, 5 kbp or 10 kpb. The construct can include a sequence which encodes a polypeptide comprising the amino acid sequence of Seq ID No. 2 or a nucleotide sequence encoding a polypeptide comprising an amino acid sequence which is homologous to Seq ID No. 2. The construct can also include a nucleotide sequence encoding a polypeptide comprising an amino acid sequence homologous to Seq ID No. 2 having at least 99%, at least 95%, at least 90%, at least 85%, at least 80%, at least 70%, at least 60%, at least 50%, at least 40% or at least 25% amino acid identity or similarity to a polypeptide comprising the sequence of Seq ID No. 2 or a nucleotide sequence encoding an amino acid sequence having at least 99%, at least 95%, at least 90%, at least 85%, at least 80%, at least 70%, at least 60%, at least 50%, at least 40% or at least 25% amino acid identity or similarity to a fragment comprising at least 5, 10, 15, 20, 25, 30, 35, 40, 50, 75, 100, 150, 200, 250, 300 or 350 consecutive amino acids of Seq ID No. 2. The percentage of similarity or identity to Seq ID No. 2 can be determined using the FASTA version 3.0t78 algorithm with the default parameters. Alternatively, the percentage of identity or similarity to Seq ID No. 2 can be determined using BLASTP with the default parameters, BLASTX with the default parameters, or TBLASTN with the default parameters. (Altschul, S. F. et al. Gapped BLAST and PSI-BLAST: A New Generation of Protein Database Search Programs, Nucleic Acid Res. 25: 3389-3402 (1997), the disclosure of which is incorporated herein by reference in its entirety Various considerations can be involved in determining the extent of homology of target DNA sequences, such as, for example, the size of the target locus, availability of sequences, relative efficiency of double cross-over events at the target locus and the similarity of the target sequence with other sequences.

The targeting DNA can include a sequence in which DNA substantially isogenic flanks the desired sequence modifications with a corresponding target sequence in the genome to be modified. The substantially isogenic sequence can be at least about 95%, 97-98%, 99.0-99.5%, 99.6-99.9%, or 100% identical to the corresponding target sequence (except for the desired sequence modifications). The targeting DNA and the target DNA preferably can share stretches of DNA at least about 75, 150 or 500 base pairs that are 100% identical. Accordingly, targeting DNA can be derived from cells closely related to the cell line being targeted; or the targeting DNA can be derived from cells of the same cell line or animal as the cells being targeted.

The DNA constructs can be designed to modify the endogenous, target porcine iGb3 synthase gene. The homologous sequence for targeting the construct can have one or more deletions, insertions, substitutions or combinations thereof.

The alteration can be the insertion of a selectable marker gene fused in reading frame with the upstream sequence of the target gene.

Suitable selectable marker genes include, but are not limited to: genes conferring the ability to grow on certain media substrates, such as the tk gene (thymidine kinase) or the hprt gene (hypoxanthine phosphoribosyltransferase) which confer the ability to grow on HAT medium (hypoxanthine, aminopterin and thymidine); the bacterial gpt gene (guanine/xanthine phosphoribosyltransferase) which allows growth on MAX medium (mycophenolic acid, adenine, and xanthine). See Song et al., Proc. Nat'l Acad. Sci. U.S.A. 84:6820-6824 (1987). See also Sambrook et al., Molecular Cloning—A Laboratory Manual, Cold Spring Harbor Laboratory, Cold Spring Harbor, N.Y. (1989), see chapter 16. Other examples of selectable markers include: genes conferring resistance to compounds such as antibiotics, genes conferring the ability to grow on selected substrates, genes encoding proteins that produce detectable signals such as luminescence, such as green fluorescent protein, enhanced green fluorescent protein (eGFP). A wide variety of such markers are known and available, including, for example, antibiotic resistance genes such as the neomycin resistance gene (neo), Southern, P., and P. Berg, J. Mol. Appl. Genet. 1:327-341 (1982); and the hygromycin resistance gene (hyg), Nucleic Acids Research 11:6895-6911 (1983), and Te Riele et al., Nature 348:649-651 (1990). Other selectable marker genes include: acetohydroxy acid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline.

Methods for the incorporation of antibiotic resistance genes and negative selection factors will be familiar to those of ordinary skill in the art (see, e.g., WO 99/15650; U.S. Pat. No. 6,080,576; U.S. Pat. No. 6.136,566; Niwa, et al., *J. Biochem.* 113:343-349 (1993); and Yoshida, et al., *Transgenic Research,* 4:277-287 (1995)).

Additional selectable marker genes useful in this invention, for example, are described in U.S. Pat. Nos: 6,319,669; 6,316,181; 6,303,373; 6,291,177; 6,284,519; 6,284,496; 6,280,934; 6,274,354; 6,270,958; 6,268,201; 6,265,548; 6,261,760; 6,255,558; 6,255,071; 6,251,677; 6,251,602; 6,251,582; 6,251,384; 6,248,558; 6,248,550; 6,248,543; 6,232,107; 6,228,639; 6,225,082; 6,221,612; 6,218,185; 6,214,567; 6,214,563; 6,210,922; 6,210,910; 6,203,986; 6,197,928; 6,180,343; 6,172,188; 6,153,409; 6,150,176; 6,146,826; 6,140,132; 6,136,539; 6,136,538; 6,133,429; 6,130,313; 6,124,128; 6,110,711; 6,096,865; 6,096,717; 6,093,808; 6,090,919; 6,083,690; 6,077,707; 6,066,476; 6,060,247; 6,054,321; 6,037,133; 6,027,881; 6,025,192; 6,020,192; 6,013,447; 6,001,557; 5,994,077; 5,994,071; 5,993,778; 5,989,808; 5,985,577; 5,968,773; 5,968,738; 5,958,713; 5,952,236; 5,948,889; 5,948,681; 5,942,387; 5,932,435; 5,922,576; 5,919,445; and 5,914,233.

Combinations of selectable markers can also be used. For example, to target porcine iGb3 synthase gene, a neo gene (with or without its own promoter, as discussed above) can be cloned into a DNA sequence which is homologous to the porcine iGb3 synthase gene. To use a combination of markers, the HSV-tk gene can be cloned such that it is outside of the targeting DNA (another selectable marker could be placed on the opposite flank, if desired). After introducing the DNA construct into the cells to be targeted, the cells can be selected on the appropriate antibiotics. In this particular example, those cells which are resistant to G418 and gancyclovir are most likely to have arisen by homologous recombination in which the neo gene has been recombined into the porcine iGb3 synthase gene but the tk gene has been lost because it was located outside the region of the double crossover.

Deletions can be at least about 50 bp, more usually at least about 100 bp, and generally not more than about 20 kbp, where the deletion can normally include at least a portion of the coding region including a portion of or one or more exons, a portion of or one or more introns, and can or can not include a portion of the flanking non-coding regions, particularly the 5'-non-coding region (transcriptional regulatory region). Thus, the homologous region can extend beyond the coding region into the 5'-non-coding region or alternatively into the 3'-non-coding region. Insertions can generally not exceed 10 kbp, usually not exceed 5 kbp, generally being at least 50 bp, more usually at least 200 bp.

The region(s) of homology can include mutations, where mutations can further inactivate the target gene, in providing for a frame shift, or changing a key amino acid, or the mutation can correct a dysfunctional allele, etc. Usually, the mutation can be a subtle change, not exceeding about 5% of the homologous flanking sequences. Where mutation of a gene is desired, the marker gene can be inserted into an intron, so as to be excised from the target gene upon transcription.

Figure 4:
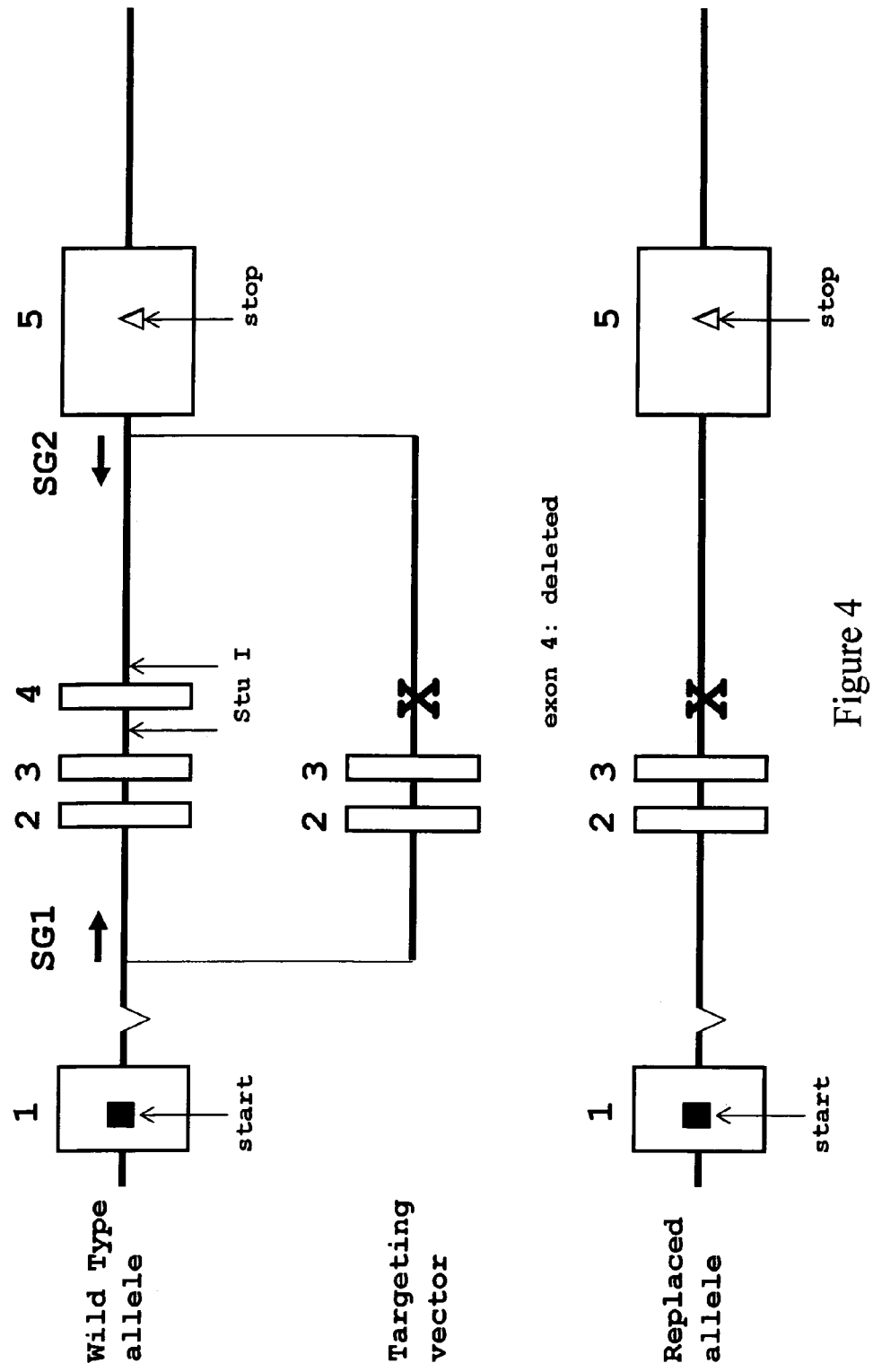
FIG. 4 illustrates representative targeting vectors for iGb3 synthase gene knockout, along with their corresponding genomic organization. A vector targeting Exon 4 is generated utilizing the primers SG1 (5'-CAGGGATTAACTCAA-CATCCAGGACAG-3'(Seq ID No. 14)) and SG2 (5-GAGT-CAGCTGGTCACTGCGCCCTT-3'(Seq ID No. 15)). The amplified PCR product is inserted into a vector, such as a pCRII vector (commercially available from Invitrogen). The vector is digested with the restriction enzyme Stu I and self-ligated.

The construct can be prepared in accordance with methods known in the art, various fragments can be brought together, introduced into appropriate vectors, cloned, analyzed and then manipulated further until the desired construct has been achieved see, for example, FIG. 4). Various modifications can be made to the sequence, to allow for restriction analysis, excision, identification of probes, etc. Silent mutations can be introduced, as desired. At various stages, restriction analysis, sequencing, amplification with the polymerase chain reaction, primer repair, in vitro mutagenesis, etc. can be employed.

The construct can be prepared using a bacterial vector, including a prokaryotic replication system, e.g. an origin recognizable by *E. coli*, at each stage the construct can be cloned and analyzed. A marker, the same as or different from the marker to be used for insertion, can be employed, which can be removed prior to introduction into the target cell. Once the vector containing the construct has been completed, it can be further manipulated, such as by deletion of the bacterial sequences, linearization, introducing a short deletion in the homologous sequence. After final manipulation, the construct can be introduced into the cell.

Techniques which can be used to allow the DNA construct entry into the host cell include calcium phosphate/DNA coprecipitation, microinjection of DNA into the nucleus, electroporation, bacterial protoplast fusion with intact cells, transfection, or any other technique known by one skilled in the art. The DNA can be single or double stranded, linear or circular, relaxed or supercoiled DNA. For various techniques for transfecting mammalian cells, see, for example, Keown et al., Methods in Enzymology Vol. 185, pp. 527-537 (1990).

The present invention further includes recombinant constructs comprising one or more of the sequences as broadly described above (for example in Tables 3-6). The constructs comprise a vector, such as a plasmid or viral vector, into which a sequence of the invention has been inserted, in a forward or reverse orientation. The construct can also include regulatory sequences, including, for example, a promoter, operably linked to the sequence. Large numbers of suitable vectors and promoters are known to those of skill in the art, and are commercially available. The following vectors are provided by way of example: pBs, pQE-9 (Qiagen), phagescript, PsiX 174, pBluescript SK, pBsKS, pNH8a, pNH16a, pNH18a, pNH46a (Stratagene); pTrc99A, pKK223-3, pKK233-3, pDR540, pRIT5 (Pharmacia). Eukaryotic: pWLneo, pSv2cat, pOG44, pXT1, pSG (Stratagene) pSVK3, pBPv, pMSG, pSVL (Pharmiacia). Also, any other plasmids and vectors can be used as long as they are replicable and viable in the host. Vectors known in the art and those commercially available (and variants or derivatives thereof) can in accordance with the invention be engineered to include one or more recombination sites for use in the methods of the invention. Such vectors can be obtained from, for example, Vector Laboratories Inc., Invitrogen, Promega, Novagen, NEB, Clontech, Boehringer Mannheim, Pharmacia, EpiCenter, OriGenes Technologies Inc., Stratagene, PerkinElmer, Pharmingen, and Research Genetics. Other vectors of interest include eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMClneo, and pOG44 (Stratagene, Inc.), and pYES2, pAC360, pBlueBacHis A, B, and C, pVL1392, pBlueBacIII, pCDM8, pcDNA1, pZeoSV, pcDNA3 pREP4, pCEP4, and pEBVHis (Invitrogen, Corp.) and variants or derivatives thereof.

Other vectors suitable for use in the invention include pUC18, pUC19, pBlueScript, pSPORT, cosmids, phagemids, YAC's (yeast artificial chromosomes), BAC's (bacterial artificial chromosomes), P1 (*Escherichia coli* phage), pQE70, pQE60, pQE9 (quagan), pBS vectors, PhageScript vectors, BlueScript vectors, pNH8A, pNH16A, pNH18A, pNH46A (Stratagene), pcDNA3 (Invitrogen), pGEX, pTrsfus, pTrc99A, pET-5, pET-9, pKK223-3, pKK233-3, pDR540, pRIT5 (Pharmacia), pSPORT1, pSPORT2, pCMVSPORT2.0 and pSV-SPORT1 (Invitrogen) and variants or derivatives thereof. Viral vectors can also be used, such as lentiviral vectors (see, for example, WO 03/059923; Tiscomia et al. PNAS 100:1844-1848 (2003)).

Additional vectors of interest include pTrxFus, pThioHis, pLEX, pTrcHis, pTrcHis2, pRSET, pBlueBacHis2, pcDNA3.1/His, pcDNA3.1(−)/Myc-His, pSecTag, pEBVHis, pPIC9K, pPIC3.5K, pAO815, pPICZ, pPICZA, pPICZB, pPICZC, pGAPZA, pGAPZB, pGAPZC, pBlueBac4.5, pBlueBacHis2, pMelBac, pSinRep5, pSinHis, pIND, pIND(SP1), pVgRXR, pcDNA2.1, pYES2, pZErO1.1, pZErO-2.1, pCR-Blunt, pSE280, pSE380, pSE420, pVL1392, pVL1393, pCDM8, pcDNA1.1, pcDNA1.1/Amp, pcDNA3.1, pcDNA3.1/Zeo, pSe, SV2, pRc/CMV2, pRc/RSV, pREP4, pREP7, pREP8, pREP9, pREP 10, pCEP4, pEBVHis, pCR3.1, pCR2.1, pCR3.1-Uni, and pCRBac from Invitrogen; λ ExCell, λ gt11, pTrc99A, pKK223-3, pGEX-1 λ T, pGEX-2T, pGEX-2TK, pGEX-4T-1, pGEX4T-2, pGEX4T-3, pGEX-3X, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue(R), pT7Blue-2, pCITE4abc(+), pOCUS-2, pTAg, pET-32LIC, pET-30LIC, pBAC-2cp LIC, pBACgus-2cp LIC, pT7Blue-2 LIC, pT7Blue-2, λ SCREEN-1, λ BlueSTAR, pET-3abcd, pET-7abc, pET9abcd, pET11abcd, pET12abc, pET-14b, pET-15b, pET-16b, pET-17b-pET-17xb, pET-19b, pET-20b(+), pET-21abcd(+), pET-22b(+), pET-23abcd(+), pET-24abcd(+), pET-25b(+), pET-26b(+), pET-27b(+), pET-28abc(+), pET- 29abc(+), pET-30abc(+), pET-31b(+), pET-32abc(+), pET-33b(+), pBAC-1, pBACgus-1, pBAC4x-1, pBACgus4x-1, pBAC-3cp, pBACgus-2cp, pBACsurf-1, pig, Signal pig, pYX, Selecta Vecta-Neo, Selecta Vecta-Hyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFP-N, pEGFP-C, pEBFP, pGFPuv, pGFP, p6xHis-GFP, pSEAP2-Basic, pSEAP2-Contral, pSEAP2-Promoter, pSEAP2-Enhancer, pβgal-Basic, pβgal-Control, pβgal-Promoter, pβgal-Enhancer, pCMV, pTet-Off, pTet-On, pTK-Hyg, pRetro-Off, pRetro-On, pIRESlneo, pIRESlhyg, pLXSN, pLNCX, pLAPSN, pMAMneo, pMAMneo-CAT, pMAMneo-LUC, pPUR, pSV2neo, pYEX4T-1/2/3, pYEX-S1, pBacPAK-His, pBacPAK8/9, pAcUW31, BacPAK6, pTriplEx, λgt10, λgt11, pWE15, and λTriplEx from Clontech; Lambda ZAP II, pBK-CMV, pBK-RSV, pBluescript II KS +/−, pBluescript II SK +/−, pAD-GAL4, pBD-GAL4 Cam, pSurfscript, Lambda FIX II, Lambda DASH, Lambda EMBL3, Lambda EMBL4, SuperCos, pCR-Script Amp, pCR-Script Cam, pCR-Script Direct, pBS +/−, pBC KS +/−, pBC SK +/−, Phagescript, pCAL-n-EK, pCAL-n, pCAL-c, pCAL-kc, pET-3abcd, pET-11abcd, pSPUTK, pESP-1, pCMVLacI, pOPRSVI/MCS, pOP13 CAT,pXT1, pSG5, pPbac, pMbac, pMClneo, pMClneo Poly A, pOG44, pOG45, pFRTβGAL, pNEOβGAL, pRS403, pRS404, pRS405, pRS406, pRS413, pRS414, pRS415, and pRS416 from Stratagene.

Additional vectors include, for example, pPC86, pDBLeu, pDBTrp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4-5, pNLexA, pYESTrp and variants or derivatives thereof.

Also, any other plasmids and vectors known in the art can be used as long as they are replicable and viable in the host.

c. Selection of Homologously Recombined Cells

Cells that have been homologously recombined to knockout expression of the porcine iGb3 synthase gene can then be grown in appropriately-selected medium to identify cells providing the appropriate integration. Those cells which show the desired phenotype can then be further analyzed by restriction analysis, electrophoresis, Southern analysis, polymerase chain reaction, or another technique known in the art. By identifying fragments which show the appropriate insertion at the target gene site, cells can be identified in which homologous recombination has occurred to inactivate or otherwise modify the target gene.

The presence of the selectable marker gene inserted into the porcine iGb3 synthase gene establishes the integration of the target construct into the host genome. Those cells which show the desired phenotype can then be further analyzed by restriction analysis, electrophoresis, Southern analysis, polymerase chain reaction, etc to analyze the DNA in order to establish whether homologous or non-homologous recombination occurred. This can be determined by employing probes for the insert and then sequencing the 5' and 3' regions flanking the insert for the presence of the iGb3 synthase gene extending beyond the flanking regions of the construct or identifying the presence of a deletion, when such deletion is introduced. Primers can also be used which are complementary to a sequence within the construct and complementary to a sequence outside the construct and at the target locus. In this way, one can only obtain DNA duplexes having both of the primers present in the complementary chains if homologous recombination has occurred. By demonstrating the presence of the primer sequences or the expected size sequence, the occurrence of homologous recombination is supported.

The polymerase chain reaction used for screening homologous recombination events is described in Kim and Smithies, Nucleic Acids Res. 16:8887-8903, 1988; and Joyner et al., Nature 338:153-156, 1989. The combination of a mutant polyoma enhancer and a thymidine kinase promoter to drive the neomycin gene has been shown to be active in both embryonic stem cells and EC cells by Thomas and Capecchi, supra, 1987; Nicholas and Berg (1983) in Teratocarcinoma Stem Cell, eds. Siver, Martin and Strikland (Cold Spring Harbor Lab., Cold Spring Harbor, N.Y. (pp. 469497); and Linney and Donerly, Cell 35:693-699, (1983).

An alternative method for screening homologous recombination events includes utilizing monoclonal or polyclonal antibodies specific for porcine iGb3 synthase protein.

Further characterization of porcine cells lacking expression of functional porcine iGb3 synthase due to homologous recombination events include, but are not limited to, Southern Blot analysis, Northern Blot analysis, and/or sequence analysis, or by using anti-iGb3 synthase antibody assays.

The cell lines obtained from the first round of targeting are likely to be heterozygous for the targeted allele. Homozygosity, in which both alleles are modified, can be achieved in a number of ways. One approach is to grow up a number of cells in which one copy has been modified and then to subject these cells to another round of targeting using a different selectable marker. Alternatively, homozygotes can be obtained by breeding animals heterozygous for the modified allele, according to traditional Mendelian genetics. In some situations, it can be desirable to have two different modified alleles. This can be achieved by successive rounds of gene targeting or by breeding heterozygotes, each of which carries one of the desired modified alleles.

V. Genetic Manipulation of Additional Genes to Overcome Immunologic Barriers of Xenotransplantation In one aspect of the invention, cells homozygous for the nonfunctional porcine iGb3 synthase gene can be subject to further genetic modification. For example, one can introduce additional genetic capability into the homozygotic hosts, where the endogenous alleles have been made nonfunctional, to substitute, replace or provide different genetic capability to the host. One can remove the marker gene after homogenotization. By introducing a construct comprising substantially the same homologous DNA, possibly with extended sequences, having the marker gene portion of the original construct deleted, one can be able to obtain homologous recombination with the target locus. By using a combination of marker genes for integration, one providing positive selection and the other negative selection, in the removal step, one would select against the cells retaining the marker genes.

In one embodiment, porcine cells are provided that lack a functional porcine iGb3 synthase gene and a functional α1,3galactosyltransferase gene. Animals lacking functional porcine iGb3 synthase gene can be produced according to the present invention, and then cells from this animal can be used to knockout the α1,3galactosyltransferase gene. Heterozygous and homozygous α1,3galactosyltransferase-negative porcine have recently been reported (see, for example, Phelps, et al., *Science,* 299: pp. 411-414 (2003)), WO 2004/028243, Dai et al. Science 2003) Alternatively, cells from these α1,3galactosyltransferase knockout animals can be used and further modified to inactivate the porcine iGb3 synthase gene.

In one embodiment, porcine cells are provided that lack a functional porcine iGb3 synthase gene and a functional CMP-Neu5Ac hydroxylase gene (see, for example, U.S. Ser. No. 10/863,116) gene. Animals lacking functional porcine iGb3 synthase gene can be produced according to the present invention, and then cells from this animal can be used to knockout the CMP-Neu5Ac hydroxylase gene. Alternatively, cells from these CMP-Neu5Ac hydroxylase knockout animals can be used and further modified to inactivate the porcine iGb3 synthase gene.

In one embodiment, porcine cells are provided that lack a functional porcine iGb3 synthase gene and a functional Forssman synthase gene (see, for example, U.S. patent application Ser. No. 60/568,922). Animals lacking functional porcine iGb3 synthase gene can be produced according to the present invention, and then cells from this animal can be used to knockout the Forssman synthase gene. Alternatively, cells from these Forssman synthase gene knockout animals can be used and further modified to inactivate the porcine iGb3 synthase gene.

In one embodiment, porcine cells are provided that lack a functional porcine iGb3 synthase gene and a functional porcine invariant chain gene (see, for example, U.S. Ser. No. 10/947,920). Animals lacking functional porcine iGb3 synthase gene can be produced according to the present invention, and then cells from this animal can be used to knockout the porcine invariant chain gene. Alternatively, cells from these invariant chain gene knockout animals can be used and further modified to inactivate the porcine iGb3 synthase gene.

In an alternative embodiment, porcine cells are provided that lack a functional porcine iGb3 synthase gene and a combination of any of a functional α1,3galactosyltransferase gene, functional porcine invariant chain gene, CMP-Neu5Ac hydroxylase gene, and a functional Forssman synthetase gene. Animals lacking functional porcine iGb3 synthase gene can be produced according to the present invention, and then cells from this animal can be used to knockout any of the α1,3galactosyltransferase gene, porcine invariant chain gene, CMP-Neu5Ac hydroxylase gene, or a functional Forssman synthetase gene. Alternatively, cells from any combination of a α1,3galactosyltransferase gene, porcine invariant chain gene, CMP-Neu5Ac hydroxylase gene, or a functional Forssman synthetase gene knockout animal can be used and further modified to inactivate the porcine iGb3 synthase gene.

In another embodiment, porcine cells are provided that lack the porcine iGb3 synthase gene and produce human complement inhibiting proteins. Animals lacking functional porcine iGb3 synthase gene can be produced according to the present invention, and then cells from this animal can be further modified to express complement inhibiting proteins, such as human pr porcine complement inhibiting proteins, including, but not limited to, CD59 (cDNA reported by Philbrick, W. M., et al. Eur. J. Immunol. 20:87-92 (1990)),human decay accelerating factor (DAF)(cDNA reported by Medof et al., Proc. Natl. Acad. Sci. USA 84: 2007 (1987)), and human membrane cofactor protein (MCP) (cDNA reported by Lublin, D. et al., *J. Exp. Med.* 168: 181-194, (1988)).

Transgenic pigs producing human complement inhibiting proteins are known in the art (see, for example, U.S. Pat. No. 6,166,288). Alternatively, cells from these transgenic pigs producing human complement inhibiting proteins can be used and further modified to inactivate the porcine iGb3 synthase gene.

In another embodiment, porcine cells are provided that lack the porcine iGb3 synthase gene and lack a combination of a functional α1,3galactosyltransferase gene, porcine invariant chain gene, CMP-Neu5Ac hydroxylase gene, or a functional Forssman synthetase gene produce human complement inhibiting proteins. Animals lacking functional porcine iGb3 synthase gene and lacking a combination of a functional α1,3galactosyltransferase gene, porcine invariant chain gene, CMP-Neu5Ac hydroxylase gene, or a functional Forssman synthetase gene can be produced according to the present invention, and then cells from this animal can be further modified to express complement inhibiting proteins, such as human pr porcine complement inhibiting proteins, including, but not limited to, CD59 (cDNA reported by Philbrick, W. M., et al. Eur. J. Immunol. 20:87-92 (1990)),human decay accelerating factor (DAF)(cDNA reported by Medof et al., Proc. Natl. Acad. Sci. USA 84: 2007 (1987)), and human membrane cofactor protein (MCP) (cDNA reported by Lublin, D. et al., *J. Exp. Med* 168: 181-194, (1988)).

VI. Production of Genetically Modified Animals

The present invention provides methods of producing a transgenic pig that lacks expression of porcine iGb3 synthase through the genetic modification of porcine totipotent embryonic cells. In one embodiment, the animals can be produced by: (a) identifying one or more target porcine iGb3 synthase nucleic acid genomic sequences in an animal; (b) preparing one or more homologous recombination vectors targeting the porcine iGb3 synthase nucleic acid genomic sequences; (c) inserting the one or more targeting vectors into the genomes of a plurality of totipotent cells of the animal, thereby producing a plurality of transgenic totipotent cells; (d) obtaining a tetraploid blastocyst of the animal; (e) inserting the plurality of totipotent cells into the tetraploid blastocyst, thereby producing a transgenic embryo; (f) transferring the embryo to a recipient female animal; and (g) allowing the embryo to develop to term in the female animal. The method of transgenic animal production described here by which to generate a transgenic pig is further generally described in, for example, U.S. Pat. No. 6,492,575.

In another embodiment, the totipotent cells can be embryonic stem (ES) cells. The isolation of ES cells from blastocysts, the establishing of ES cell lines and their subsequent cultivation are carried out by conventional methods as described, for example, by Doetchmann et al., J. Embryol. Exp. Morph. 87:27-45 (1985); Li et al., Cell 69:915-926 (1992); Robertson, E. J. "Tetracarcinomas and Embryonic Stem Cells: A Practical Approach," ed. E. J. Robertson, IRL Press, Oxford, England (1987); Wurst and Joyner, "Gene Targeting: A Practical Approach," ed. A. L. Joyner, IRL Press, Oxford, England (1993); Hogen et al., "Manipulating the Mouse Embryo: A Laboratory Manual," eds. Hogan, Beddington, Costantini and Lacy, Cold Spring Harbor Laboratory Press, New York (1994); and Wang, et al., *Nature* 336:741-744 (1992). For example, after transforming embryonic stem cells with the targeting vector to alter the porcine iGb3 synthase gene, the cells can be plated onto a feeder layer in an appropriate medium, for example, such as fetal bovine serum enhanced DMEM. Cells containing the construct can be detected by employing a selective medium, and after sufficient time for colonies to grow, colonies can be picked and analyzed for the occurrence of homologous recombination. Polymerase chain reaction can be used, with primers within and without the construct sequence but at the target locus. Those colonies which show homologous recombination can then be used for embryo manipulating and blastocyst injection. Blastocysts can be obtained from superovulated females. The embryonic stem cells can then be trypsinized and the modified cells added to a droplet containing the blastocysts. At least one of the modified embryonic stem cells can be injected into the blastocoel of the blastocyst. After injection, at least one of the blastocysts can be returned to each uterine horn of pseudopregnant females. Females are then allowed to go to term and the resulting litters screened for mutant cells having the construct. The blastocysts are selected for different parentage from the transformed ES cells. By providing for a different phenotype of the blastocyst and the ES cells, chimeric progeny can be readily detected, and then genotyping can be conducted to probe for the presence of the modified porcine iGb3 synthase gene.

In a further embodiment of the invention, the totipotent cells can be embryonic germ (EG) cells. Embryonic Germ cells are undifferentiated cells functionally equivalent to ES cells, that is they can be cultured and transfected in vitro, then contribute to somatic and germ cell lineages of a chimera (Stewart et al., Dev. Biol. 161:626-628 (1994)). EG cells are derived by culture of primordial germ cells, the progenitors of the gametes, with a combination of growth factors: leukemia inhibitory factor, steel factor and basic fibroblast growth factor (Matsui, et al., *Cell* 70:841-847 (1992); Resnick, et al., *Nature* 359:550-551 (1992)). The cultivation of EG cells can be carried out using methods known to one skilled in the art, such as described in Donovan et al., "Transgenic Animals, Generation and Use," Ed. L. M. Houdebine, Harwood Academic Publishers (1997).

Tetraploid blastocysts for use in the invention can be obtained by natural zygote production and development, or by known methods by electrofusion of two-cell embryos and subsequently cultured as described, for example, by James, et al., *Genet. Res. Camb.* 60:185-194 (1992); Nagy and Rossant, "Gene Targeting: A Practical Approach," ed. A. L. Joyner, IRL Press, Oxford, England (1993); or by Kubiak and Tarkowski, *Exp. Cell Res.* 157:561-566 (1985).

The introduction of the ES cells or EG cells into the blastocysts can be carried out by any method known in the art, for example, as described by Wang, et al., *EMBO J.* 10:2437-2450 (1991).

A "plurality" of totipotent cells can encompass any number of cells greater than one. For example, the number of totipotent cells for use in the present invention can be about 2 to about 30 cells, about 5 to about 20 cells, or about 5 to about 10 cells. In one embodiment, about 5-10 ES cells taken from a single cell suspension are injected into a blastocyst immobilized by a holding pipette in a micromanipulation apparatus. Then the embryos are incubated for at least 3 hours, possibly overnight, prior to introduction into a female recipient animal via methods known in the art (see for example Robertson, E. J. "Teratocarcinomas and Embryonic Stem Cells: A Practical Approach" IRL Press, Oxford, England (1987)). The embryo can then be allowed to develop to term in the female animal.

Somatic Cell Nuclear Transfer to Produce Cloned, Transgenic offspring

The present invention provides a method for cloning a pig lacking a functional porcine iGb3 synthase gene via somatic cell nuclear transfer. In general, a wide variety of methods to accomplish mammalian cloning are currently being rapidly developed and reported, any method that accomplishes the desired result can be used in the present invention. Nonlimiting examples of such methods are described below. For example, the pig can be produced by a nuclear transfer process comprising the following steps: obtaining desired differentiated pig cells to be used as a source of donor nuclei; obtaining oocytes from a pig; enucleating the oocytes; transferring the desired differentiated cell or cell nucleus into the enucleated oocyte, e.g., by fusion or injection, to form NT units; activating the resultant NT unit; and transferring said cultured NT unit to a host pig such that the NT unit develops into a fetus.

Nuclear transfer techniques or nuclear transplantation techniques are known in the art (Campbell et al, *Theriogenology*, 43:181 (1995); Collas, et al, *Mol. Report Dev.*, 38:264-267 (1994); Keefer et al, *Biol. Reprod.*, 50:935-939 (1994); Sims, et al, *Proc. Natl. Acad. Sci., USA*, 90:6143-6147 (1993); WO 94/26884; WO 94/24274, and WO 90/03432, U.S. Pat. Nos. 4,944,384 and 5,057,420). In one nonlimiting example, methods are provided such as those described in U.S. Patent Publication No. 2003/0046722 to Collas, et al., which describes methods for cloning mammals that allow the donor chromosomes or donor cells to be reprogrammed prior to insertion into an enucleated oocyte. The invention also describes methods of inserting or fusing chromosomes, nuclei or cells with oocytes.

A donor cell nucleus, which has been modified to alter the iGb3 synthase gene, is transferred to a recipient porcine oocyte. The use of this method is not restricted to a particular donor cell type. The donor cell can be as described in Wilmut, et al., *Nature* 385 810 (1997); Campbell, et al., *Nature* 380 64-66 (1996); or Cibelli, et al., *Science* 280 1256-1258 (1998). All cells of normal karyotype, including embryonic, fetal and adult somatic cells which can be used successfully in nuclear transfer can in principle be employed. Fetal fibroblasts are a particularly useful class of donor cells. Generally suitable methods of nuclear transfer are described in Campbell, et al., *Theriogenology* 43 181 (1995), Collas, et al., *Mol. Reprod. Dev.* 38 264-267 (1994), Keefer, et al., *Biol. Reprod.* 50 935-939 (1994), Sims, et al., *Proc. Nat'l. Acad. Sci. USA* 90 6143-6147 (1993), WO-A-9426884, WO-A-9424274, WO-A-9807841, WO-A-9003432, U.S. Pat. No. 4,994,384 and U.S. Pat. No. 5,057,420. Differentiated or at least partially differentiated donor cells can also be used. Donor cells can also be, but do not have to be, in culture and can be quiescent. Nuclear donor cells which are quiescent are cells which can be induced to enter quiescence or exist in a quiescent state in vivo. Prior art methods have also used embryonic cell types in cloning procedures (Campbell, et al. (*Nature*, 380:64-68, 1996) and Stice, et al (*Biol. Reprod.*, 20 54:100-110, 1996).

Somatic nuclear donor cells may be obtained from a variety of different organs and tissues such as, but not limited to, skin, mesenchyme, lung, pancreas, heart, intestine, stomach, bladder, blood vessels, kidney, urethra, reproductive organs, and a disaggregated preparation of a whole or part of an embryo, fetus or adult animal. In a suitable embodiment of the invention, nuclear donor cells are selected from the group consisting of epithelial cells, fibroblast cells, neural cells, keratinocytes, hematopoietic cells, melanocytes, chondrocytes, lymphocytes (B and T), macrophages, monocytes, mononuclear cells, cadiac muscle cells, other muscle cells, granulose cells, cumulus cells, epidermal cells or endothelial cells. In another embodiment, the nuclear cell is an embryonic stem cell. In a preferred embodiment, fibroblast cells can be used as donor cells.

In another embodiment of the invention, the nuclear donor cells of the invention are germ cells of an animal. Any germ cell of an animal species in the embryonic, fetal, or adult stage may be used as a nuclear donor cell. In a suitable embodiment, the nuclear donor cell is an embryonic germ cell.

Nuclear donor cells may be arrested in any phase of the cell cycle (G0, G1, G2, S, M) so as to ensure coordination with the acceptor cell. Any method known in the art may be used to manipulate the cell cycle phase. Methods to control the cell cycle phase include, but are not limited to, G0 quiescence induced by contact inhibition of cultured cells, GO quiescence induced by removal of serum or other essential nutrient, GO quiescence induced by senescence, GO quiescence induced by addition of a specific growth factor; GO or GI quiescence induced by physical or chemical means such as heat shock, hyperbaric pressure or other treatment with a chemical, hormone, growth factor or other substance; S-phase control via treatment with a chemical agent which interferes with any. Point of the replication procedure; M-phase control via selection using fluorescence activated cell sorting, mitotic shake off, treatment with microtubule disrupting agents or any chemical which disrupts progression in mitosis (see also Freshney, R. I,. "Culture of Animal Cells: A Manual of Basic Technique," Alan R. Liss, Inc, New York (1983)).

Methods for isolation of oocytes are well known in the art. Essentially, this can comprise isolating oocytes from the ovaries or reproductive tract of a pig. A readily available source of pig oocytes is slaughterhouse materials. For the combination of techniques such as genetic engineering, nuclear transfer and cloning, oocytes must generally be matured in vitro before these cells can be used as recipient cells for nuclear transfer, and before they can be fertilized by the sperm cell to develop into an embryo. This process generally requires collecting immature (prophase I) oocytes from mammalian ovaries, e.g., bovine ovaries obtained at a slaughterhouse, and maturing the oocytes in a maturation medium prior to fertilization or enucleation until the oocyte attains the metaphase II stage, which in the case of bovine oocytes generally occurs about 18-24 hours post-aspiration. This period of time is known as the "maturation period".

A metaphase II stage oocyte can be the recipient oocyte, at this stage it is believed that the oocyte can be or is sufficiently "activated" to treat the introduced nucleus as it does a fertilizing sperm. Metaphase II stage oocytes, which have been matured in vivo have been successfully used in nuclear transfer techniques. Essentially, mature metaphase II oocytes can be collected surgically from either non-superovulated or superovulated porcine 35 to 48, or 39-41, hours past the onset of estrus or past the injection of human chorionic gonadotropin (hCG) or similar hormone.

After a fixed time maturation period, which ranges from about 10 to 40 hours, and preferably about 16-18 hours, the oocytes can be enucleated. Prior to enucleation the oocytes can be removed and placed in appropriate medium, such as HECM containing 1 milligram per milliliter of hyaluronidase prior to removal of cumulus cells. The stripped oocytes can then be screened for polar bodies, and the selected metaphase II oocytes, as determined by the presence of polar bodies, are then used for nuclear transfer. Enucleation follows.

Enucleation can be performed by known methods, such as described in U.S. Pat. No. 4,994,384. For example, metaphase II oocytes can be placed in either HECM, optionally containing 7.5 micrograms per milliliter cytochalasin B, for immediate enucleation, or can be placed in a suitable medium, for example an embryo culture medium such as CR1aa, plus 10% estrus cow serum, and then enucleated later, preferably not more than 24 hours later, and more preferably 16-18 hours later. Enucleation can be accomplished microsurgically using a micropipette to remove the polar body and the adjacent cytoplasm. The oocytes can then be screened to identify those of which have been successfully enucleated. One way to screen the oocytes is to stain the oocytes with 1 microgram per milliliter 33342 Hoechst dye in HECM, and then view the oocytes under ultraviolet irradiation for less than 10 seconds. The oocytes that have been successfully enucleated can then be placed in a suitable culture medium, for example, CR1aa plus 10% serum.

A single mammalian cell of the same species as the enucleated oocyte can then be transferred into the perivitelline space of the enucleated oocyte used to produce the NT unit. The mammalian cell and the enucleated oocyte can be used to produce NT units according to methods known in the art. For example, the cells can be fused by electrofusion. Electrofusion is accomplished by providing a pulse of electricity that is sufficient to cause a transient breakdown of the plasma membrane. This breakdown of the plasma membrane is very short because the membrane reforms rapidly. Thus, if two adjacent membranes are induced to breakdown and upon reformation the lipid bilayers intermingle, small channels can open between the two cells. Due to the thermodynamic instability of such a small opening, it enlarges until the two cells become one. See, for example, U.S. Pat. No. 4,997,384 by Prather et al. A variety of electrofusion media can be used including, for example, sucrose, mannitol, sorbitol and phosphate buffered solution. Fusion can also be accomplished using Sendai virus as a fusogenic agent (Graham, *Wister Inot. Symp. Monogr.,* 9, 19, 1969). Also, the nucleus can be injected directly into the oocyte rather than using electroporation fusion. See, for example, Collas and Barnes, Mol. Reprod. Dev., 38:264-267 (1994). After fusion, the resultant fused NT units are then placed in a suitable medium until activation, for example, CR1aa medium. Typically activation can be effected shortly thereafter, for example less than 24 hours later, or about 4-9 hours later.

The NT unit can be activated by any method that accomplishes the desired result. Such methods include, for example, culturing the NT unit at sub-physiological temperature, in essence by applying a cold, or actually cool temperature shock to the NT unit. This can be most conveniently done by culturing the NT unit at room temperature, which is cold relative to the physiological temperature conditions to which embryos are normally exposed. Alternatively, activation can be achieved by application of known activation agents. For example, penetration of oocytes by sperm during fertilization has been shown to activate prefusion oocytes to yield greater numbers of viable pregnancies and multiple genetically identical pigs after nuclear transfer. Also, treatments such as electrical and chemical shock can be used to activate NT embryos after fusion. See, for example, U.S. Pat. No. 5,496,720, to Susko-Parrish, et al. Additionally, activation can be effected by simultaneously or sequentially by increasing levels of divalent cations in the oocyte, and reducing phosphorylation of cellular proteins in the oocyte. This can generally be effected by introducing divalent cations into the oocyte cytoplasm, e.g., magnesium, strontium, barium or calcium, e.g., in the form of an ionophore. Other methods of increasing divalent cation levels include the use of electric shock, treatment with ethanol and treatment with caged chelators. Phosphorylation can be reduced by known methods, for example, by the addition of kinase inhibitors, e.g., serine-threonine kinase inhibitors, such as 6-dimethyl-aminopurine, staurosporine, 2-aminopurine, and sphingosine. Alternatively, phosphorylation of cellular proteins can be inhibited by introduction of a phosphatase into the oocyte, e.g., phosphatase 2A and phosphatase 2B.

The activated NT units can then be cultured in a suitable in vitro culture medium until the generation of cell colonies. Culture media suitable for culturing and maturation of embryos are well known in the art. Examples of known media, which can be used for embryo culture and maintenance, include Ham's F-10+10% fetal calf serum (FCS), Tissue Culture Medium-199 (TCM-199)+10% fetal calf serum, Tyrodes-Albumin-Lactate-Pyruvate (TALP), Dulbecco's Phosphate Buffered Saline (PBS), Eagle's and Whitten's media.

Afterward, the cultured NT unit or units can be washed and then placed in a suitable media contained in well plates which preferably contain a suitable confluent feeder layer. Suitable feeder layers include, by way of example, fibroblasts and epithelial cells. The NT units are cultured on the feeder layer until the NT units reach a size suitable for transferring to a recipient female, or for obtaining cells which can be used to produce cell colonies. Preferably, these NT units can be cultured until at least about 2 to 400 cells, more preferably about 4 to 128 cells, and most preferably at least about 50 cells.

Activated NT units can then be transferred (embryo transfers) to the oviduct of an female pigs. In one embodiment, the female pigs can be an estrus-synchronized recipient gilt. Crossbred gilts (large white/Duroc/Landrace) (280-400 lbs) can be used. The gilts can be synchronized as recipient animals by oral administration of 18-20 mg ReguMate (Altrenogest, Hoechst, Warren, N.J.) mixed into the feed. ReguMate can be fed for 14 consecutive days. One thousand units of Human Chorionic Gonadotropin (hCG, Intervet America, Millsboro, Del.) can then be administered i.m. about 105 h after the last Regu-Mate treatment. Embryo transfers of the can then be performed about 22-26 h after the hCG injection. In one embodiment, the pregnancy can be brought to term and result in the birth of live offspring. In another embodiment, the pregnancy can be 5 terminated early and embryonic cells can be harvested.

The methods for embryo transfer and recipient animal management in the present invention are standard procedures used in the embryo transfer industry. Synchronous transfers are important for success of the present invention, i.e., the stage of the NT embryo is in synchrony with the estrus cycle of the recipient female. See, for example, Siedel, G. E., Jr. "Critical review of embryo transfer procedures with cattle" in Fertilization and Embryonic Development in Vitro (1981) L. Mastroianni, Jr. and J. D. Biggers, ed., Plenum Press, New York, N.Y., page 323.

VII. Porcine Animals, Organs, Tissues, Cells and Cell Lines

The present invention provides viable porcine in which both alleles of the porcine iGb3 synthase gene have been inactivated. The invention also provides organs, tissues, and cells derived from such porcine, which are useful for xenotransplantation.

In one embodiment, the invention provides porcine organs, tissues and/or purified or substantially pure cells or cell lines obtained from pigs that lack any expression of functional iGb3 synthase.

In one embodiment, the invention provides organs that are useful for xenotransplantation. Any porcine organ can be used, including, but not limited to: brain, heart, lungs, glands, brain, eye, stomach, spleen, pancreas, kidneys, liver, intestines, uterus, bladder, skin, hair, nails, ears, nose, mouth, lips, gums, teeth, tongue, salivary glands, tonsils, pharynx, esophagus, large intestine, small intestine, rectum, anus, pylorus, thyroid gland, thymus gland, suprarenal capsule, bones, cartilage, tendons, ligaments, skeletal muscles, smooth muscles, blood vessels, blood, spinal cord, trachea, ureters, urethra, hypothalamus, pituitary, adrenal glands, ovaries, oviducts, uterus, vagina, mammary glands, testes, seminal vesicles, penis, lymph, lymph nodes and lymph vessels.

In another embodiment, the invention provides tissues that are useful for xenotransplantation. Any porcine tissue can be used, including, but not limited to: epithelium, connective tissue, blood, bone, cartilage, muscle, nerve, adenoid, adipose, areolar, bone, brown adipose, cancellous, muscle, cartaginous, cavernous, chondroid, chromaffin, dartoic, elastic, epithelial, fatty, fibrohyaline, fibrous, Gaingee, gelatinous, granulation, gut-associated lymphoid, Haller's vascular, hard hemopoietic, indifferent, interstitial, investing, islet, lymphatic, lymphoid, mesenchymal, mesonephric, mucous connective, multilocular adipose, myeloid, nasion soft, nephrogenic, nodal, osseous, osteogenic, osteoid, periapical, reticular, retiform, rubber, skeletal muscle, smooth muscle, and subcutaneous tissue.

In a further embodiment, the invention provides cells and cell lines from porcine animals that lack expression of functional iGb3 synthase. In one embodiment, these cells or cell lines can be used for xenotransplantation. Cells from any porcine tissue or organ can be used, including, but not limited to: epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, □hosphate cells, cumulus cells, epidermal cells, endothelial cells, Islets of Langerhans cells, pancreatic insulin secreting cells, pancreatic alpha-2 cells, pancreatic beta cells, pancreatic alpha-1 cells, blood cells, blood precursor cells, bone cells, bone precursor cells, neuronal stem cells, primordial stem cells., hepatocytes, keratinocytes, umbilical vein endothelial cells, aortic endothelial cells, microvascular endothelial cells, fibroblasts, liver stellate cells, aortic smooth muscle cells, cardiac myocytes, neurons, Kupffer cells, smooth muscle cells, Schwann cells, and epithelial cells, erythrocytes, platelets, neutrophils, lymphocytes, monocytes, eosinophils, basophils, adipocytes, chondrocytes, pancreatic islet cells, thyroid cells, parathyroid cells, parotid cells, tumor cells, glial cells, astrocytes, red blood cells, white blood cells, macrophages, epithelial cells, somatic cells, pituitary cells, adrenal cells, hair cells, bladder cells, kidney cells, retinal cells, rod cells, cone cells, heart cells, pacemaker cells, spleen cells, antigen presenting cells, memory cells, T cells, B cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, dopaminergic cells, squamous epithelial cells, osteocytes, osteoblasts, osteoclasts, embryonic stem cells, fibroblasts and fetal fibroblasts. In a specific embodiment, pancreatic cells, including, but not limited to, Islets of Langerhans cells, insulin secreting cells, 48 alpha-2 cells, beta cells, alpha-1 cells from pigs that lack expression of functional iGb3 synthase.

Nonviable derivatives include tissues stripped of viable cells by enzymatic or chemical treatment these tissue derivatives can be further processed via crosslinking or other chemical treatments prior to use in transplantation. In a preferred embodiment, the derivatives include extracellular matrix derived from a variety of tissues, including skin, urinary, bladder or organ submucosal tissues. Also, tendons, joints and bones stripped of viable tissue to include heart valves and other nonviable tissues as medical devices are provided.

Therapeutic Uses

The cells can be administered into a host in order in a wide variety of ways. Preferred modes of administration are parenteral, intraperitoneal, intravenous, intradermal, epidural, intraspinal, intrastemal, intra-articular, intra-synovial, intrathecal, intra-arterial, intracardiac, intramuscular, intranasal, subcutaneous, intraorbital, intracapsular, topical, transdermal patch, via rectal, vaginal or urethral administration including via suppository, percutaneous, nasal spray, surgical implant, internal surgical paint, infusion pump, or via catheter. In one embodiment, the agent and carrier are administered in a slow release formulation such as a direct tissue injection or bolus, implant, microparticle, microsphere, nanoparticle or nanosphere.

Disorders that can be treated by infusion of the disclosed cells include, but are not limited to, diseases resulting from a failure of a dysfunction of normal blood cell production and maturation (i.e., aplastic anemia and hypoproliferative stem cell disorders); neoplastic, malignant diseases in the hematopoietic organs (e.g., leukemia and lymphomas); broad spectrum malignant solid tumors of non-hematopoietic origin; autoimmune conditions; and genetic disorders. Such disorders include, but are not limited to diseases resulting from a failure or dysfunction of normal blood cell production and maturation hyperproliferative stem cell disorders, including aplastic anemia, pancytopenia, agranulocytosis, thrombocytopenia, red cell aplasia, Blackfan Diamond syndrome, due to drugs, radiation, or infection, idiopathic; hematopoietic malignancies including acute lymphoblastic (lymphocytic) leukemia, chronic lymphocytic leukemia, acute myelogenous leukemia, chronic myelogenous, leukemia, acute malignant myelosclerosis, multiple myeloma, polycythemia vera, agnogenic myelometaplasia, Waldenstrom's macroglobulinemia, Hodgkin's lymphoma, non-Hodgkin's lymphoma; immunosuppression in patients with malignant, solid tumors including malignant melanoma, carcinoma of the stomach, ovarian carcinoma, breast carcinoma, small cell lung carcinoma, retinoblastoma, testicular carcinoma, glioblastoma, rhabdomyosarcoma, neuroblastoma, Ewing's sarcoma, lymphonia; autoinimune diseases including rheumatoid arthritis, diabetes type 1, chronic hepatitis, multiple sclerosis, systemic lupus erythematosus; genetic (congenital) disorders including anemias, familial aplastic, Fanconi's syndrome, dihydrofolate reductase deficiencies, formamino transferase deficiency, Lesch-Nyhan syndrome, congenital dyserythropoietic syndrome IIV, Chwachmann-Diamond syndrome, dihydrofolate reductase deficiencies, forinamino transferase deficiency, Lesch-Nyhan syndrome, congenital spherocytosis, congenital elliptocytosis, congenital stomatocytosis, congenital Rhnull disease, paroxysmal nocturnal hemoglobinuria, G6PD (glucose □hosphate dehydrogenase) variants 1, 2, 3, pyruvate kinase deficiency, congenital erythropoietin sensitivity, deficiency, sickle cell disease and trait, thalassernia alpha, beta, gamma, met-hemoglobinemia, congenital disorders of immunity, severe combined immunodeficiency disease (SCID), bare lymphocyte syndrome, ionophore-responsive combined immunodeficiency, combined immunodeficiency with a capping abnormality, nucleoside phosphorylase deficiency, granulocyte actin deficiency, infantile agranulocytosis, Gaucher's disease, adenosine deaminase deficiency, Kostmann's syndrome, reticular dysgenesis, congenital Leukocyte dysfunction syndromes; and others such as osteoporosis, myeloselerosis, acquired hemolytic anemias, acquired immunodeficiencies, infectious disorders causing primary or secondary immunodeficiencies, bacterial infections (e.g., Brucellosis, Listerosis, tuberculosis, leprosy), parasitic infections (e.g., malaria, Leishmaniasis), fungal infections, disorders involving disproportionsin lymphoid cell sets and impaired immune functions due to aging, phagocyte disorders, Kostmann's agranulocytosis, chronic granulomatous disease, Chediak-Higachi syndrome, neutrophil actin deficiency, neutrophil membrane GP-180 deficiency, metabolic storage diseases, mucopolysaccharidoses, mucolipidoses, miscellaneous disorders involving immune mechanisms, Wiskott-Aldrich Syndrome, alpha 1 antirypsin deficiency, etc.

Diseases or pathologies include neurodegenerative diseases, hepatodegenerative diseases, nephrodegenerative disease, spinal cord injury, head trauma or surgery, viral infections that result in tissue, organ, or gland degeneration, and the like. Such neurodegenerative diseases include but are 1 0 not limited to, AIDS dementia complex; demyeliriating diseases, such as multiple sclerosis and acute transferase myelitis; extrapyramidal and cerebellar disorders, such as lesions of the ecorticospinal system; disorders of the basal ganglia or cerebellar disorders; hyperkinetic movement disorders, such as Huntington's Chorea and senile chorea; drug-induced movement disorders, such as those induced by drugs that block CNS dopamine receptors; hypokinetic movement disorders, such as Parkinson's disease; progressive supra-nucleo palsy; structural lesions of the cerebellum; spinocerebellar degenerations, such as spinal ataxia, Friedreich's ataxia, cerebellar cortical degenerations, multiple systems degenerations (Mencel, Dejerine Thomas, Shi-Drager, and Machado-Joseph), systermioc disorders, such as Rufsum's disease, abetalipoprotemia, ataxia, telangiectasia; and mitochondrial multisystem disorder; demyelinating core disorders, such as multiple sclerosis, acute transverse myelitis; and disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diff-use Lewy body disease; Senile Demetia of Lewy body type; Parkinson's Disease, Wemicke-Korsakoff syndrome; chronic alcoholism; Creutzfeldt-Jakob disease; Subacute sclerosing panencephalitis hallefforden-Spatz disease; and Dementia pugilistica. See, e.g., Berkow et. al., (eds.) (1987), The Merck Manual, (15') ed.), Merck and Co., Rahway, N.J.

The following examples are offered by way of illustration and not by way of limitation.

EXAMPLES

I. Cells and Tissues.

Porcine fetal tissues, including aorta, brain, and liver, were obtained from a local slaughterhouse. Samples to be used later for isolation of DNA or RNA were flash frozen in liquid nitrogen, whereas aortic tissue was treated with collagenase in phosphate-buffered saline and pig aortic endothelial cells (PAEC) were isolated. PAEC were maintained in Dulbecco's modified Eagle medium (DMEM, Gibco, Grand Island, NY), 10,000 U of heparin sodium (Elkinns-Sinn, Inc., Cherry Hill, N.J.), 15 mg endothelium growth supplement (Collaborative Biomedical Products, Inc., Bedford, Mass.), L-glutamine, and penicillin-streptomycin. Culture flasks were kept loosely capped in a 37° C. incubator with an atmosphere of 5% $CO_2$.

II. Isolation of Nucleic Acids.

To isolate porcine genomic DNA, PAEC were grown to confluence in tissue culture flasks, trypsinized briefly at 37° C., and pelleted by centrifugation. High molecular weight porcine DNA was recovered using a standard protocol involving phenol-chloroform extraction, overnight incubation with RNase A, isopropanol precipitation, and spooling of precipitated DNA.

Total RNA was extracted from fetal tissue samples and cultured PAEC using Trizol reagent (Gibco) according to the manufacturer's instructions. For experiments in which polyadenylated (poly A+) RNA was used, poly A+RNA was separated from total RNA using the Dynabeads mRNA Purification Kit (Dynal, Oslo, Norway) in accord with the protocol provided. Total yield of poly A+RNA ranged from 1-5% of total RNA.

III. Genome Walking and Long PCR Amplification of Genomic DNA.

A combination strategy of PCR-based methods was employed. Such PCR methods are well known in the art and described, for example, in PCR Technology, H. A. Erlich, ed., Stockton Press, London, 1989; PCR Protocols: A Guide to Methods and Applications, M. A. Innis, D. H. Gelfand, J. J. Sninsky, and T. J. White, eds., Academic Press, Inc., New York, 1990; and Ausubel et al.

cDNA identification: To identify the porcine iGb3 synthase gene transcripts, PCR was performed using the Marathon cDNA Amplification Kit (Clontech) with porcine PAEC poly A+RNA as template. First strand cDNA synthesis from 1 µg of poly A+RNA was accomplished using 20 U of AMV-RT and 1 pmol of the supplied cDNA Synthesis Primer by incubating at 48° C. for 2 hr. Second strand cDNA synthesis involved incubating the entire first strand reaction with a supplied enzyme cocktail composed of RNase H, *Escherichia coli* DNA polymerase I, and *E. coli* DNA ligase at 16° C. for 1.5 hr. After blunting of the double-stranded cDNA ends by T4 DNA polymerase, the supplied Marathon cDNA Adapters were ligated to an aliquot of purified, double-stranded cDNA. Dilution of the adapter-ligated product in 10 mM tricme-KOH/0.1 mM EDTA buffer provided with the kit readied the cDNA for PCR amplification.

PCR reactions were performed with gene-specific primers (described in Table 7) generated based on the likely conserved homology between porcine iGb3 synthase and Rattus norvegicus iGb3 synthase mRNA (Genbank Accession # NM138524) (See Keusch J J et al., J Biol Chem. 2000 Aug. 18; 275(33):25308-14.). The strategy employed is described in Table 6.

Single major bands were obtained from two of the libraries, cloned, and subjected to sequence analysis. GenBank BLAST searches with those sequences revealed homology to exons 2, 3, 4, and 5 of the Rattus norvegicus and the human iGb3 synthase gene. Based on close inspection and comparison of the sequences from porcine, rat, and human DNA, primer sets identified in Table 8 were designed for Genome Walking analysis.

Genome Walking analysis: To identify exon-intron boundaries, or 5'-or 3'-flanking region of the transcripts, porcine GenomeWalker™ libraries were constructed using a Universal GenomeWalkeer™ Library kit (Clontech, Palo Alto, Calif.). Briefly, five aliquots of porcine genomic DNA were separately digested with a single blunt-cutting restriction endonuclease (DraI, EcoRV, PvuII, ScaI, or StuI). After phenol-chloroform extraction, ethanol precipitation and resuspension of the restricted fragments, a portion of each digested aliquot was used in separate ligation reactions with the GenomeWalker adapters provided with the kit. This process created five "libraries" for use in the PCR-based cloning strategy of GenomeWalking. Primer pairs identified in Table 8 were used in combination in a genome walking strategy. Primer pi4m was followed by a reaction with primer pi4n, and pi5A was followed by a reaction with primer pi5B. Either eLON-Gase or TaKaRa LA Taq (Takara Shuzo Co., Ltd., Shiga, Japan) enzyme was used for PCR in all GenomeWalker experiments as well as for direct long PCR of genomic DNA. The thermal cycling conditions recommended by the manufacturer were employed in all GW-PCR experiments on a Perkin Elmer Gene Amp System 9600 or 9700 thermocycler.

Subcloning and sequencing of amplified products: PCR products amplified from cDNA and Gene Walker-PCR (Clontech) were gel-purified using the Qiagen Gel Extraction Kit (Qiagen, Valencia, Calif.), if necessary, then subcloned into the pCR II vector provided with the Original TA Cloning Kit (Invitrogen, Carlsbad, Calif.). Plasmid DNA minipreps of pCR II-ligated inserts were prepared with the QlAprep Spin Miniprep Kit (Qiagen) as directed. Automated fluorescent sequencing of cloned inserts was performed using an ABI 377 Automated DNA Sequence Analyzer (Applied Biosystems, Inc., Foster City, Calif.) with either the dRhodamine or Big-Dye Terminator Cycle Sequencing Kits (Applied Biosystems) primed with T7 and SP6 promoter primers or primers designed from internal insert sequences.

Primer synthesis. Oligonucleotides used as primers in the various PCR-based methods were synthesized on an ABI 394 DNA Synthesizer (Applied Biosystems, Inc., Foster City, Calif.) using solid phase synthesis and phosphoramidite nucleoside chemistry.

TABLE 7

PRIMER SETS USED FOR cDNA PCR

| pi4A x pi5M | pi2A x pi4M |
|---|---|

TABLE 8

PRIMERS USED IN CDNA SYNTHESIS AND GENOMEWALKER PCR REACTIONS

| Primer Name | Sequence | |
|---|---|---|
| pi2A | 5'-AGGGCCTGGAAGAGAATCCTCT GGTG-3' | (Seq ID No. 16) |
| pi4A | 5'-AGGGCCCGGCCTGAAGTCCTGA CCTG-3' | (Seq ID No. 17) |
| pi4M | 5'-ACCTGCCTACAGCAAAGACCGT CAGG-3' | (Seq ID No. 18) |
| pi5M | 5'-CAGATCCACGTCCATGCAGAAC ACGA-3' | (Seq ID No. 19) |
| pi4m | 5'-CCCTTCGCTTGGACAGCACTGC TC-3' | (Seq ID No. 20) |
| pi4n | 5'-TCCCAGGCCTTACCTGCCCACA GC-3' | (Seq ID No. 21) |
| pi5A | 5'-ATGGTGGGCCAGTGCGTCGCGT AC-3' | (Seq ID No. 22) |
| pi5B | 5'-CGACCGTGGGCTACGGATGGAG C-3' | (Seq ID No. 23) |

IV. Construction of IGB3 Synthase Targeting Vector iGb3 Synthase gene knock-out target vector: A vector targeting Exon 4 of the porcine iGb3 Synthase gene for knock-out was constructed. In a first step, a fragment spanning from the immediate 5' portion of Exon 2 (i.e., Intron 1 region), and the immediate 5' portion of Exon 5 (i.e., Intron 4 region) was amplified by PCR. The primer sequences were as follows: SG1 (5'-CAGGGATTAACTCAACATCCAGGACAG-3' (Seq ID No. 14), which locates at 20 basepairs from the beginning of the sequence shown in this invention), and SG2

(5'-GAGTCAGCTGGTCACTGCGCCCTT-3' (Seq ID No. 15), which locates at 4733 base) (FIG. 4). The amplified PCR product was inserted into a pCRII vector from Invitrogen (termed pCRII/piGex234). Since there were two Stu I restriction sites in this fragment (one located 5' of Exon 4, and the other 3' of Exon 4), and since there was no Stu I sites in the pCRII vector sequence, a digestion with Stu I restriction enzyme followed by self-ligation of this vector resulted in the deletion of exon 4. Amplification of this vector with the SG1 and SG2 primers resulted in the production of an approximately 4.7 kbp of a linear fragment in which Exon 4 was deleted (termed L-pCRII/piGdelta4).

V. Production of Porcine IGB3 Synthase Deficient Fetal Fibroblast Cells

Fetal fibroblast cells can be isolated from 10 fetuses of the same pregnancy at day 33 of gestation. After removing the head and viscera, fetuses can be washed with Hanks' balanced salt solution (HBSS; Gibco-BRL, 1 5 Rockville, Md.), placed in 20 ml of HBSS, and diced with small surgical scissors. The tissue is then pelleted and resuspended in 50-ml tubes with 40 ml of DMEM and 100 U/ml collagenase (Gibco-BRL) per fetus. Tubes are incubated for 40 min in a shaking water bath at 37C. The digested tissue is allowed to settle for 3-4 min and the cell-rich supernatant can then be transferred to a new 50-ml tube and pelleted. The cells are then resuspended in 40 ml of DMEM containing 10% fetal calf serum (FCS), 1× nonessential amino acids, 1 mM sodium pyruvate and 2 ng/ml bFGF, and seeded into 10 cm. dishes. For transfections, 10 microgram of linearized L-pCRII/piGdelta4 vector can be introduced into 2 million cells using lipofectamine 2000 (Carlsbad, Calif.) following manufacturer's guidelines. Forty-eight hours after transfection, the transfected cells are seeded into 48-well plates at a density of 2,000 cells per well and grown to confluence.

Following confluence, cells are exposed with a serum free growth medium in which a lectin termed *H. pomatia* (HPA; Sigma-Aldrich Company Ltd, Poole, UK) is included at a concentration of 100 microgram/ml. Cells with terminal GalNAc-residues exhibit cytotoxicity with the lectin HPA (see, for example, Banchonglikitkul C et al., "An in-vitro evaluation of lectin cytotoxicity using cell lines derived from the ocular surface." J. Drug Target. 2002 Dec; 10:601-616), and differential expression of GalNac residues results in differential cytotoxicity. A homologous recombinant cell with one iGb3 synthase allele inactivated (i.e. iGb3 (+/−)) exhibits less expression of GalNAc-residues, allowing selection through the differential cytotoxicity with HPA compared to wild type cells. The selected cells can then be used as nuclear donors for the generation of cloned pigs deficient in at least one iGb3 synthase gene allele, or the further generation of iGb3 (−/−) fibroblasts.

Selected cells are then reseeded, and grown to confluency. Once confluency is reached, several small aliquots are frozen back for future use, and the remainders are utilized for PCR and Southern Blot verification of homologous recombination. The putative targeted clones can be screened by PCR using the primers set of SG1 and SG2 that across the Exon 4. The targeted allele is approximately 220 bp shorter than that of the wild type allele. The PCR product derived from wild type allele can be digested with PflM I restriction enzyme. Upon digestion, an allele lacking the recombinant vector will contain 4 fragments, while the "knocked-out" allele generated from the recombinant targeting vector will contain 3 fragments. A Southern Blot can be perfomed using a probe (i.e., the 220 bp of Stu I fragment) to identify the positive clones by the presence of the expected bands from the targeted allele.

Selection of iGb3 (−/−) cells from iGb3 (+/−) fibroblasts can be obtained by repeated cytotoxicity with HPA. Similar selection methods have previously been described, see, for example, Sharma A, et al., "Pig cells that lack the gene for α1-3 galactosyltransferase express low levels of the gal antigen," Transplantation. 2003 Feb 27;75:430-6. The iGb3 (−/−) cells can then be used as nuclear donor cells for the generation of cloned pigs homologous for iGb3 synthase knockouts.

VI. Generation of Cloned Pigs Using Heterologous or Homologous iGB3 Synthase Deficient Fetal Fibroblasts as Nuclear Donors Preparation of cells for Nuclear Transfer: Donor cells can be genetically manipulated to produce cells heterozygous or homologous for porcine iGb3 as described generally above. Nuclear transfer can be performed by methods that are well known in the art (see, e.g., Dai et al., Nature Biotechnology 20: 251255, 2002; and Polejaeva et al., Nature 407:86-90, 2000), using selected porcine fibroblasts as nuclear donors that are produced as described in detail hereinabove.

Oocytes can be isolated from synchronized super ovulated sexually mature Large-White X Landrace outcross gilts as described, for example, in I. Polejaeva et al. Nature 407: 505 (2000). Donor cells are synchronized in presumptive GO/GI by serum starvation (0.5%) between 24 to 120 hours. Oocytes enucleation, nuclear transfer, electrofusion, and electroactivation can be performed as essentially described in, for example, A. C. Boquest et al., Biol. Reproduction 68: 1283 (2002). Reconstructed embryos can be cultured overnight and can be transferred to the oviducts of asynchronous (−1 day) recipients. Pregnancies can be confirmed and monitored by real-time ultrasound.

Breeding of heterozygous iGb3 single knockout (SKO) male and female pigs can be performed to establish a mini-herd of double knockout (DKO) pigs.

This invention has been described with reference to its preferred embodiments. Variations and modifications of the invention, will be obvious to those skilled in the art from the foregoing detailed description of the invention. It is intended that all of these variations and modifications be included within the scope of this invention.

I claim:

1. An isolated cDNA sequence encoding a porcine IsoGloboside 3 (iGb3) synthase peptide, wherein the sequence comprises SEQ ID NO: 1.

2. A nucleic acid construct comprising a cDNA sequence encoding a porcine IsoGloboside 3 (iGb3) synthase protein, wherein the cDNA sequence comprises SEQ ID NO: 1.

3. The construct of claim 2 further comprising a promoter.

4. The construct of claim 2 further comprising a selectable marker.

5. The construct of claim 4 wherein the selectable marker is green fluorescent protein.

6. An isolated transfected cell comprising the construct of claim 2.

7. An isolated nucleotide sequence selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13.

8. A nucleic acid construct comprising at least 500 contiguous nucleic acids selected from the group consisting of SEQ ID NO: 6 and SEQ ID NO: 1.

9. The nucleic acid construct of claim 8, wherein the construct comprises at least 1000 nucleic acids.

10. A nucleic acid construct comprising a nucleic acid sequence encoding at least 160 contiguous amino acids of SEQ ID NO: 2.

* * * * *

SEQUENCE LISTING

<160> NUMBER OF SEQ ID NOS: 23

<210> SEQ ID NO 1
<211> LENGTH: 1440
<212> TYPE: DNA
<213> ORGANISM: Porcine

-continued

```
<400> SEQUENCE: 1
ggcctggaag agaatcctct ggtggttgat cctacttgca cttgacctct tagggctgct      60
cctgtttggc ctccctgctg tcaggcatct ggaagtcctt gtccccgtgg gtgtctgccc     120
tttgaccaga cacccctgc tgggagacaa ctccacgggt cccctgcatc cttgggcccg     180
gcctgaagtc ctgacctgca cctcctgggg gggccccatt atatgggacg gcaccttcga     240
cccagatgtg gcccagcaag aggctaccca gcagaacctc accattggcc tgacggtctt     300
tgctgtgggc aggtacctgg agaagtacct ggcacacttc ctggagacag cagagcagca     360
cttcatggtg ggccagtgcg tcgcgtacta cgtgttcacc gagcgccctg cagccatgcc     420
ccgcctgctg ctgggccccg accgtgggct acggatggag cacttggcgc gtgagcggcg     480
ctggcaggac gtgtccatgg cgcgcatgcg cgcgctgcac ccggcgctcg gggggcgcct     540
gggccacggg gcgtgcttcg tgttctgcat ggacgtggat cagcacttca gtggcgcctt     600
cgggcccgag gcgctggccg agtcggtggc gcagctgcac gctggcact accgctggcc     660 gcggtggctg ctgcccttg agcgtgacac gcgctcggcc gccgtgctgg gcccgggcga     720
gggcgacctc tactaccatg cggccgtgtt cgggggcagc gtggccgcgc tgcggcgtct     780
gacggcgcac tgcgcccggg gcctgcggcg ggaccgctcg cgcggcctag aggcgcgctg     840
gcacgacaag agccacctca ataagttctt ctggctgcac aagcccacca agctgctgtc     900
gcctgagttt tgctggagcc ccgatcttgg ccgctgggct gagatccact gcccgcgcct     960
gctctgggcg cccaaggagt atgccctgct gcaaagctag caatgccggt gagggcctt     1020 ctggaagcag cggggcactg ggggtggggg gagactgcgt gaacgcctcc cccgctgcgg    1080
catggctgca ggaagctggg cctttgggac gtggctcccg gaggaggatg agccatccct    1140
ttccatcgag acccgggcac ctccagctgc ctggagacca ttcacctctg accttactga    1200
gttcagcgga ggccctctga agagatgttt tagcccttc cccatatccc ctacgcttta    1260
tatggtactg aggcgccaaa agggaacatg atggcccgag acccagagg atctatgagt    1320 cagcctgtga ggtcagcagc tggagagcaa gactgaccct caggccaaat acatctgctt    1380
ctaggcacaa gccccagatg aagaaactca gtggcatccg gttccctgac tttgctggtt    1440

<210> SEQ ID NO 2
<211> LENGTH: 332
<212> TYPE: PRT
<213> ORGANISM: Porcine

<400> SEQUENCE: 2

Ala Trp Lys Arg Ile Leu Trp Trp Leu Ile Leu Leu Ala Leu Asp Leu
1               5                   10                  15

Leu Gly Leu Leu Leu Phe Gly Leu Pro Ala Val Arg His Leu Glu Val
                20                  25                  30

Leu Val Pro Val Gly Val Cys Pro Leu Thr Arg Thr Pro Leu Leu Gly
            35                  40                  45

Asp Asn Ser Thr Gly Pro Leu His Pro Trp Ala Arg Pro Glu Val Leu
        50                  55                  60

Thr Cys Thr Ser Trp Gly Gly Pro Ile Ile Trp Asp Gly Thr Phe Asp
65                  70                  75                  80

Pro Asp Val Ala Gln Gln Glu Ala Thr Gln Gln Asn Leu Thr Ile Gly
                85                  90                  95

Leu Thr Val Phe Ala Val Gly Arg Tyr Leu Glu Lys Tyr Leu Ala His
                100                 105                 110
```

Phe Leu Glu Thr Ala Glu Gln His Phe Met Val Gly Gln Cys Val Ala
            115                 120                 125

Tyr Tyr Val Phe Thr Glu Arg Pro Ala Ala Met Pro Arg Leu Leu Leu
        130                 135                 140

Gly Pro Asp Arg Gly Leu Arg Met Glu His Leu Ala Arg Glu Arg Arg
145                 150                 155                 160

Trp Gln Asp Val Ser Met Ala Arg Met Arg Ala Leu His Pro Ala Leu
                165                 170                 175

Gly Gly Arg Leu Gly His Gly Ala Cys Phe Val Phe Cys Met Asp Val
            180                 185                 190

Asp Gln His Phe Ser Gly Ala Phe Gly Pro Glu Ala Leu Ala Glu Ser
        195                 200                 205

Val Ala Gln Leu His Ala Trp His Tyr Arg Trp Pro Arg Trp Leu Leu
    210                 215                 220

Pro Phe Glu Arg Asp Thr Arg Ser Ala Ala Val Leu Gly Pro Gly Glu
225                 230                 235                 240

Gly Asp Leu Tyr Tyr His Ala Ala Val Phe Gly Ser Val Ala Ala
                245                 250                 255

Leu Arg Arg Leu Thr Ala His Cys Ala Arg Gly Leu Arg Arg Asp Arg
            260                 265                 270

Ser Arg Gly Leu Glu Ala Arg Trp His Asp Lys Ser His Leu Asn Lys
        275                 280                 285

Phe Phe Trp Leu His Lys Pro Thr Lys Leu Leu Ser Pro Glu Phe Cys
    290                 295                 300

Trp Ser Pro Asp Leu Gly Arg Trp Ala Glu Ile His Cys Pro Arg Leu
305                 310                 315                 320

Leu Trp Ala Pro Lys Glu Tyr Ala Leu Leu Gln Ser
                325                 330

<210> SEQ ID NO 3
<211> LENGTH: 84
<212> TYPE: DNA
<213> ORGANISM: Porcine

<400> SEQUENCE: 3
ggcctggaag agaatcctct ggtggttgat cctacttgca cttgacctct tagggctgct    60
cctgtttggc ctccctgctg tcag                                            84

<210> SEQ ID NO 4
<211> LENGTH: 90
<212> TYPE: DNA
<213> ORGANISM: Porcine

<400> SEQUENCE: 4
gcatctggaa gtccttgtcc ccgtgggtgt ctgcccttttg accagaacac ccctgctggg    60
agacaactcc acgggtcccc tgcatccttg                                      90

<210> SEQ ID NO 5
<211> LENGTH: 138
<212> TYPE: DNA
<213> ORGANISM: Porcine

<400> SEQUENCE: 5
ggcccggcct gaagtcctga cctgcacctc ctggggggggc cccattatat gggacggcac    60
cttcgaccca gatgtggccc agcaagaggc tacccagcag aacctcacca ttggcctgac    120
ggtctttgct gtgggcag                                                   138

<210> SEQ ID NO 6
<211> LENGTH: 1128
<212> TYPE: DNA
<213> ORGANISM: Porcine

<400> SEQUENCE: 6

```
gtacctggag aagtacctgg cacacttcct ggagacagca gagcagcact tcatggtggg      60
ccagtgcgtc gcgtactacg tgttcaccga gcgccctgca gccatgcccc gcctgctgct     120
gggcccccgac cgtgggctac ggatggagca cttggcgcgt gagcggcgct ggcaggacgt     180
gtccatggcg cgcatgcgcg cgctgcaccc ggcgctcggg gggcgcctgg ccacggggc      240
gtgcttcgtg ttctgcatgg acgtggatca gcacttcagt ggcgccttcg ggcccgaggc     300
gctggccgag tcggtggcgc agctgcacgc ctggcactac cgctggccgc ggtggctgct     360
gcccttttgag cgtgacacgc gctcggccgc cgtgctgggc ccgggcgagg gcgacctcta     420
ctaccatgcg gccgtgttcg ggggcagcgt ggccgcgctg cggcgtctga cggcgcactg     480
cgcccggggc ctgcggcggg accgctcgcg cggcctagag gcgcgctggc acgacaagag     540
ccacctcaat aagttcttct ggctgcacaa gcccaccaag ctgctgtcgc ctgagttttg     600
ctggagcccc gatcttggcc gctgggctga gatccactgc ccgcgcctgc tctgggcgcc     660
caaggagtat gccctgctgc aaagctagca atgccggtga gggcccttct ggaagcagcg     720
gggcactggg ggtgggggga gactgcgtga acgcctcccc cgctgcggca tggctgcagg     780
aagctgggcc tttgggacgt ggctcccgga ggaggatgag ccatccctttt ccatcgagac     840
ccgggcacct ccagctgcct ggagaccatt cacctctgac cttactgagt tcagcggagg     900
ccctctgaag agatgtttta gccccttccc catatcccct acgctttata tggtactgag     960
gcgccaaaag ggaacatgat ggcccgagga cccagaggat ctatgagtca gcctgtgagg    1020
tcagcagctg gagagcaaga ctgaccctca ggccaaatac atctgcttct aggcacaagc    1080
cccagatgaa gaaactcagt ggcatccggt tccctgactt tgctggtt                 1128
```

<210> SEQ ID NO 7
<211> LENGTH: 1401
<212> TYPE: DNA
<213> ORGANISM: Porcine

<400> SEQUENCE: 7

```
ccttgttcta acccttttagc agggattaac tcaacatcca ggacagccct ccaaagtagg      60
tgttcttagg acccaccttt ctagatgagg aaactcaggt gcggaggtcc agaaccttgc     120
ctgaggtcag acagctaaga agtggtggcc tgggattcga acccaggggg tcttgctcca     180
gcagtcttgc ttctcaccct aggggtccag tctgtctaga acaccagca cccagcaggg      240
gtgaggagag atgaagagaa tccccccaga ggagcttatt caaattcttc atttttgggc     300
ccttctggaa aacagccaac cacgctccaa tcctaaagta ctcctcctct gagccagcaa     360
agggggctggt acctctgctg gaggtacctg gcttggggac taagagccac catagacaca     420
gagtccctga gcacaggtgg ccctccgtgc agccagcaa tgcatctcta agccccagag     480
agctctcaac tcctagcttc caagcccacaa acttccctgc atccctctca gactctcccc     540
tgcccaaggt cagtcctaca cactgcctgg acgaagcgcc ccaccccta atggttactg      600
tcacttgagt gtgcctactg gaaaagcaa agaattaaac atctaaatgc tcatcaaaag     660
ggacctgggt gaggtaaagt gatgcccccct cccgtcaatg gcatgttagg cagctggaaa     720
```

```
aaggggtgag gaagcgcttc aaaaatagga agttccccat tgtggctcag ggggaaacaa    780
accccgcctt gtaccccatg aggatacggg ttcgatcccc ggcctcgctc agtgggttaa    840
ggatccggtg tcgctgtgag ctgcagtgtc agttgcaggc atggctcgag tcctgcgttg    900
ccgtggctgg ggcataggcc agcagctgca gctctgattt agccctagc ctgggaacct    960 ccacatgcca taggtgcggc cctaaaaagc aaaaaaaaa aaaaaaaaaa agagagagag   1020
agagagagag atggaataaa ctcaaagaca taatggtcag tggaaaatac aaggcaagga   1080
agagcatatc agcaggctac cgtgtgtggg aggaaaagca caggaagaga aggagagagc   1140
gcatttgcta ccgtatttac atttgcctgc atatacacga ctgtccccat gcagaggaac   1200
aggaaagact gcactgtcta tactctctag gacctttgaa tgtctgccat gtgcacagag   1260
taatatattc atagtcaaag caataaaat gaaacattaa attatatact ttcccatata   1320
tatgtatata tgtggaaatt acacacacac acatatatat tttgtgttgc taatgtccct   1380
ccctactccc cgcccaccca g                                           1401

<210> SEQ ID NO 8
<211> LENGTH: 201
<212> TYPE: DNA
<213> ORGANISM: Porcine

<400> SEQUENCE: 8
gtacaacccc cttcccctag tgctcaagat gggaccagca ggggagggtt aaagtggctc     60
tttcccagtg cctccttaag ggatagagag tgctggctct ctcctgcaca agtgtccttg    120
cgggctctcc cccttgtaag gagcaaagcc acagggctcc tgagcaggct gacacccctc    180
actgctgccc ccatccccca g                                             201

<210> SEQ ID NO 9
<211> LENGTH: 284
<212> TYPE: DNA
<213> ORGANISM: Porcine

<400> SEQUENCE: 9
gtaaggagct gccatctcca ggatctctgg gcctccagca ccccaccccc aagtccctgc     60
cctcctcgca tccccaccc tggcagggct aggcgctcca ccccagggcc ccagcaggtt    120
acacatctcg aaatacctg ctggatctgg ggtagagagt tctagggcag ggcctgggtg    180
tgacccactt gcaagtccct ggggcccagg cctgggagg tgacagtgac cacgcacgaa    240
gcaggtggat aatggacgaa tccctccatc cctgccctgg ctag                    284

<210> SEQ ID NO 10
<211> LENGTH: 2553
<212> TYPE: DNA
<213> ORGANISM: Porcine

<400> SEQUENCE: 10
gtaaggcctg ggaggcgagc agtgctgtcc aagcgaaggg ttgggagggg cgtgcatgtg     60
aagcagggcg tggggtgccc cattctccgg ggccacagca tcccaagcgg aagcagaagg    120
caaagacagc acctcctggg caagactcca agggtgaggc aggaccgacc cctccttccc    180
ttcctccctg acaccagca ccatggagcc cagccagcgc aggcagccgg gggctcagga    240
ccatgtcctg gaaggaacct ggctagtggt gagaaaacaa tggagttttt caggcgaaag    300
tgagaagagg tgagaactgg gtaagtagag gggatgaccc agctgcagtg agcgccccgc    360
ccccatggag gtcagtggct caggcgcagg ttagggaggg aggaagattc accaagcaag    420
```

-continued

```
tctgatggtg ggactggggc cggggacgg agggctcttg caagggagtg gatctgggct      480
gagtaaagag aaacgtgaag aaatggggat gcaacagtaa cgaacctgac taggacccat      540
gaggacccgg gttcaatccc tggcctcgct cagtgggtta aggatccagc gttgccgtga      600
ctgtggagta gtcgcagaca tggttcggat cccgagttgc tgtggctgtg cgtaggtgg       660
gcagttgcag ctccagcctg acccctagac tgggaacttc catatgccgg gggtgcgccc      720
ccccaaaaaa agaaagggg atgttgagag tggcagggtc agcaggccag agggctcagt       780
gagggaggac tatgggggt ggtatcagga agcgggctgg aaggacgggg ctgctgaggg       840
ggacgagtga ggccgcagtt tgggagggaa ggcagactga tgatgagcaa gctgagggag      900
aggtcatggg ggcaggtggc tcaggagagg aaggacaga ctctctccag gagaggaggc       960
caatcgagga agtgagaggc cccaggtat ggaggaggaa cctggaatgg taggtggaga      1020
actcacaagg gtgctggtct ccccatctcc cgattaggga tggcgggggg tccaagctgg     1080
gtactcactt tccagtagtg atgcaaatgg gactcctggc tgagagtggc acttagatcc     1140
tatagtccta aggctcagag aggtagagtt caggacaatt taaggagcg tttaataatg      1200
gaagaagctg ctttcgggag gcagtaaaaa gctttgcatc ccggaaaaga tatccaaaag     1260
tatctgatga attcagctcc tccaaatgac tcctctctgt ccctcacacc ctagacggga     1320
gaaagccagg aggacccctg ggaggccagg gtgcaaagag gaccaaggtg gacggaactg     1380
ctggcctctc cagggccttg atgtccccac ttccgttctg gatgctgagt agggtgttcc     1440
cataccagcc ctctgggtcc agaaattcca gagtcttgag atccaaattc caaggttcta     1500
tgagtccaac actctgggat gctgaggctt ccaaggtctc tcattccagt tttcacagtt     1560
ccaccaggaa tagaacaagt gcaggtaaag ctatgggctc cactgccaag cagggttcaa     1620
atcctggctt catacctacc agctgtgtgc gagggtgcat gagttcctaa agctcttgga     1680
gactgtttcc tcaccaggaa acggaactaa taatggtgag gattaaatga gataatacac     1740
attactttga acactctcac atgataaatg ttcaaaaaga tcaggcatta ttattattat     1800
tttagaacct taggatccca aagtctgttc atacagtttc cagtattctg gatgtctcga     1860
ttatctgtgt aaggaatcac tacaaacgca gtagctgaag gcagttcact attatcatag     1920
ctcatgactt tgtggctcaa gaattccgac tgctcagcag caaaggttca tcacttctct     1980
caaacagctg ggtctcctgt gagacagccg cctgaggaag actggcaggg tgcctctcca     2040
tggctagctt gggttctctc actctgtggc agtatcggag ttccaggact tcttatgcga     2100
agggtcagag ctctaaaggg acagaggcta acgcgcgggt cttcccaagg cccagcatgg     2160
catcccttcc ttgtgcctct attgatcaaa ggggtccggg agagccgagt tcaagggaag     2220
ggacacaggg gctctagggg cagggctggc aaacaatgga caattgttat gattattatt     2280
taccacacct tccgcatgag gaagttcttg ggccaggatt ccaacccagg ccagggatca     2340
aacccgtgac ccaagccaca gtagtaacaa cgccagatcc ttaacttgct gagccaccaa     2400
ggaactccaa ttggcaatta attttaattt gcctccaacg gggactgccc tttccggagt     2460
tcctgggcct ggggtcgcag ggtcaccaga acggacatgg gggcggctgg aagggcgca     2520
gtgaccagct gactcggacg gcccgctccg cag                                  2553
```

<210> SEQ ID NO 11
<211> LENGTH: 5879
<212> TYPE: DNA
<213> ORGANISM: Porcine

<400> SEQUENCE: 11

```
ccttgttcta acccctttagc agggattaac tcaacatcca ggacagccct ccaaagtagg       60
tgttcttagg acccaccttt ctagatgagg aaactcaggt gcggaggtcc agaaccttgc      120
ctgaggtcag acagctaaga agtggtggcc tgggattcga acccagggag tcttgctcca      180
gcagtcttgc ttctcaccct aggggtccag tctgtctaga aacaccagca cccagcaggg      240
gtgaggagag atggaagaga tcccccaga ggagcttatt caaattcttc atttttgggc       300
ccttctggaa aacagccaac cacgctccaa tcctaaagta ctcctcctct gagccagcaa      360
aggggctggt acctctgctg gaggtacctg gcttggggac taagagccac catagacaca      420
gagtccctga gcacaggtgg ccctccgtgc agcccagcaa tgcatctcta agccccagag      480
agctctcaac tcctagcttc caagccacaa acttccctgc atccctctca gactctcccc      540
tgcccaaggt cagtcctaca cactgcctgg acgaagcgcc ccacccccta atggttactg      600
tcacttgagt gtgcctactg ggaaaagcaa agaattaaac atctaaatgc tcatcaaaag      660
ggacctgggt gaggtaaagt gatgccccct cccgtcaatg gcatgttagg cagctggaaa      720
aaggggtgag gaagcgcttc aaaaatagga agttccccat tgtggctcag ggggaaacaa      780
accccgcctt gtaccccatg aggatacggg ttcgatcccc ggcctcgctc agtgggttaa      840
ggatccggtc tcgctgtgag ctgcagtgtc agttgcaggc atggctcgag tcctgcgttg      900
ccgtggctgg ggcataggcc agcagctgca gctctgattt agcccctagc ctgggaacct      960
ccacatgcca taggtgcggc cctaaaaagc aaaaaaaaaa aaaaaaaaa agagagagag      1020
agagagagag atggaataaa ctcaaagaca taatggtcag tggaaaatac aaggcaagga      1080
agagcatatc agcaggctac cgtgtgtggg aggaaaagca caggaagaga aggagagagc      1140
gcatttgcta ccgtatttac atttgcctgc atatacacga ctgtccccat gcagaggaac      1200
aggaaagact gcactgtcta tactctctag gaccttgaa tgtctgccat gtgcacagag       1260
taatatattc atagtcaaag caaataaaat gaaacattaa attatatact ttcccatata      1320
tatgtatata tgtggaaatt acacacacac acatatatat tttgtgttgc taatgtccct      1380
ccctactccc cgcccaccca gggcctggaa gagaatcctc tggtggttga tcctacttgc      1440
acttgacctc ttagggctgc tcctgtttgg cctccctgct gtcaggtaca accccttcc       1500
cctagtgctc aagatgggac cagcagggga gggttaaagt ggctctttcc cagtgcctcc      1560
ttaagggata gagagtgctg gctctctcct gcacaagtgt ccttgcgggc tctccccctt      1620
gtaaggagca aagccacagg gctcctgagc aggctgacac ccctcactgc tgcccccatc      1680
ccccaggcat ctggaagtcc ttgtccccgt gggtgtctgc cctttgacca gaacacccct      1740
gctgggagac aactccacgg gtcccctgca tccttggtaa ggagctgcca tctccaggat      1800
ctctgggcct ccagcacccc acccccaagt ccctgccctc ctcgcatccc ccacctggc       1860
agggctaggc gctccacccc agggcccag caggttacac atctcgaaat accctgctgg       1920
atctggggta gagagttcta gggcagggcc tgggtgtgac ccacttgcaa gtccctgggg      1980
cccaggcctg ggaggtgac agtgaccacg cacgaagcag gtggataatg gacgaatccc       2040
tccatccctg ccctggctag ggcccggcct gaagtcctga cctgcacctc ctggggggc       2100
cccattatat gggacggcac cttcgaccca gatgtgccc agcaagaggc tacccagcag       2160
aacctcacca ttggcctgac ggtctttgct gtgggcaggt aaggcctggg aggcgagcag      2220
tgctgtccaa gcgaagggtt gggaggggcg tgcatgtgaa gcaggcgtg gggtgcccca       2280
ttctccgggg ccacagcatc ccaagcggaa gcagaaggca aagacagcac ctcctgggca      2340
```

```
agactccaag ggtgaggcag gaccgacccc tccttcccct cctccctgga caccagcacc    2400
atggagccca gccagcgcag gcagccgggg gctcaggacc atgtcctgga aggaacctgg    2460
ctagtggtga gaaaacaatg gagtttttca ggcgaaagtg agaagaggtg agaactgggt    2520
aagtagaggg gatgacccag ctgcagtgag cgccccgccc ccatggaggt cagtggctca    2580
ggcgcaggtt agggagggag gaagattcac caagcaagtc tgatggtggg actgggccg     2640 ggggacggag ggctcttgca agggagtgga tctgggctga gtaaagagaa acgtgaagaa    2700
atggggatgc aacagtaacg aacctgacta ggacccatga ggacccgggt tcaatccctg    2760
gcctcgctca gtgggttaag gatccagcgt tgccgtgact gtggagtagt cgcagacatg    2820
gttcggatcc cgagttgctg tggctgtggc gtaggtgggc agttgcagct ccagcctgac    2880
ccctagactg ggaacttcca tatgccgggg gtgcgccccc ccaaaaaaag aaaggggat     2940 gttgagagtg gcagggtcag caggccagag ggctcagtga gggaggacta tggggggtgg    3000
tatcaggaag cgggctggaa ggacggggct gctgaggggg acgagtgagg ccgcagtttg    3060
ggagggaagg cagactgatg atgagcaagc tgagggagag gtcatggggg caggtggctc    3120
aggagaggga aggacagact ctctccagga gaggaggcca atcgaggaag tgagaggccc    3180
ccaggtatgg aggaggaacc tggaatggta gtgtggagaac tcacaagggt gctggtctcc    3240
ccatctcccg attagggatg gcgggggggtc caagctgggt actcactttc cagtagtgat    3300
gcaaatggga ctcctggctg agagtggcac ttagatccta tagtcctaag gctcagagag    3360
gtagagttca ggacaattta agggagcgtt taataatgga agaagctgct ttcgggaggc    3420
agtaaaaagc tttgcatccc ggaaaagata tccaaaagta tctgatgaat tcagctcctc    3480
caaatgactc ctctctgtcc ctcacaccct agacgggaga aagccaggag gacccctggg    3540
aggccagggt gcaaagagga ccaaggtgga cggaactgct ggcctctcca gggccttgat    3600
gtccccactt ccgttctgga tgctgagtag ggtgttccca taccagccct ctgggtccag    3660
aaattccaga gtcttgagat ccaaattcca aggttctatg agtccaacac tctgggatgc    3720
tgaggcttcc aaggtctctc attccagttt tcacagttcc accaggaata gaacaagtgc    3780
aggtaaagct atgggctcca ctgccaagca gggttcaaat cctggcttca tacctaccag    3840
ctgtgtgcga gggtgcatga gttcctaaag ctcttggaga ctgtttcctc accaggaaac    3900
ggaactaata atggtgagga ttaaatgaga taatacacat tactttgaac actctcacat    3960
gataaatgtt caaaagatc aggcattatt attattattt tagaaccta ggatcccaaa     4020 gtctgttcat acagtttcca gtattctgga tgtctcgatt atctgtgtaa ggaatcacta    4080
caaacgcagt agctgaaggc agttcactat tatcatagct catgactttg tggctcaaga    4140
attccgactg ctcagcagca aaggttcatc acttctctca aacagctggg tctcctgtga    4200
gacagccgcc tgaggaagac tggcaggtg cctctccatg gctagcttgg gttctctcac     4260
tctgtggcag tatcggagtt ccaggacttc ttatgcgaag ggtcagagct ctaaagggac    4320
agaggctaac gcgcgggtct tcccaaggcc cagcatggca tcccttcctt gtgcctctat    4380
tgatcaaagg ggtccgggag agccgagttc aagggaaggg acacaggggc tctagggggca   4440 gggctggcaa acaatggaca attgttatga ttattattta ccacaccttc cgcatgagga    4500
agttcttggg ccaggattcc aacccaggcc agggatcaaa cccgtgaccc aagccacagt    4560
agtaacaacg ccagatcctt aacttgctga gccaccaagg aactccaatt ggcaattaat    4620
tttaatttgc ctccaacggg gactgcccct tccggagttc ctgggcctgg ggtcgcaggg    4680
```

-continued

| | |
|---|---|
| tcaccagaac ggacatgggg gcggctggga agggcgcagt gaccagctga ctcggacggc | 4740 |
| ccgctccgca ggtacctgga gaagtacctg gcacacttcc tggagacagc agagcagcac | 4800 |
| ttcatggtgg gccagtgcgt cgcgtactac gtgttcaccg agcgccctgc agccatgccc | 4860 |
| cgcctgctgc tgggccccga ccgtgggcta cggatggagc acttggcgcg tgagcggcgc | 4920 |
| tggcaggacg tgtccatggc gcgcatgcgc gcgctgcacc cggcgctcgg ggggcgcctg | 4980 |
| ggccacgggg cgtgcttcgt gttctgcatg gacgtggatc agcacttcag tggcgccttc | 5040 |
| gggcccgagg cgctggccga gtcggtggcg cagctgcacg cctggcacta ccgctggccg | 5100 |
| cggtggctgc tgccctttga gcgtgacacg cgctcggccg ccgtgctggg cccgggcgag | 5160 |
| ggcgacctct actaccatgc ggccgtgttc ggggggcagcg tggccgcgct gcggcgtctg | 5220 |
| acggcgcact gcgcccgggg cctgcggcgg gaccgctcgc gcggcctaga ggcgcgctgg | 5280 |
| cacgacaaga gccacctcaa taagttcttc tggctgcaca agcccaccaa gctgctgtcg | 5340 |
| cctgagtttt gctggagccc cgatcttggc cgctgggctg agatccactg cccgcgcctg | 5400 |
| ctctgggcgc ccaaggagta tgccctgctg caaagctagc aatgccggtg agggcccttc | 5460 |
| tggaagcagc ggggcactgg gggtgggggg agactgcgtg aacgcctccc ccgctgcggc | 5520 |
| atggctgcag gaagctgggc cttttgggacg tggctcccgg aggaggatga gccatcccct | 5580 |
| tccatcgaga cccgggcacc tccagctgcc tggagaccat tcacctctga ccttactgag | 5640 |
| ttcagcggag gccctctgaa gagatgtttt agccccttcc ccatatcccc tacgctttat | 5700 |
| atggtactga ggcgccaaaa gggaacatga tggcccgagg acccagagga tctatgagtc | 5760 |
| agcctgtgag gtcagcagct ggagagcaag actgaccctc aggccaaata catctgcttc | 5820 |
| taggcacaag ccccagatga agaaactcag tggcatccgg ttccctgact ttgctggtt | 5879 |

<210> SEQ ID NO 12
<211> LENGTH: 5879
<212> TYPE: DNA
<213> ORGANISM: Porcine

<400> SEQUENCE: 12

| | |
|---|---|
| ccttgttcta acccttagc agggattaac tcaacatcca ggacagccct ccaaagtagg | 60 |
| tgttcttagg acccaccttt ctagatgagg aaactcaggt gcggaggtcc agaaccttgc | 120 |
| ctgaggtcag acagctaaga agtggtggcc tgggattcga acccaggggg tcttgctcca | 180 |
| gcagtcttgc ttctcaccct aggggtccag tctgtctaga aacaccagca cccagcaggg | 240 |
| gtgaggagag atgaagaga tcccccaga ggagcttatt caaattcttc attttttgggc | 300 |
| ccttctggaa aacagccaac cacgctccaa tcctaaagta ctcctcctct gagccagcaa | 360 |
| aggggctggt acctctgctg gaggtacctg gcttggggac taagagccac catagacaca | 420 |
| gagtccctga gcacaggtgg ccctccgtgc agcccagcaa tgcatctcta agccccagag | 480 |
| agctctcaac tcctagcttc caagccacaa acttccctgc atccctctca gactctcccc | 540 |
| tgcccaaggt cagtcctaca cactgcctgg acgaagcgcc ccaccccta atggttactg | 600 |
| tcacttgagt gtgcctactg ggaaaagcaa agaattaaac atctaaatgc tcatcaaaag | 660 |
| ggacctgggt gaggtaaagt gatgccccct ccgtcaatg gcatgttagg cagctggaaa | 720 |
| aagggggtgag gaagcgcttc aaaaatagga agttccccat tgtggctcag ggggaaacaa | 780 |
| accccgcctt gtaccccatg aggatacggg ttcgatcccc ggcctcgctc agtgggttaa | 840 |
| ggatccggtg tcgctgtgag ctgcagtgtc agttgcaggc atggctcgag tcctgcgttg | 900 |
| ccgtggctgg ggcataggcc agcagctgca gctctgattt agcccctagc ctgggaacct | 960 |

```
ccacatgcca taggtgcggc cctaaaaagc aaaaaaaaaa aaaaaaaaaa agagagagag    1020
agagagagag atggaataaa ctcaaagaca taatggtcag tggaaaatac aaggcaagga    1080
agagcatatc agcaggctac cgtgtgtggg aggaaaagca caggaagaga aggagagagc    1140
gcatttgcta ccgtatttac atttgcctgc atatacacga ctgtccccat gcagaggaac    1200
aggaaagact gcactgtcta tactctctag gacctttgaa tgtctgccat gtgcacagag    1260
taatatattc atagtcaaag caaataaaat gaaacattaa attatatact ttcccatata    1320
tatgtatata tgtggaaatt acacacacac acatatatat tttgtgttgc taatgtccct    1380
ccctactccc cgcccaccca gggcctggaa gagaatcctc tggtggttga tcctacttgc    1440
acttgacctc ttagggctgc tcctgtttgg cctccctgct gtcaggtaca acccccttcc    1500
cctagtgctc aagatgggac cagcagggga gggttaaagt ggctcttttcc cagtgcctcc    1560 ttaagggata gagagtgctg gctctctcct gcacaagtgt ccttgcgggc tctcccctt    1620 gtaaggagca aagccacagg gctcctgagc aggctgacac ccctcactgc tgccccatc    1680 ccccaggcat ctggaagtcc ttgtcccgt gggtgtctgc cctttgacca gaacacccct    1740
gctgggagac aactccacgg gtcccctgca tccttggtaa ggagctgcca tctccaggat    1800
ctctgggcct ccagcacccc acccccaagt ccctgccctc ctcgcatccc ccaccctggc    1860
agggctaggc gctccacccc agggcccag caggttacac atctcgaaat accctgctgg    1920
atctggggta gagagttcta gggcagggcc tgggtgtgac ccacttgcaa gtccctgggg    1980
cccaggcctg ggaggtgac agtgaccacg cacgaagcag gtggataatg gacgaatccc    2040
tccatccctg ccctggctag ggcccggcct gaagtcctga cctgcacctc ctgggggggc    2100
cccattatat gggacggcac cttcgaccca gatgtggccc agcaagaggc tacccagcag    2160
aacctcacca ttggcctgac ggtctttgct gtgggcaggt aaggcctggg aggcgagcag    2220
tgctgtccaa gcgaagggtt gggaggggcg tgcatgtgaa gcaggcgtg gggtgcccca    2280 ttctccgggg ccacagcatc ccaagcggaa gcagaaggca aagacagcac ctcctgggca    2340
agactccaag ggtgaggcag gaccgacccc tccttcccctt cctccctgga caccagcacc    2400
atggagccca gccagcgcag gcagccgggg gctcaggacc atgtcctgga aggaacctgg    2460
ctagtggtga gaaaacaatg gagttttca ggcgaaagtg agaagaggtg agaactgggt    2520
aagtagaggg gatgacccag ctgcagtgag cgccccgccc ccatggaggt cagtggctca    2580
ggcgcaggtt agggagggag gaagattcac caagcaagtc tgatggtggg actggggccg    2640
ggggacggag ggctcttgca agggagtgga tctgggctga gtaaagagaa acgtgaagaa    2700
atggggatgc aacagtaacg aacctgacta ggacccatga ggacccgggt tcaatccctg    2760
gcctcgctca gtgggttaag gatccagcgt tgccgtgact gtggagtagt cgcagacatg    2820
gttcggatcc cgagttgctg tggctgtggc gtaggtgggc agttcagct ccagcctgac    2880 ccctagactg ggaacttcca tatgccgggg gtgcgccccc ccaaaaaaag aaaggggat    2940 gttgagagtg gcagggtcag caggccagag ggctcagtga gggaggacta tggggggtgg    3000
tatcaggaag cgggctggaa ggacggggct gctgagggg acgagtgagg ccgcagtttg    3060
ggagggaagg cagactgatg atgagcaagc tgagggagag gtcatggggg caggtggctc    3120
aggagaggga aggacagact ctctccagga gaggaggcca atcgaggaag tgagaggccc    3180
ccaggtatgg aggaggaacc tggaatggta ggtggagaac tcacaagggt gctggtctcc    3240
ccatctcccg attagggatg gcggggggtc caagctgggt actcactttc cagtagtgat    3300
```

```
gcaaatggga ctcctggctg agagtggcac ttagatccta tagtcctaag gctcagagag    3360
gtagagttca ggacaattta agggagcgtt taataatgga agaagctgct ttcgggaggc    3420
agtaaaaagc tttgcatccc ggaaaagata tccaaaagta tctgatgaat tcagctcctc    3480
caaatgactc ctctctgtcc ctcacaccct agacgggaga aagccaggag gaccccgggg    3540
aggccagggt gcaaagagga ccaaggtgga cggaactgct ggcctctcca gggccttgat    3600
gtccccactt ccgttctgga tgctgagtag ggtgttccca taccagccct ctgggtccag    3660
aaattccaga gtcttgagat ccaaattcca aggttctatg agtccaacac tctgggatgc    3720
tgaggcttcc aaggtctctc attccagttt tcacagttcc accaggaata gaacaagtgc    3780
aggtaaagct atgggctcca ctgccaagca gggttcaaat cctggcttca tacctaccag    3840
ctgtgtgcga gggtgcatga gttcctaaag ctcttggaga ctgtttcctc accaggaaac    3900
ggaactaata atggtgagga ttaaatgaga taatacacat tactttgaac actctcacat    3960
gataaatgtt caaaagatc aggcattatt attattattt tagaacctta ggatcccaaa    4020
gtctgttcat acagtttcca gtattctgga tgtctcgatt atctgtgtaa ggaatcacta    4080
caaacgcagt agctgaaggc agttcactat tatcatagct catgactttg tggctcaaga    4140
attccgactg ctcagcagca aaggttcatc acttctctca aacagctggg tctcctgtga    4200
gacagccgcc tgaggaagac tggcagggtg cctctccatg gctagcttgg gttctctcac    4260
tctgtggcag tatcggagtt ccaggacttc ttatgcgaag ggtcagagct ctaaagggac    4320
agaggctaac gcgcgggtct tcccaaggcc cagcatggca tcccttcctt gtgcctctat    4380
tgatcaaagg ggtccgggag agccgagttc aagggaaggg acacaggggc tctagggca     4440
gggctggcaa acaatggaca attgttatga ttattattta ccacaccttc cgcatgagga    4500
agttcttggg ccaggattcc aacccaggcc agggatcaaa cccgtgaccc aagccacagt    4560
agtaacaacg ccagatcctt aacttgctga gccaccaagg aactccaatt ggcaattaat    4620
tttaatttgc ctccaacggg gactgccctt tccggagttc ctgggcctgg ggtcgcaggg    4680
tcaccagaac ggacatgggg gcggctggga agggcgcagt gaccagctga ctcggacggc    4740
ccgctccgca ggtacctgga gaagtacctg gcacacttcc tggagacagc agagcagcac    4800
ttcatggtgg gccagtgcgt cgcgtactac gtgttcaccg agcgccctgc agccatgccc    4860
cgcctgctgc tgggccccga ccgtgggcta cggatggagc acttggcgcg tgagcggcgc    4920
tggcaggacg tgtccatggc gcgcatgcgc gcgctgcacc cggcgctcgg ggggcgcctg    4980
ggccacgggg cgtgcttcgt gttctgcatg gacgtggatc agcacttcag tggcgccttc    5040
gggcccgagg cgctggccga gtcggtggcg cagctgcacg cctggcacta ccgctggccg    5100
cggtggctgc tgccctttga gcgtgacacg cgctcggccg ccgtgctggg cccgggcgag    5160
ggcgacctct actaccatgc ggccgtgttc ggggcagcg tggccgcgct gcggcgtctg     5220
acggcgcact gcgcccgggg cctgcggcgg gaccgctcgc gcggcctaga ggcgcgctgg    5280
cacgacaaga gccacctcaa taagttcttc tggctgcaca agcccaccaa gctgctgtcg    5340
cctgagtttt gctggagccc cgatcttggc cgctgggctg agatccactg cccgcgcctg    5400
ctctgggcgc ccaaggagta tgccctgctg caaagctagc aatgccggtg agggcccttc    5460
tggaagcagc ggggcactgg gggtgggggg agactgcgtg aacgcctccc ccgctgcggc    5520
atggctgcag gaagctgggc ctttgggacg tggctcccgg aggaggatga gccatccctt    5580
tccatcgaga cccgggcacc tccagctgcc tggagaccat tcacctctga ccttactgag    5640
ttcagcggag gccctctgaa gagatgtttt agccccttcc ccatatcccc tacgctttat    5700
```

```
atggtactga ggcgccaaaa gggaacatga tggcccgagg acccagagga tctatgagtc    5760
agcctgtgag gtcagcagct ggagagcaag actgaccctc aggccaaata catctgcttc    5820
taggcacaag ccccagatga agaaactcag tggcatccgg ttccctgact ttgctggtt     5879
```

<210> SEQ ID NO 13
<211> LENGTH: 595
<212> TYPE: DNA
<213> ORGANISM: Porcine

<400> SEQUENCE: 13

```
gacaagagcc acctcaataa gttcttctgg ctgcacaagc ccaccaagct gctgtcgcct      60
gagttttgct ggagccccga tcttggccgc tgggctgaga tccactgccc gcgcctgctc     120
tgggcgccca aggagtatgc cctgctgcaa agctagcaat gccggtgagg gcccttctgg     180
aagcagcggg gcactggggg tgggggggaga ctgcgtgaac gcctccccg ctgcggcatg     240 gctgcaggaa gctgggcctt tgggacgtgg ctcccggagg aggatgagcc atcccttttcc    300 atcgagaccc gggcacctcc agctgcctgg agaccattca cctctgacct tactgagttc     360
agcggaggcc ctctgaagag atgttttagc cccttcccca tatcccctac gctttatatg     420
gtactgaggc gccaaaaggg aacatgatgg cccgaggacc cagaggatct atgagtcagc     480
ctgtgaggtc agcagctgga gagcaagact gaccctcagg ccaaatacat ctgcttctag     540
gcacaagccc cagatgaaga aactcagtgg catccggttc cctgactttg ctggt           595
```

<210> SEQ ID NO 14
<211> LENGTH: 27
<212> TYPE: DNA
<213> ORGANISM: Artificial
<220> FEATURE:
<223> OTHER INFORMATION: Primer

<400> SEQUENCE: 14

```
cagggattaa ctcaacatcc aggacag                                           27
```

<210> SEQ ID NO 15
<211> LENGTH: 24
<212> TYPE: DNA
<213> ORGANISM: Artificial
<220> FEATURE:
<223> OTHER INFORMATION: Primer

<400> SEQUENCE: 15

```
gagtcagctg gtcactgcgc cctt                                              24
```

<210> SEQ ID NO 16
<211> LENGTH: 26
<212> TYPE: DNA
<213> ORGANISM: Artificial
<220> FEATURE:
<223> OTHER INFORMATION: Primer

<400> SEQUENCE: 16

```
agggcctgga agagaatcct ctggtg                                            26
```

<210> SEQ ID NO 17
<211> LENGTH: 26
<212> TYPE: DNA
<213> ORGANISM: Artificial
<220> FEATURE:
<223> OTHER INFORMATION: Primer

```
<400> SEQUENCE: 17
agggcccggc ctgaagtcct gacctg                                         26

<210> SEQ ID NO 18
<211> LENGTH: 26
<212> TYPE: DNA
<213> ORGANISM: Artificial
<220> FEATURE:
<223> OTHER INFORMATION: Primer

<400> SEQUENCE: 18
acctgcctac agcaaagacc gtcagg                                         26

<210> SEQ ID NO 19
<211> LENGTH: 26
<212> TYPE: DNA
<213> ORGANISM: Artificial
<220> FEATURE:
<223> OTHER INFORMATION: Primer

<400> SEQUENCE: 19
cagatccacg tccatgcaga acacga                                         26

<210> SEQ ID NO 20
<211> LENGTH: 24
<212> TYPE: DNA
<213> ORGANISM: Artificial
<220> FEATURE:
<223> OTHER INFORMATION: Primer

<400> SEQUENCE: 20
cccttcgctt ggacagcact gctc                                           24

<210> SEQ ID NO 21
<211> LENGTH: 24
<212> TYPE: DNA
<213> ORGANISM: Artificial
<220> FEATURE:
<223> OTHER INFORMATION: Primer

<400> SEQUENCE: 21
tcccaggcct tacctgccca cagc                                           24

<210> SEQ ID NO 22
<211> LENGTH: 24
<212> TYPE: DNA
<213> ORGANISM: Artificial
<220> FEATURE:
<223> OTHER INFORMATION: Primer

<400> SEQUENCE: 22
atggtgggcc agtgcgtcgc gtac                                           24

<210> SEQ ID NO 23
<211> LENGTH: 23
<212> TYPE: DNA
<213> ORGANISM: Artificial
<220> FEATURE:
<223> OTHER INFORMATION: Primer

<400> SEQUENCE: 23
cgaccgtggg ctacggatgg agc                                            23
```